(12) United States Patent
Virtanen

(10) Patent No.: US 6,312,901 B2
(45) Date of Patent: Nov. 6, 2001

(54) SPATIALLY ADDRESSABLE, CLEAVABLE REFLECTIVE SIGNAL ELEMENTS, ASSAY DEVICE AND METHOD

(75) Inventor: Jorma Virtanen, Irvine, CA (US)

(73) Assignee: Burstein Technologies, Inc., Irvine, CA (US)

( * ) Notice: Subject to any disclaimer, the term of this patent is extended or adjusted under 35 U.S.C. 154(b) by 30 days.

(21) Appl. No.: 09/394,137

(22) Filed: Sep. 10, 1999

Related U.S. Application Data

(63) Continuation of application No. 08/888,935, filed on Jul. 17, 1997, now abandoned.
(60) Provisional application No. 60/021,367, filed on Jul. 8, 1996, and provisional application No. 60/030,416, filed on Nov. 1, 1996.

(51) Int. Cl.[7] .............................. C12Q 1/68; C12Q 1/00; C12Q 1/70; C07H 19/00; G01N 33/566
(52) U.S. Cl. ................. 435/6; 435/4; 435/5; 435/7.1; 435/7.2; 435/7.93; 435/7.94; 435/7.95; 435/810; 536/22.1; 436/501; 436/512
(58) Field of Search ................... 435/6, 4, 5, 7.1, 435/7.21, 7.93, 7.94, 7.95, 810; 536/22.1; 436/501, 512

(56) References Cited

U.S. PATENT DOCUMENTS

| | | | |
|---|---|---|---|
| Re. 33,064 | 9/1989 | Carter et al. | 436/34 |
| 3,646,346 | 2/1972 | Catt | 250/83 |
| 3,791,932 | 2/1974 | Schuurs et al. | 195/103.5 R |
| 3,817,837 | 6/1974 | Rubenstein et al. | 195/103.5 R |
| 3,817,838 | 6/1974 | Harris et al. | 195/103.5 R |
| 3,850,752 | 11/1974 | Schuurs et al. | 195/103.5 R |
| 3,939,350 | 2/1976 | Kronick et al. | 250/365 |
| 3,996,345 | 12/1976 | Ullman et al. | 424/12 |
| 4,037,257 | 7/1977 | Chari | 360/51 |
| 4,062,733 | 12/1977 | Edwards et al. | 195/103.7 |

(List continued on next page.)

FOREIGN PATENT DOCUMENTS

| | | | |
|---|---|---|---|
| 0 392 475 A2 | 10/1990 | (EP) | G01N/1/28 |
| 0 417 305 A1 | 3/1991 | (EP) | G01N/35/00 |
| 0 504 432 A1 | 9/1992 | (EP) | G01N/33/543 |
| 0 521 421 A2 | 1/1993 | (EP) . | |
| WO 95/34890 | 12/1995 | (WO) | G11B/7/00 |
| WO 96/09548 | 3/1996 | (WO) | G01N/33/543 |
| WO 96/35940 | 11/1996 | (WO) | G01N/21/77 |
| WO 97/21090 | 6/1997 | (WO) . | |

(List continued on next page.)

OTHER PUBLICATIONS

Butcher, A. et al., "Using PCR for Detection of HIV–1 Infection," *Clinical Immunology Newsletter*, 12(5):73–76 (1992).

Cheng, J. et al., "Preparation and Hybridization Analysis of DNA/RNA from *E. Coli* on Microfabricated Bioelectronic Chips," *Nature Biotechnology*, 16(6):541–546 (1998).

Diamandis, E. et al. (eds), *Immunoassay*, Academic Press (1996).

(List continued on next page.)

*Primary Examiner*—Jezia Riley

(57) ABSTRACT

A cleavable signal element for use in quantitative and qualitative assay devices and methods is described. Binding of the chosen analyte simultaneously to a first and a second analyte-specific side member of the cleavable signal element tethers the signal-responsive moiety to the signal element's substrate-attaching end, despite subsequent cleavage at the cleavage site that lies intermediate the first and second side members. Assay devices comprising the cleavable signal elements are described, as are analytic methods adapted to their use. The analytic devices of the present invention may be adapted to detection using conventional CD-ROM and DVD readers.

17 Claims, 34 Drawing Sheets

U.S. PATENT DOCUMENTS

| | | |
|---|---|---|
| 4,104,029 | 8/1978 | Maier, Jr. .............................. 23/230 B |
| 4,160,645 | 7/1979 | Ullman ................................. 23/230 B |
| 4,233,402 | 11/1980 | Maggio et al. ............................ 435/7 |
| 4,275,149 | 6/1981 | Litman et al. ............................ 435/7 |
| 4,277,437 | 7/1981 | Maggio .................................... 422/61 |
| 4,287,300 | 9/1981 | Gibbons et al. ........................... 435/5 |
| 4,472,509 | 9/1984 | Gansow et al. ........................ 436/548 |
| 4,542,102 | 9/1985 | Dattagupta et al. ....................... 435/6 |
| 4,608,344 | 8/1986 | Carter et al. ............................ 436/34 |
| 4,756,971 | 7/1988 | Virtanen et al. ...................... 428/405 |
| 4,780,421 * | 10/1988 | Kameda et al. ...................... 436/518 |
| 4,877,745 | 10/1989 | Hayes et al. ........................... 436/166 |
| 5,021,236 | 6/1991 | Gries et al. ................................ 424/9 |
| 5,087,556 | 2/1992 | Ertinghausen ......................... 435/7.9 |
| 5,112,134 | 5/1992 | Chow et al. ........................... 356/427 |
| 5,118,605 * | 6/1992 | Urdea ........................................ 435/6 |
| 5,132,097 | 7/1992 | Van Deusen et al. ............. 422/82.09 |
| 5,164,319 | 11/1992 | Hafeman et al. ..................... 435/291 |
| 5,168,057 | 12/1992 | Oh et al. ................................ 435/174 |
| 5,278,048 | 1/1994 | Parce et al. ............................. 436/29 |
| 5,334,837 | 8/1994 | Ikeda et al. ............................ 250/339 |
| 5,345,213 | 9/1994 | Semancik et al. ...................... 338/34 |
| 5,384,261 | 1/1995 | Winkler et al. ....................... 436/518 |
| 5,405,783 | 4/1995 | Pirrung et al. ........................ 436/518 |
| 5,412,087 | 5/1995 | McGall et al. ....................... 536/24.3 |
| 5,424,186 | 6/1995 | Fodor et al. .............................. 435/6 |
| 5,429,807 | 7/1995 | Matson et al. ........................ 422/131 |
| 5,445,934 | 8/1995 | Fodor et al. .............................. 435/6 |
| 5,462,839 | 10/1995 | deRooji et al. ....................... 430/320 |
| 5,489,678 | 2/1996 | Fodor et al. ......................... 536/22.1 |
| 5,510,270 | 4/1996 | Fodor et al. ........................... 436/518 |
| 5,521,289 * | 5/1996 | Hainfeld et al. .................... 530/391.5 |
| 5,580,696 | 12/1996 | Yashiro ........................... 430/270.17 |
| 5,599,662 | 2/1997 | Respess .................................... 435/5 |
| 5,624,711 | 4/1997 | Sundberg et al. ................... 427/261 |
| 5,892,577 | 4/1999 | Gordon .................................... 356/73 |
| 6,030,581 | 2/2000 | Virtanen .............................. 422/68.1 |
| B1 3,654,090 | 7/1982 | Schuurs et al. ........................... 435/7 |
| B1 4,366,241 | 12/1982 | Tom et al. ................................. 435/7 |

FOREIGN PATENT DOCUMENTS

| | | | |
|---|---|---|---|
| WO 98/01533 | 1/1998 | (WO) . | |
| WO 98/07019 | 2/1998 | (WO) | ............................. G01N/21/07 |
| WO 98/12559 | 3/1998 | (WO) . | |
| WO 98/12356 | 4/1998 | (WO) . | |
| WO 98/28623 | 7/1998 | (WO) | ............................. G01N/33/543 |
| WO 98/37238 | 8/1998 | (WO) | ............................... C12Q/1/68 |
| WO 98/38510 | 9/1998 | (WO) | ............................. G01N/33/487 |
| WO 99/35499 | 7/1999 | (WO) | ............................. G01N/33/543 |

OTHER PUBLICATIONS

Fodor, S.P.A. et al., "Multiplexed Biochemical Assays with Biological Chips," *Nature*, 364(6437):555–556 (1993).

Given, A.L., *Flow Cytometry, First Principles*, Wiley–Liss, New York, N.Y. (1992).

Gosling, J.P. et al. (eds), *Immunoassay: Laboratory Analysis and Clinical Applications*, Butterworth–Heinemann, Newton, Massachusetts (1994).

Green, F.J., *The Sigma–Aldrich Handbook of Stains, Dyes and Indicators*, Aldrich Chemical Company Inc., Milwaukee, Wisconsin (1991).

Hayat, M.A. (ed.), *Immunogold–Silver Staining*, CRC Press (1995).

Jackman, R.J. et al., "Fabrication of Submicrometer Features on Curved Substrates by Microcontact Printing," *Science*, 269:664–666 (1995).

Law, B. (ed.), *Immunoassay, A Practical Guide*, Taylor & Francis, Great Britain (1996).

Nilsson, M. et al., "Padlock Probes: Circularizing Oligonucleotides for Localized DNA Detection," *Science*, 265:2085–2088 (1994).

Robinson, J.P. (ed.), *Handbook of Flow Cytometry Methods*, Wiley–Liss, New York, N.Y. (1993).

Szathmary, E., "The First Two Billion Years," *Nature*, 387 (6634):662–663 (1997).

* cited by examiner

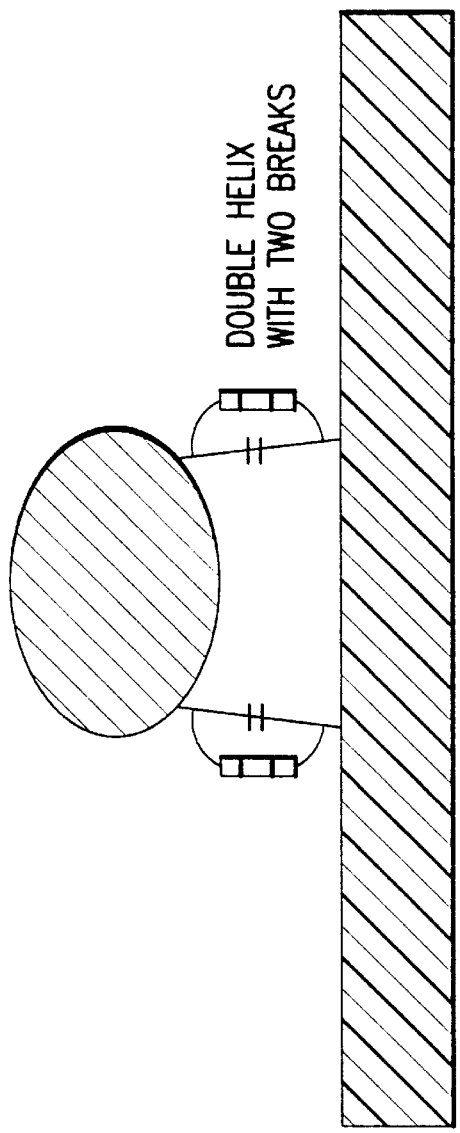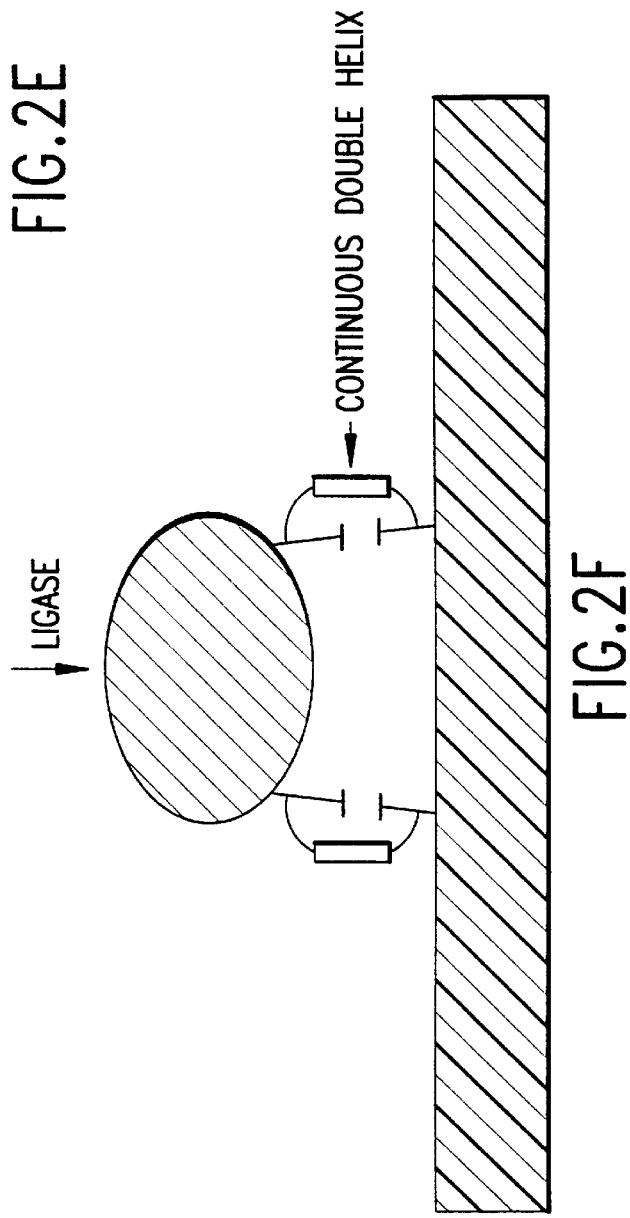

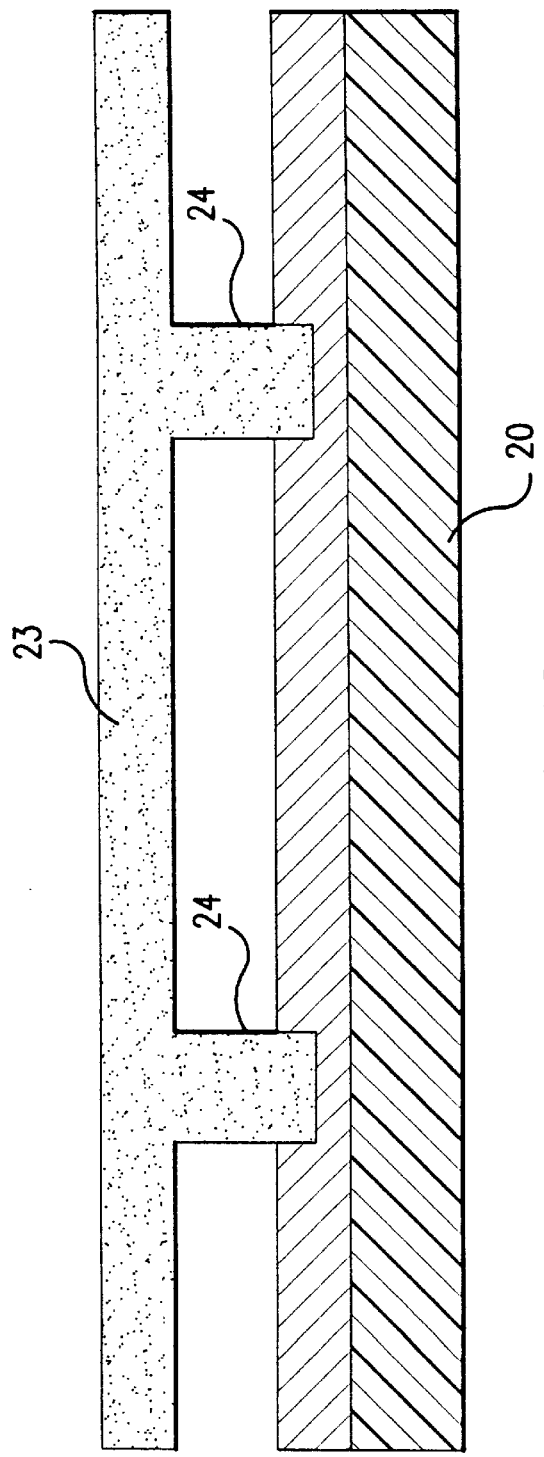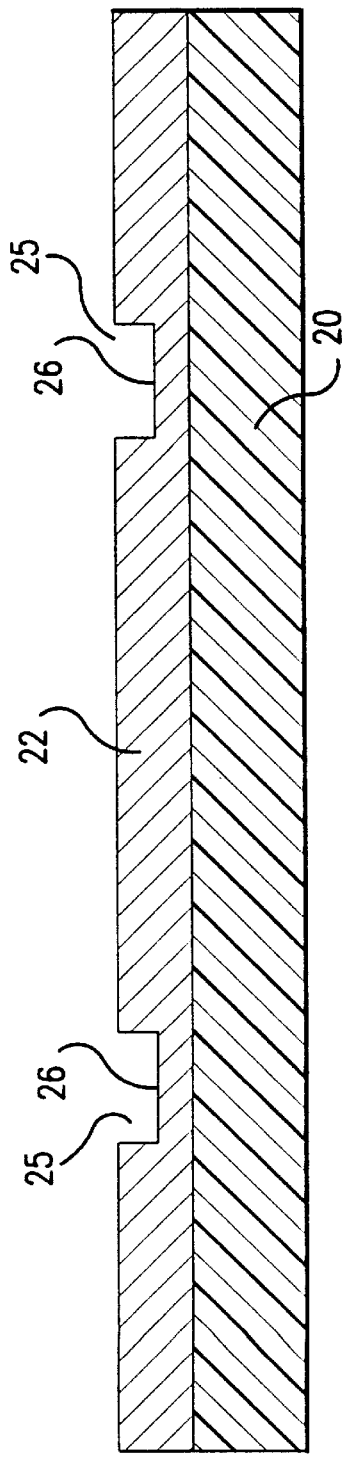

SPATIALLY ADDRESSABLE, CLEAVABLE REFLECTIVE SIGNAL ELEMENTS, ASSAY DEVICE AND METHOD

CROSS-REFERENCE TO RELATED APPLICATIONS

The present application is a continuation of U.S. patent application Ser. No. 08/888,935, filed on Jul. 17, 1997 now abandoned, which is a continuation-in-part of U.S. provisional application Ser. No. 60/021,367, filed Jul. 8, 1996 and U.S. provisional application Ser. No. 60/030,416, filed Nov. 1, 1996, incorporated herein by reference.

1. INTRODUCTION

The present invention relates to the field of diagnostics and the detection of small quantities of substances in fluids. More specifically, the invention relates to a cleavable signal element, particularly a cleavable reflective signal element, for use in assay devices. The assay devices employing such signal elements are, in preferred embodiments of the invention, adapted for detection using standard laser-based detection systems, such as CD-ROM readers, DVD readers, and the like. The invention further includes analytical methods for detecting analytes using the assay devices of the present invention. The signalling element, assay devices and assay methods of the present invention are useful both for the detection of a large number of different analytes in a test sample and the detection of a single analyte in a large number of samples.

2. BACKGROUND OF THE INVENTION

2.1 Small Scale Clinical Assays

Until recently, most clinical diagnostic assays for the detection of small quantities of analytes in fluids have been conducted as individual tests; that is, as single tests conducted upon single samples to detect individual analytes. More recently, efficiency and economy have been obtained by designing apparatus for multi-sample preparation and automated reagent addition, and by designing apparatus for rapid analysis of large numbers of test samples, either in parallel or in rapid serial procession. Often, such automated reagent preparation devices and automated multiplex analyzers are integrated into a single apparatus.

Large clinical laboratory analyzers of this type can accurately perform hundreds of assays automatically, or semi-automatically, in one hour. However, these analyzers are expensive and only centralized laboratories and large hospitals can afford them. Such centralization necessitates sample transport, and often precludes urgent or emergent analysis of time-critical samples.

Thus, there exists a strong need for simplified clinical assays that will both reduce the cost of such dedicated analyzers and further their distribution. The limit of such effort is the design of clinical tests suitable for use at the patient bedside or in the patient's home without dedicated detectors. Blood glucose and pregnancy tests are well known examples.

Although useful tests of this sort have been offered for many years, a major breakthrough was the introduction of solid phase immunoassays and other strip tests since approximately 1980. Most notable are Advance® test (Johnson & Jonson), RAMP™ hCG assay (Monoclonal Antibodies, Inc.), Clear Blue Easy™ (Unipath Ltd.) and ICON (Hybritech).

Clear Blue Easy™ has all reagents in a laminated membrane and uses conjugated colored latex microbeads as the signal reagent. It uses a capillary migration immunoconcentration format. The ICON is a dual monoclonal sandwich immunoconcentration assay. This assay has been rendered quantitative through the use of a small reflectance instrument. Otherwise, all these methods are only qualitative.

Migration distance can be used as a basis for quantitative assays. Commercially available are Quantab™ (Environmental Test Systems), AccuLevel® (Syva), Accu-Meter® (ChemTrak), Clinimeter™ (Crystal Diagnostics) and Q.E.D.™ (Enzymatics). One of the newest is a thermometer-type assay device (Ertinghausen G., U.S. Pat. No. 5,087,556) that is not yet commercially available. These systems can be used to assay general chemistry analytes, such as cholesterol, as well as blood levels of therapeutic drugs.

One disadvantage, however, of each of these formats is that only one, or a very limited number, of assays can conveniently be performed simultaneously.

To fill the gap between massive analyzers and strips, some small instruments have been developed. The most notable is Eclipse ICA™ (Biotope, Inc.). This device is a bench-top, random-access, automated centrifugal immunoassay and chemistry system. Patient samples are pipetted into cassettes that are placed into a rotor. Sixteen tests can be run in approximately 17 minutes. The results are measured by UV/Visual spectrometry or by fluorometry. Four different types of cassette are needed. Each cassette has a relatively complicated structure.

Despite these developments, there still exists a need for a simple device that can easily be used for multiple quantitative assays, and preferably requiring no specialized detector instrumentation.

2.2 Spatially-Addressable Probe Arrays

Recently, spatially addressable arrays of different biomaterials have been fabricated on solid supports. These probe arrays permit the simultaneous analysis of a large number of analytes. Examples are arrays of oligonucleotides or peptides that are fixed to a solid support and that capture complementary analytes. One such system is described by Fodor et al., Nature, Vol. 364, Aug. 5, 1993. Short oligonucleotide probes attached to a solid support bind complementary sequences contained in longer strands of DNA in liquid sample; the sequence of the sample nucleic acids is then calculated by computer based on the hybridization data so collected.

In the assay system described by Fodor et al., the array is inverted on a temperature regulated flow cell against a reservoir containing the tagged target molecules. In order to distinguish the surface bound molecules, the system requires an extremely sensitive detector.

Accordingly, there remains a need for an economical system to fabricate spatially addressable probe arrays in a simplified format that provides both for ready detection and the ability to assay for large numbers of test substances (i.e. analytes) in a fluid test sample in a single step, or a minimum number of steps, or assay for a single test substance or analyte in a large number of fluid test samples.

2.3 Spatially Addressable Laser-Based Detection Systems

Several devices for consumer electronic use permit spatially addressable detection of digital information. In particular, several formats have been developed based on the information recording potential of differential reflectance and transmittance.

In conventional audio or CD-ROM compact disks, digital information—or digitally encoded analog information—is encoded on a circular plastic disk by means of indentations in the disk. Typically, such indentations are on the order of one-eighth to one-quarter of the wavelength of the incident beam of a laser that is used to read the information present on the disk. The indentations on the disk cause destructive interference within the reflected beam, which corresponds to a bit having a "zero" value. The flat areas of the disk reflect the laser light back to a detector and the detector gives a value of "one" to the corresponding bit.

In another convention, a change of intensity of a reflected light gets a value of one while a constant intensity corresponds to zero.

Since the indentations have been formed in the disk in a regular pattern from a master copy containing a predetermined distribution of bits of "zero" and bits of "one", the resultant signal received by the detector is able to be processed to reproduce the same information that was encoded in the master disk.

The standard compact disk is formed from a 12 cm polycarbonate substrate, a reflective metalized layer, and a protective lacquer coating. The format of current CDs and CD-ROMs is described by the ISO 9660 industry standard, incorporated herein by reference.

The polycarbonate substrate is optical-quality clear polycarbonate. In a standard pressed, or mass-replicated CD, the data layer is part of the polycarbonate substrate, and the data are impressed in the form of a series of pits by a stamper during the injection molding process. During this process, molten polycarbonate is injected into a mold, usually under high pressure, and then cooled so that the polycarbonate takes on the shape of the mirror image of the mold, or "stamper" or "stamp"; pits that represent the binary data on a disc's substrate are therefore created in and maintained by the polycarbonate substrate as a mirror image of the pits of the stamper created during the mastering process. The stamping master is typically glass.

Pits are impressed in the CD substrate in a continuous spiral. The reflective metal layer applied thereupon, typically aluminum, assumes the shape of the solid polycarbonate substrate, and differentially reflects the laser beam to the reading assembly depending on the presence or absence of "pits." An acrylic lacquer is spincoated in a thin layer on top of the metal reflective layer to protect it from abrasion and corrosion.

Although similar in concept and compatible with CD readers, the information is recorded differently in a recordable compact disk (CD-R). In CD-R, the data layer is separate from the polycarbonate substrate. The polycarbonate substrate instead has impressed upon it a continuous spiral groove as an address for guiding the incident laser. An organic dye is used to form the data layer. Although cyanine was the first material used for these discs, a metal-stabilized cyanine compound is generally used instead of "raw" cyanine. An alternative material is phthalocyanine. One such metallophthalocyanine compound is described in U.S. Pat. No. 5,580,696.

In CD-R, the organic dye layer is sandwiched between the polycarbonate substrate and the metalized reflective layer, usually 24 carat gold, but alternatively silver, of the media. Information is recorded by a recording laser of appropriate preselected wavelength that selectively melts "pits" into the dye layer—rather than burning holes in the dye, it simply melts it slightly, causing it to become non-translucent so that the reading laser beam is refracted rather than reflected back to the reader's sensors, as by a physical pit in the standard pressed CD. As in a standard CD, a lacquer coating protects the information-bearing layers.

Other physical formats for recording and storing information are being developed based on the same concept as the compact disk: creation of differential reflectance or transmittance on a substrate to be read by laser.

One such format is termed Digital Video Disc (DVD). A DVD looks like standard CD: it is a 120 mm (4.75 inch) disk that appears as a silvery platter, with a hole in the center for engaging a rotatable drive mechanism. Like a CD, data is recorded on the disc in a spiral trail of tiny pits, and the discs are read using a laser beam. In contrast to a CD, which can store approximately 680 million bytes of digital data under the ISO 9660 standard, the DVD can store from 4.7 billion to 17 billion bytes of digital data. The DVD's larger capacity is achieved by making the pits smaller and the spiral tighter, that is, by reducing the pitch of the spiral, and by recording the data in as many as four layers, two on each side of the disc.[1] The smaller pit size and tighter pitch require that the reading laser wavelength be smaller. While the smaller wavelength is backward compatible with standard pressed CDs, it is incompatible with current versions of the dye-based CD-R.

NOTE: mention multiple layers in the invention.

The following table compares DVD and CD Characteristics:

TABLE 1

Comparison of DVD and CD Characteristics

|  | DVD | CD |
| --- | --- | --- |
| Diameter | 120 mm | 120 mm |
| Disc Thickness | 1.2 mm | 1.2 mm |
| Substrate Thickness | 0.6 mm | 1.2 mm |
| Track pitch | 0.74 $\mu$m | 1.6 $\mu$m |
| Minimum pit size | 0.4 $\mu$m | 0.83 $\mu$m |
| Laser wavelength | 635/650 nm | 780 nm |
| Data capacity | 4.7 gigabytes/layer/side | 0.68 gigabytes |
| Layers | 1, 2, or 4 | 1 |

Thus, a single sided/single layer DVD can contain 4.7 GB of digital information. A single sided/dual layer DVD can contain 8.5 GB of information. A Dual sided/single layer disk can contain 9.4 GB of information, while a dual sided, dual layer DVD contains up to 17 GB of information.

Each of the variations consists of two 0.6 mm substrates that are bonded together. Depending on the capacity, the disc may have one to four information layers. In the 8.5 GB and 17 GB options, a semi-reflector is used in order to access two information layers from one side of the disc.

For the 8.5 GB DVD and 17 GB options, the second information layer per side may be molded into the second substrate or may be added as a photopolymer layer. In either case, a semi-reflector layer is required to allow both information layers to be read from one side of the disk. For the 17 GB DVD, it is necessary to produce two dual-layer substrates, and bond them together.

The DVD laser reader is designed to adjust its focus to either layer depth so that both of them can be quickly and automatically accessed.

All three of the above-described formats require that the platter be spun. The nominal constant linear velocity of a DVD system is 3.5 to 4.0 meters per second (slightly faster for the larger pits in the dual layer versions), which is over 3 times the speed of a standard CD, which is 1.2 mps.

3. SUMMARY OF THE INVENTION

It is one aspect of the present invention to provide a cleavable signal element for use in quantitative and qualitative assay devices and methods.

The cleavable signal element comprises a cleavable spacer having a substrate-attaching end, a signal-responsive end, and a cleavage site intermediate the substrate-attaching end and the signal-responsive end. The cleavable signal element further includes a signal responsive moiety attached to the cleavable spacer at its signal responsive end.

A first side member adapted to bind a first site on a chosen analyte, and a second side member adapted to bind a second site of the same analyte, are present on the signal element. The first and second side members confer analyte specificity upon the cleavable signal element.

The first side member is attached to the cleavable spacer intermediate said signal responsive end and said cleavage site, and the second side member is attached to the cleavable spacer intermediate said cleavage site and said substrate attaching end.

Binding of the chosen analyte simultaneously to the first and second side members of a cleavable signal element tethers the signal-responsive moiety to the signal element's substrate-attaching end, despite subsequent cleavage at the cleavage site that lies intermediate the first and second side members; conversely, failure to bind the chosen analyte simultaneously to the first and second side members of a cleavable signal element permits loss, through cleavage, of that signal element's signal-responsive moiety. The presence or absence of signal after contact with sample and contact with cleavage agent signals the presence or absence of analyte, respectively.

In another aspect, the invention provides an assay device comprising a solid support substrate to which a plurality of cleavable signal elements is attached in a spatially addressable pattern. In some embodiments of the assay device, the solid support may preferably be a plastic, and in these embodiments, is most preferably polycarbonate. The solid support in some embodiments is fashioned as a disk, preferably in dimensions compatible with detection by existing laser reflection-based detectors, such as an audio compact disk (CD) reader, a compact disk-read only memory (CD-ROM) reader, a digital video disk (DVD) reader, or the like.

In certain preferred embodiments of the assay device, the signal responsive moiety of the attached cleavable signal elements is adapted to reflect or scatter incident light, particularly incident laser light. In these cleavable reflective signal element embodiments, the signal responsive moiety may be a metal microsphere, preferably a microsphere consisting essentially of gold, most preferably a gold microsphere of diameter between 1–3 $\mu$m. These embodiments are suitable for detection in existing laser reflectance-based devices, such as audio CD, CD-ROM or DVD readers.

Another aspect of the present invention is to adapt existing assay methods to employ the cleavable signal element-based assay devices of the invention. Generally, an assay adapted to use the cleavable signal element-based assay device of the present invention comprises the steps of: contacting the assay device with a liquid sample, contacting the assay device with a cleaving agent adapted to cleave said plurality of attached cleavable signal elements, removing signal responsive ends of said cleaved signal elements, and detecting the presence of the signal responsive moiety of analyte-restrained cleaved signal elements adherent to the solid support substrate.

The spatial addressability of signal elements on the assay device permits identification of analytes bound to distinct signal elements, including identification of multiple analytes in a single assay.

The invention thus provides, in one embodiment, nucleic acid hybridization assays, in which the first and second side elements of the cleavable signal elements include oligonucleotides. Simultaneous binding of a nucleic acid present in the assay sample to the first and second side elements of the cleavable signal element prevents loss, through cleavage, of the signal element's signal-responsive end.

In another aspect, the invention provides an assay device comprising cleavable signal elements responsive to a plurality of nucleic acid sequences. This aspect of the invention provides a device and method suitable for sequencing nucleic acid through the spatial addressability of signals generated upon contact with a sample containing nucleic acid.

The invention further provides immunoassays. In these embodiments, the specificity-conferring side elements of the cleavable signal elements include antibodies, antibody fragments, or antibody derivatives. Simultaneous binding of an analyte to the antibody of the first side element and the antibody of the second side element prevents the loss, through cleavage, of the signal element's signal-responsive end.

In another aspect, the invention provides assay devices that comprise a solid support substrate to which is attached a plurality of cleavable signal elements and upon which is also encoded digital information in the form of computer software.

4. BRIEF DESCRIPTION OF THE DRAWINGS

The invention will be better understood by reference to the following drawings in which:

FIGS. 2D–2E are schematic representations of one aspect of the invention in which a soluble oligonucleotide added to the test sample increases sensitivity in a nucleic acid hybridization assay;

Figure 3A:
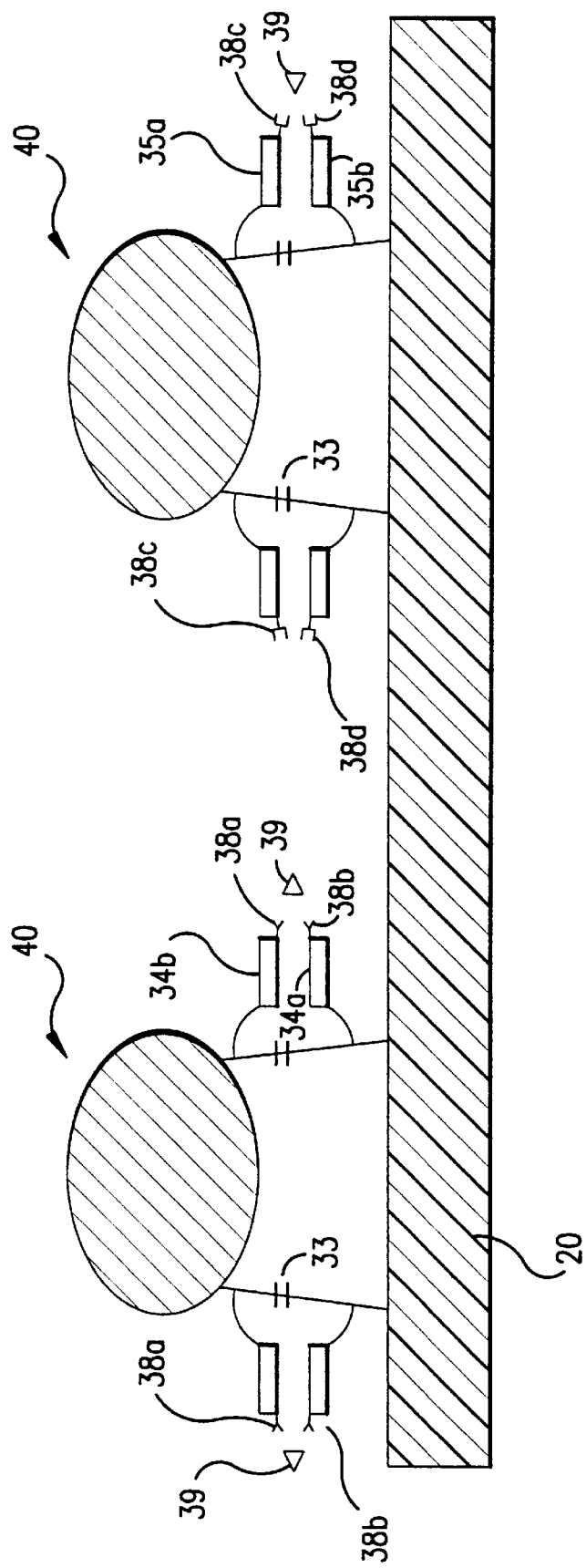
Figure 3B:
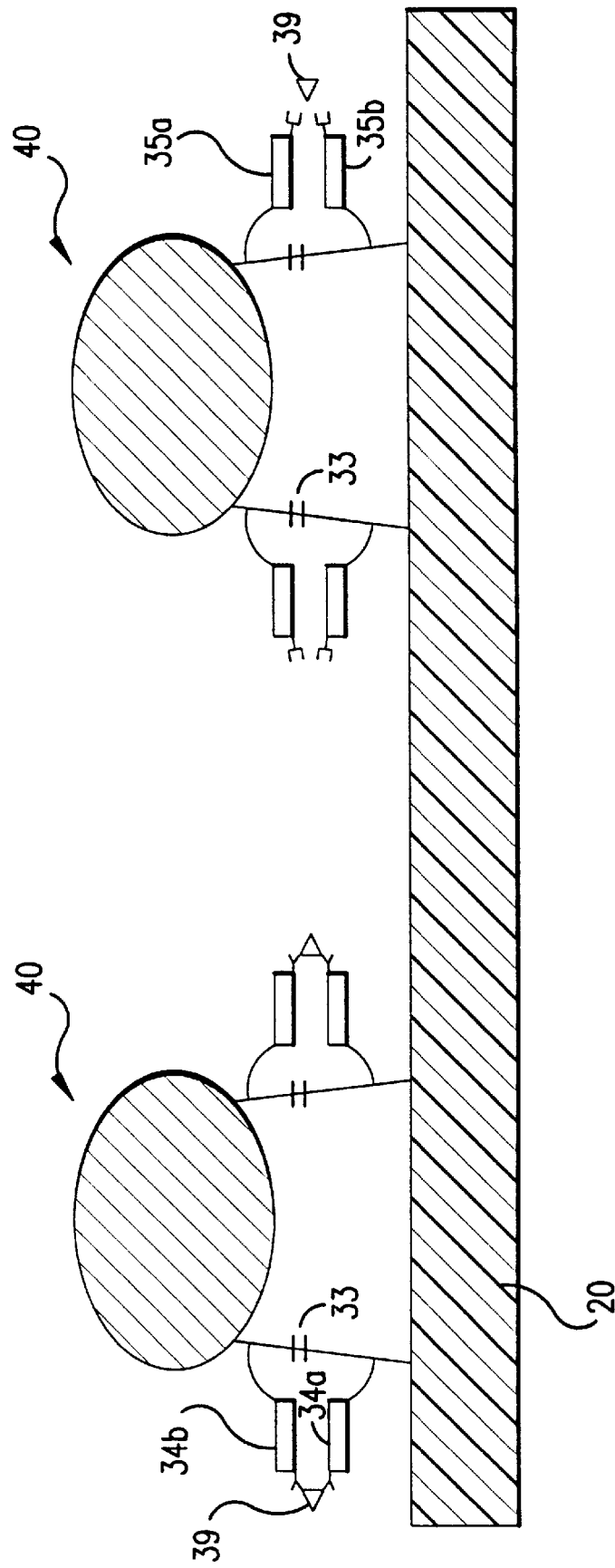
Figure 3C:
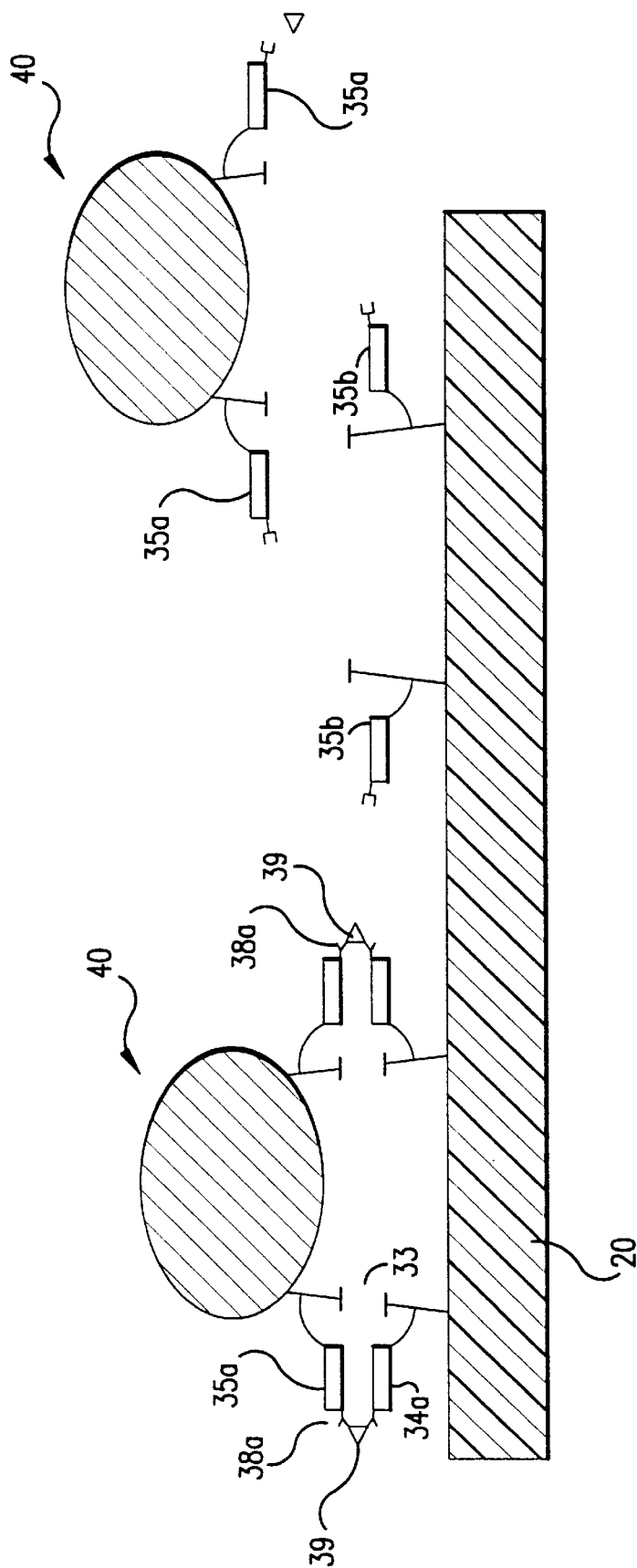
Figures 5, 6:
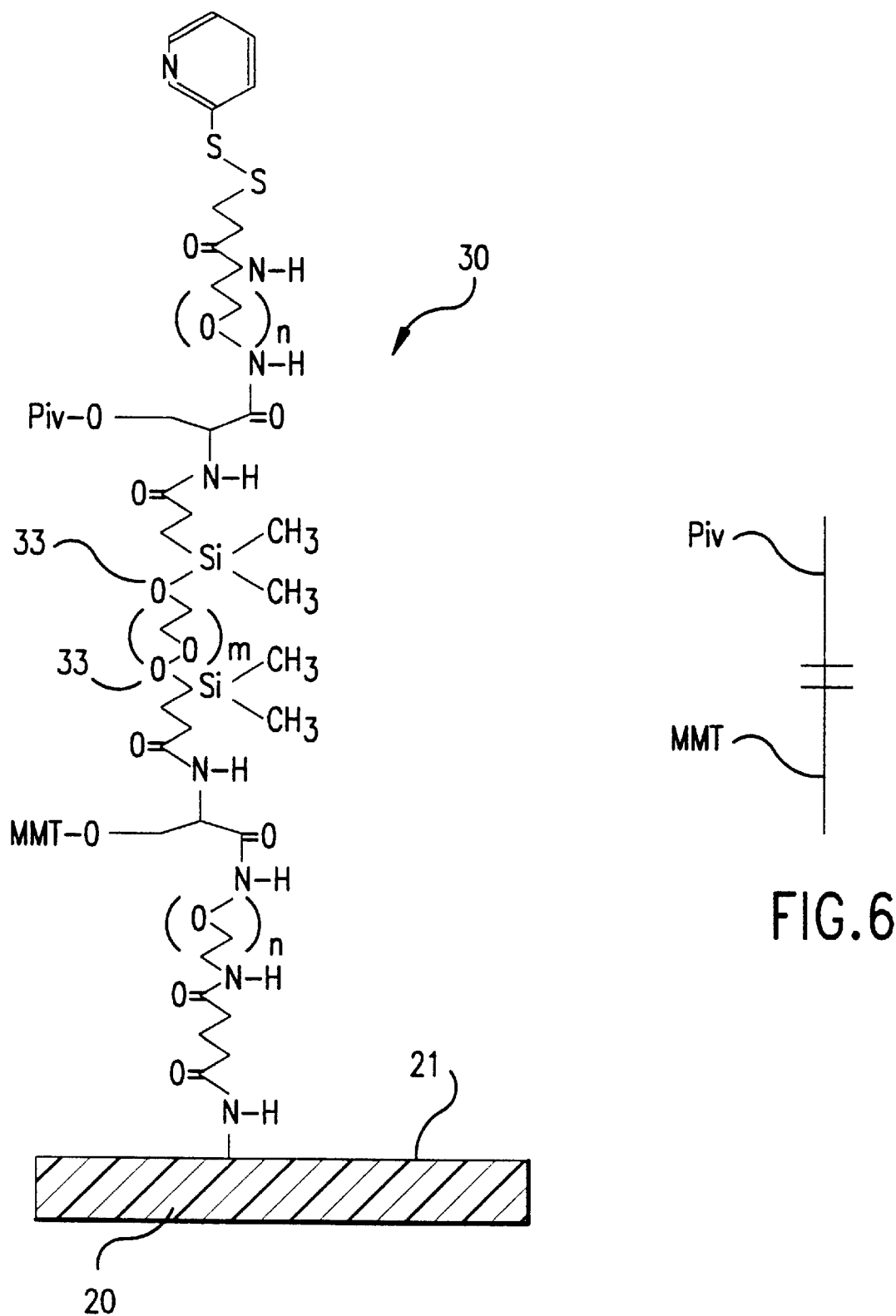
Figure 7A:
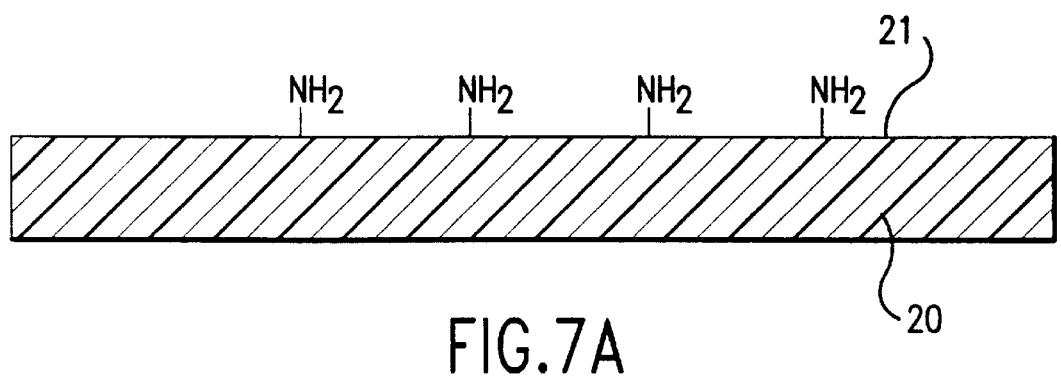
Figure 7B:
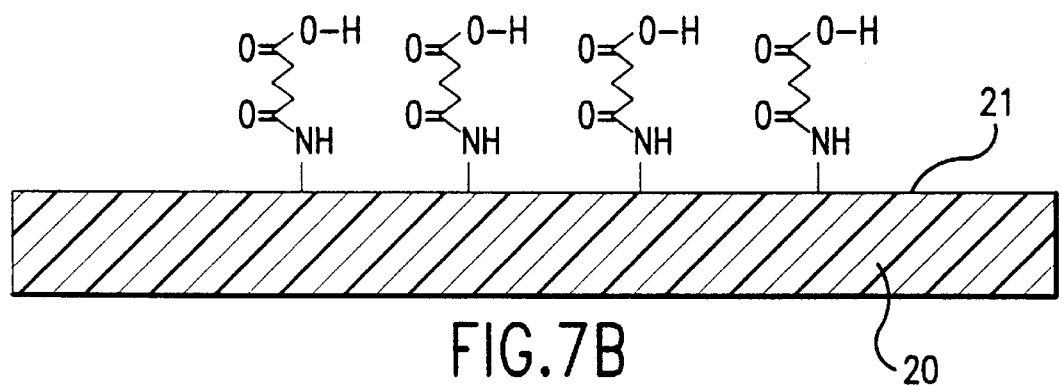
Figure 7C:
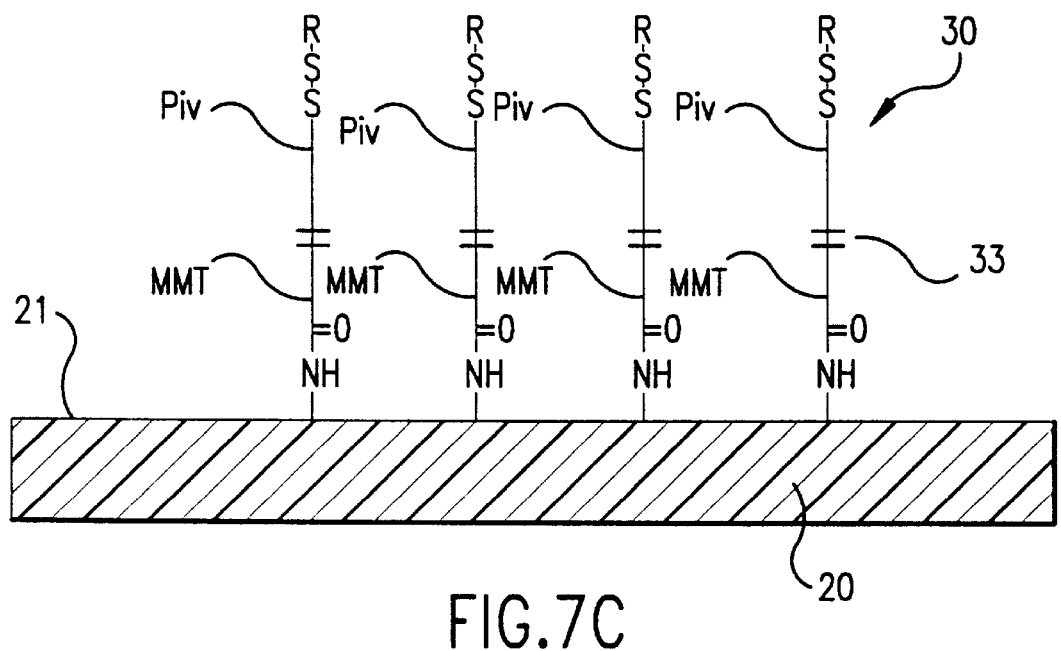
Figure 8A:
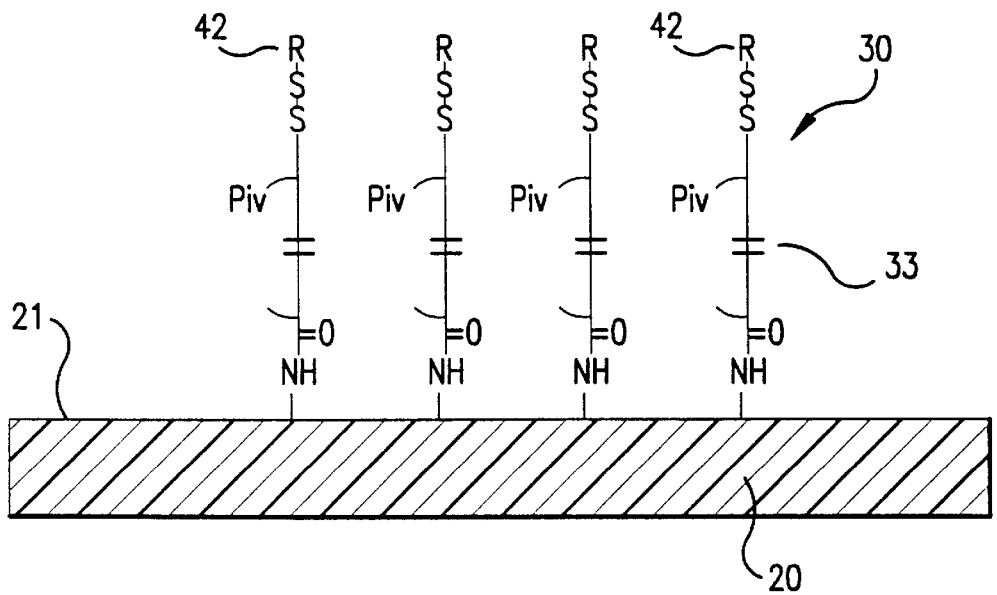
Figure 8B:
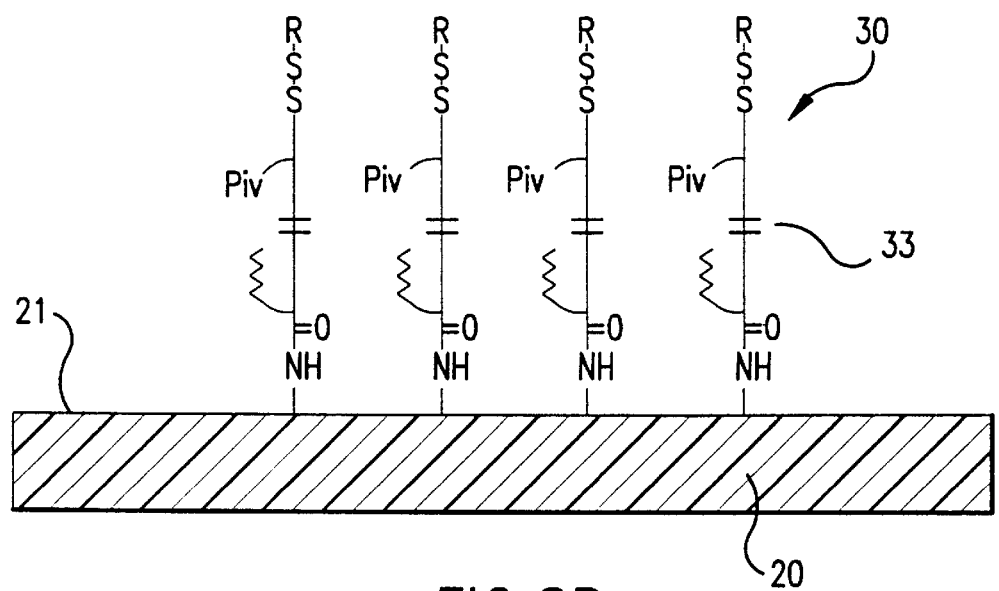
Figure 9A:
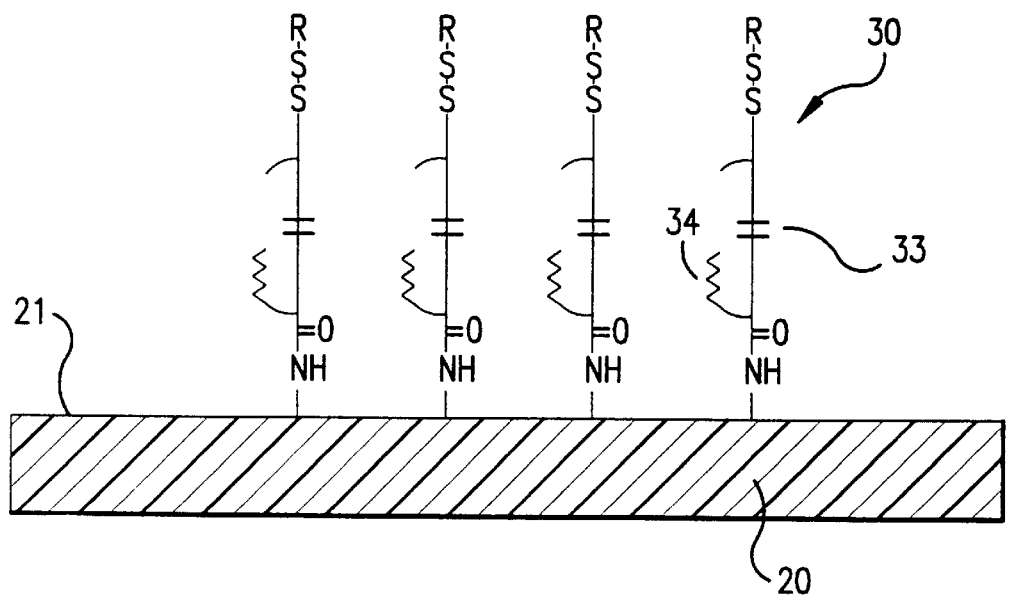
Figure 9B:
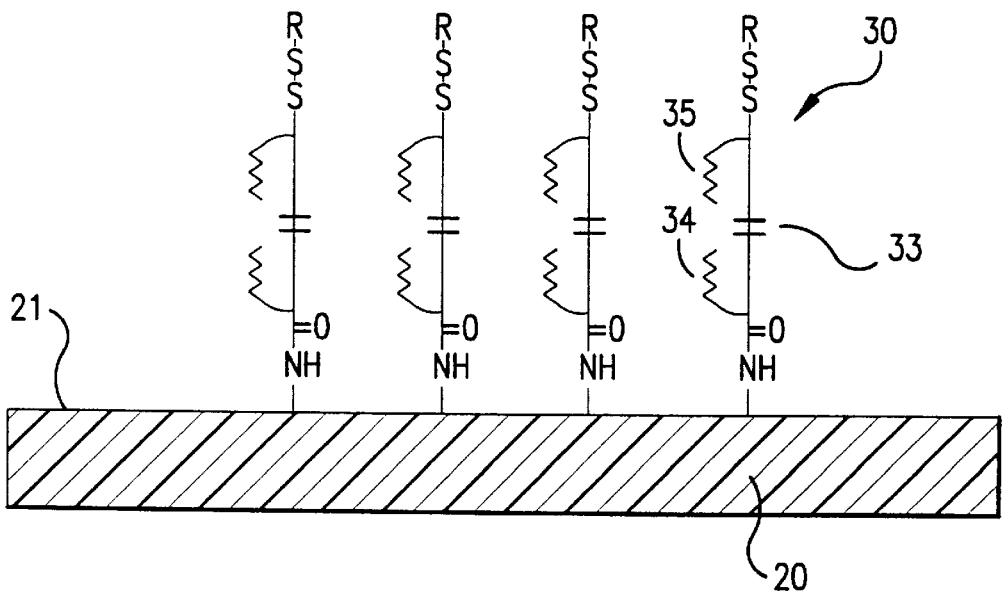
Figure 10A:
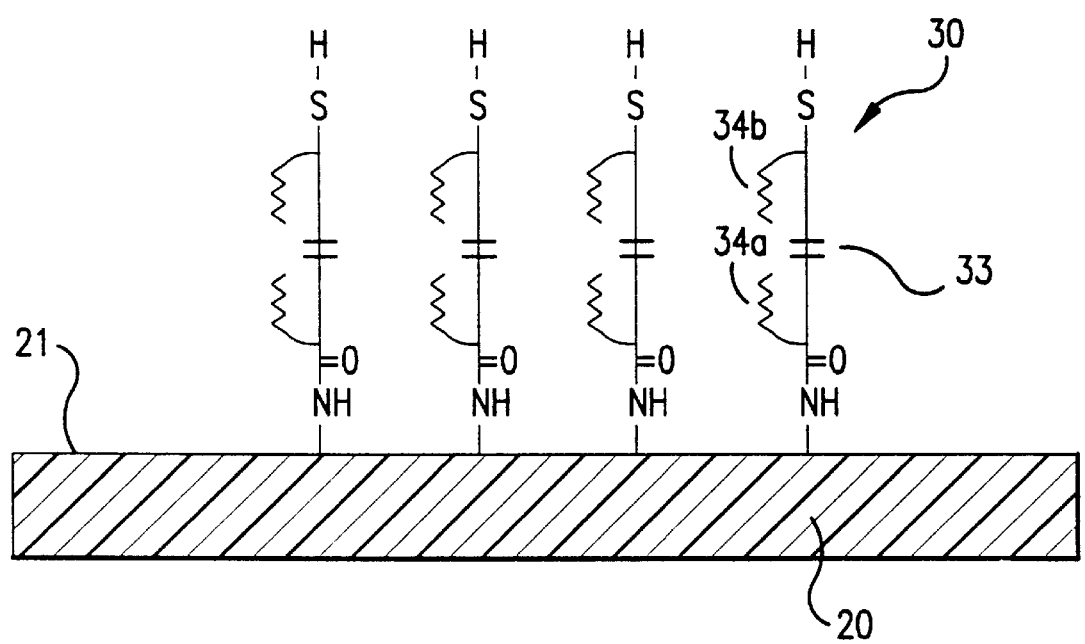
Figure 10B:
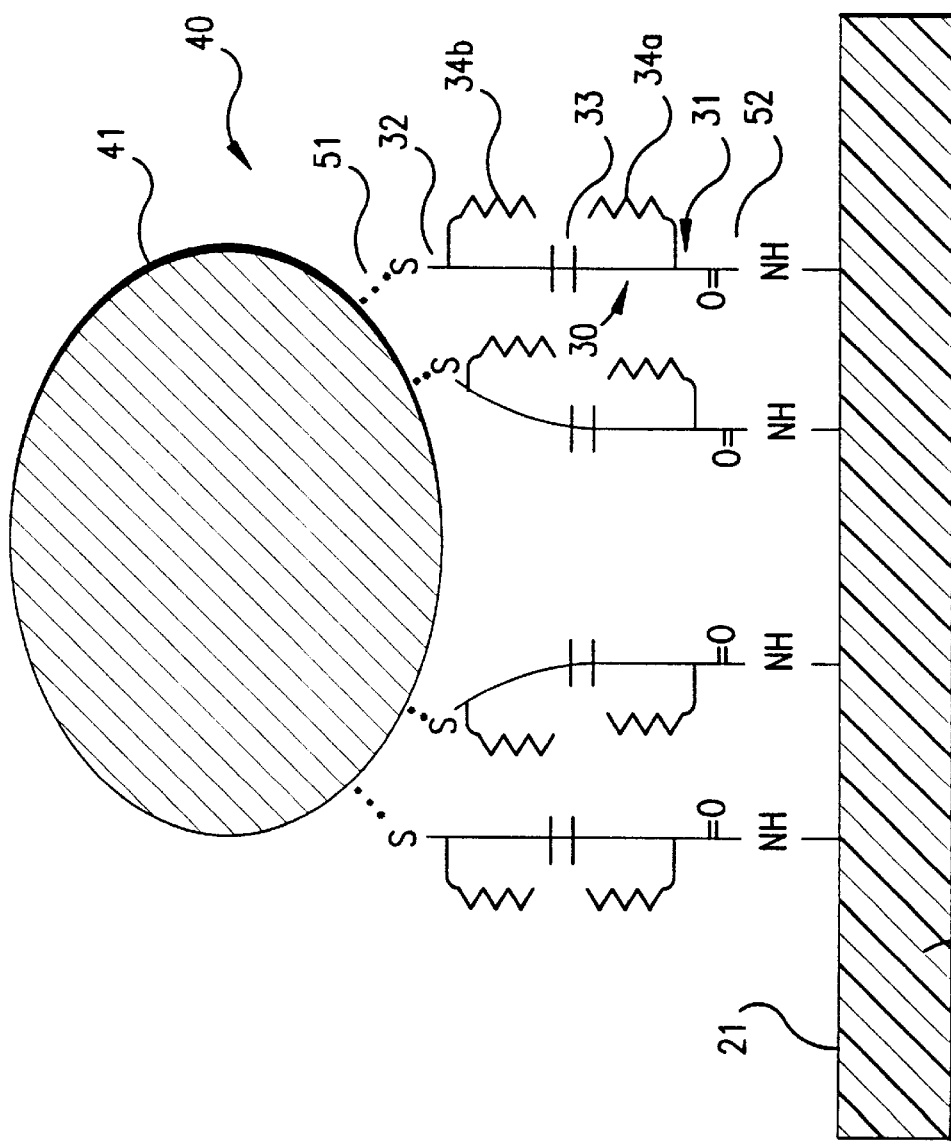
Figure 11A:
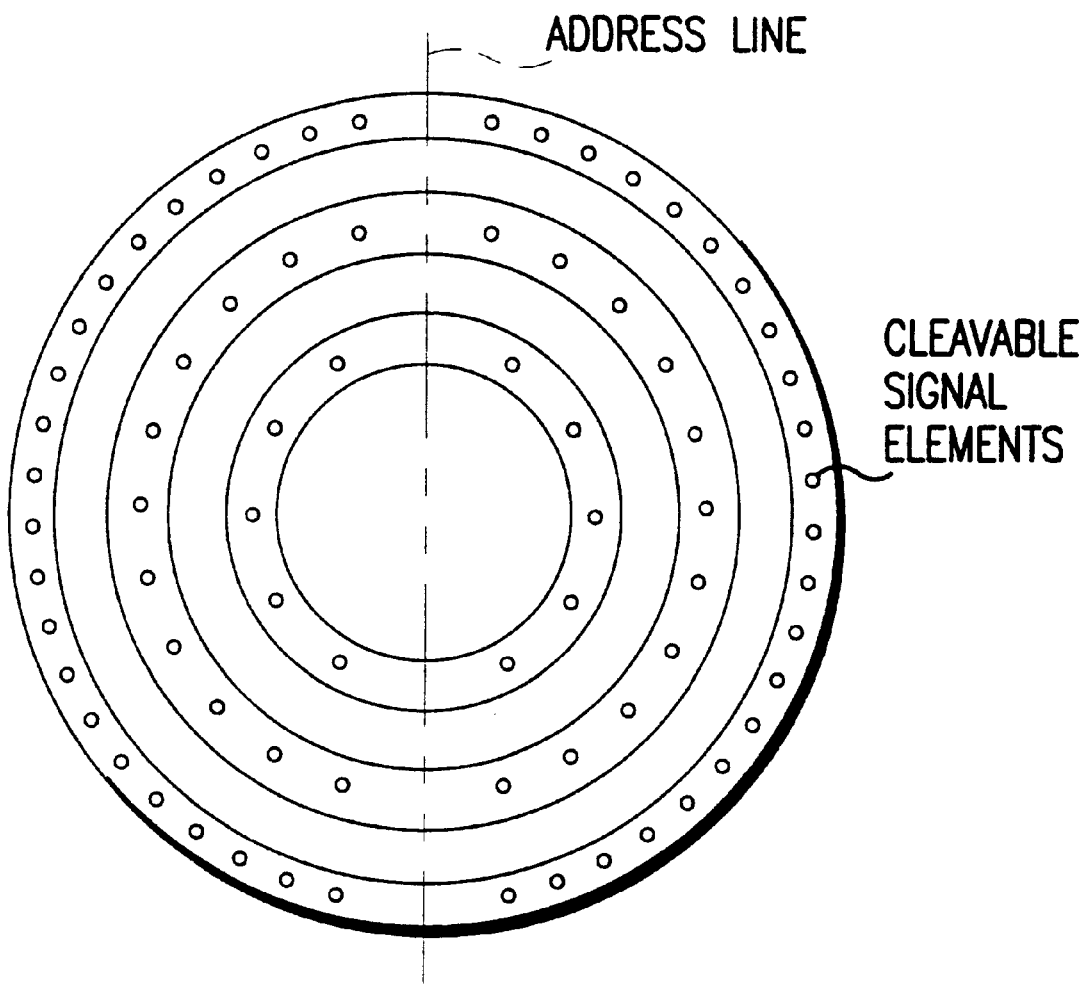
Figure 11B:
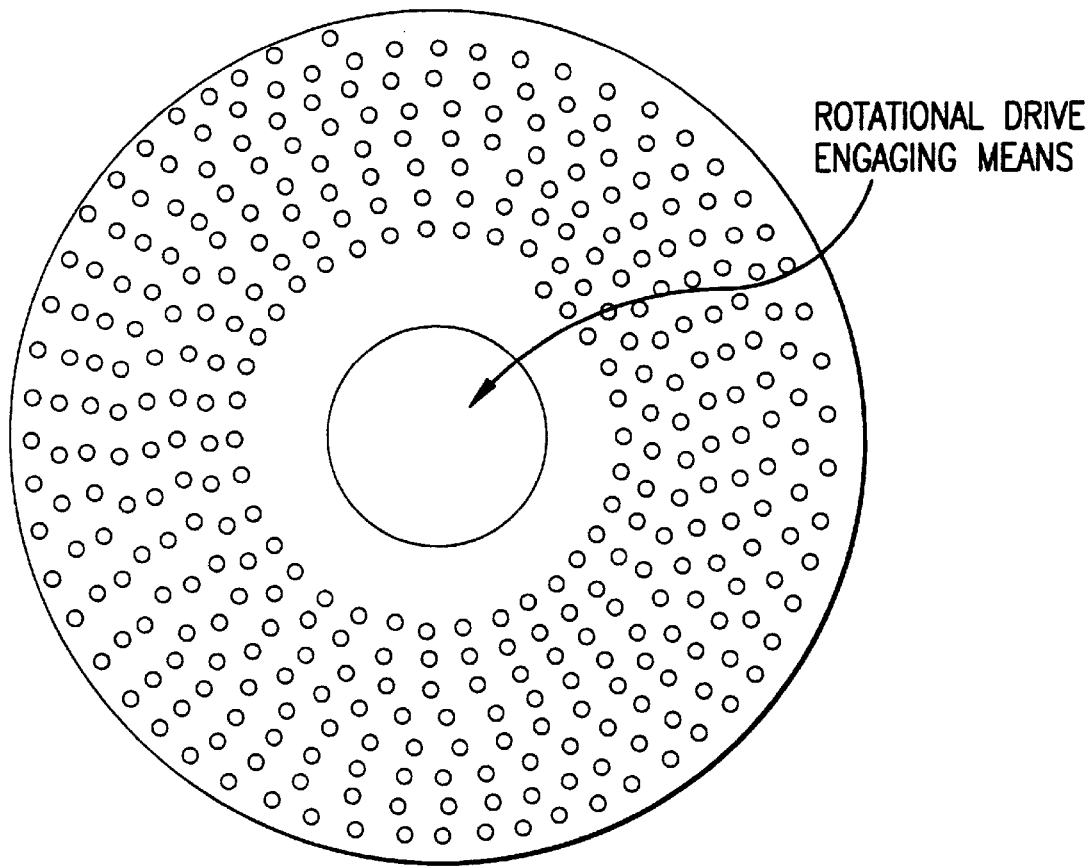
Figure 11C:
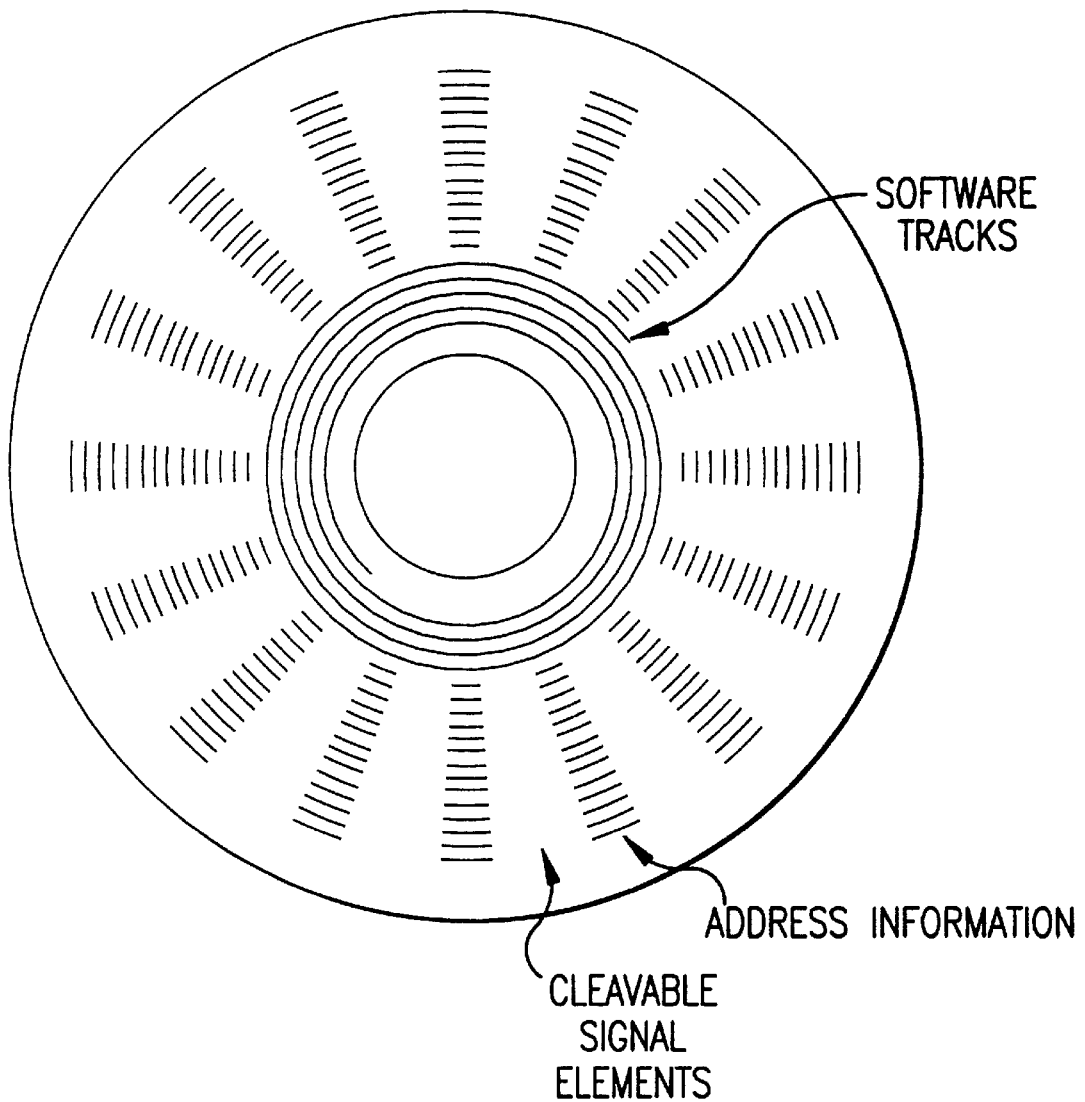
Figure 11D:
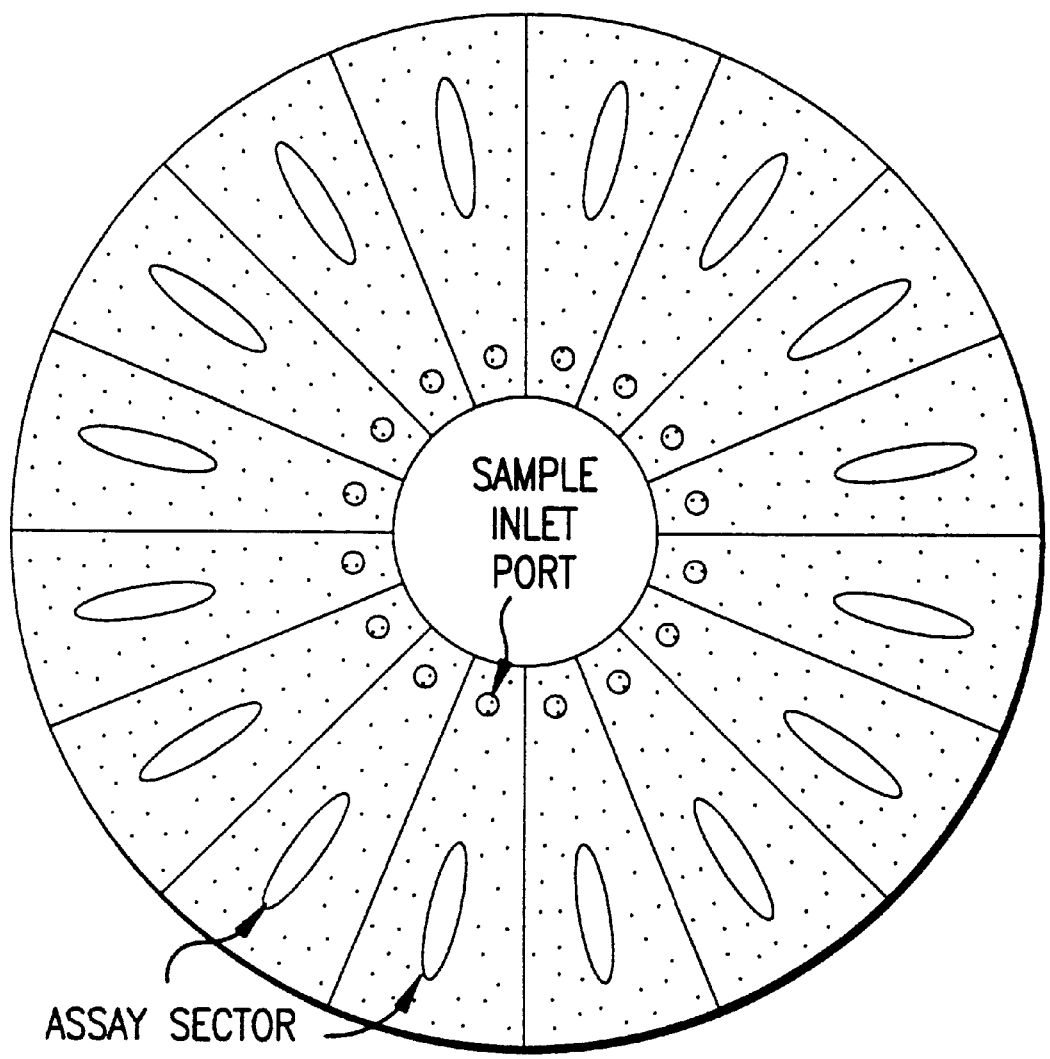
Figure 11E:
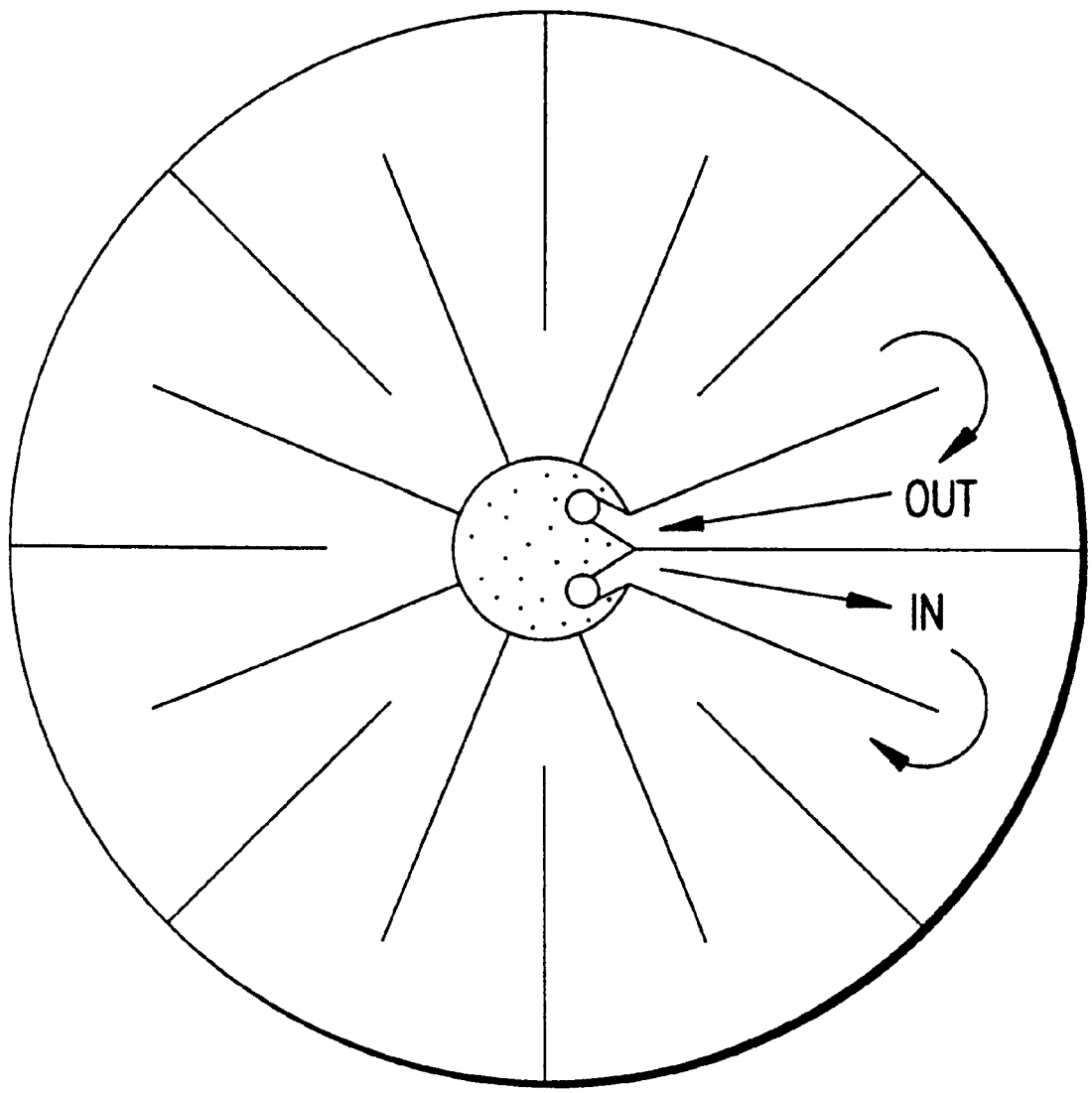
Figure 11F:
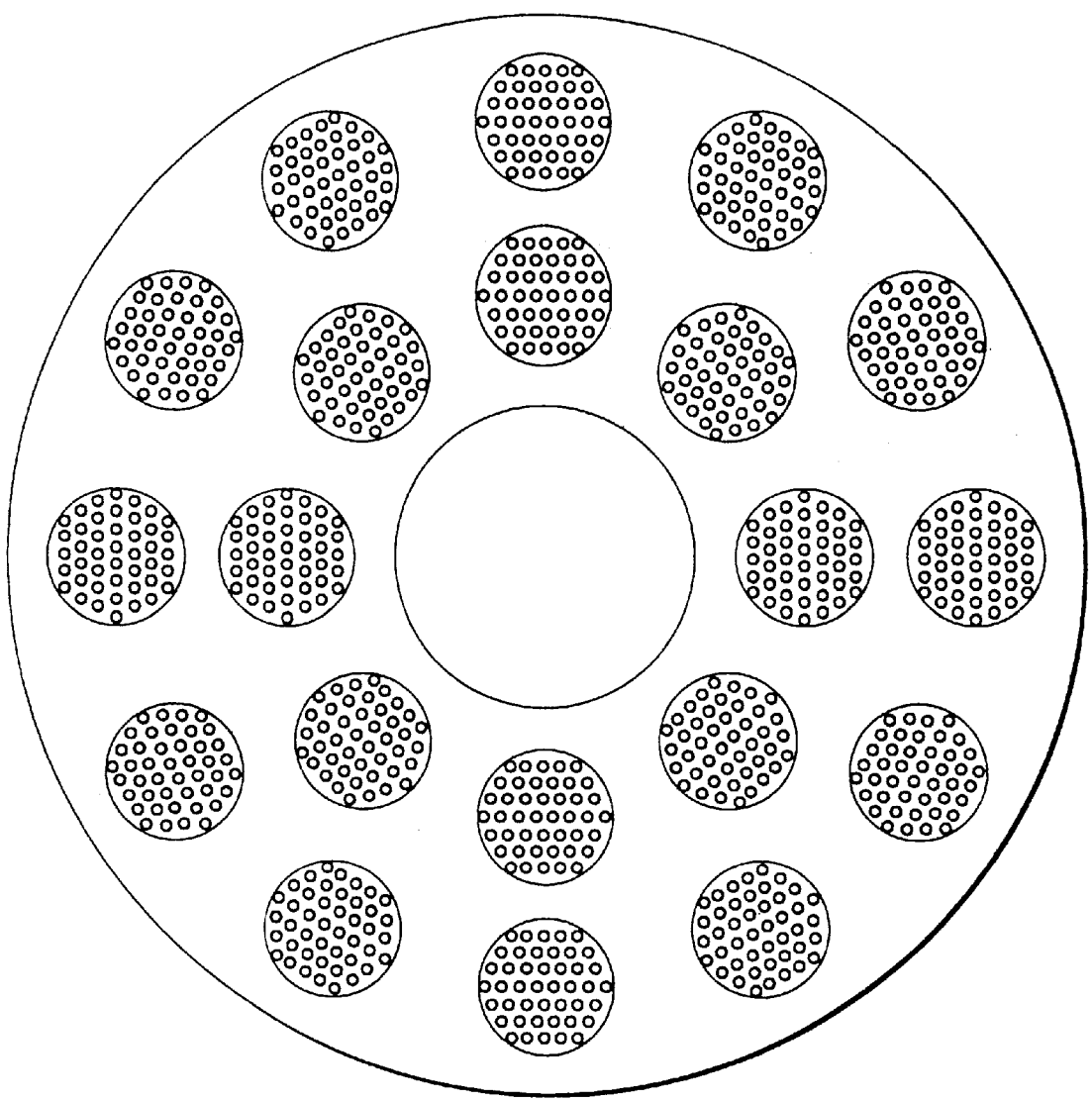
Figure 11G:
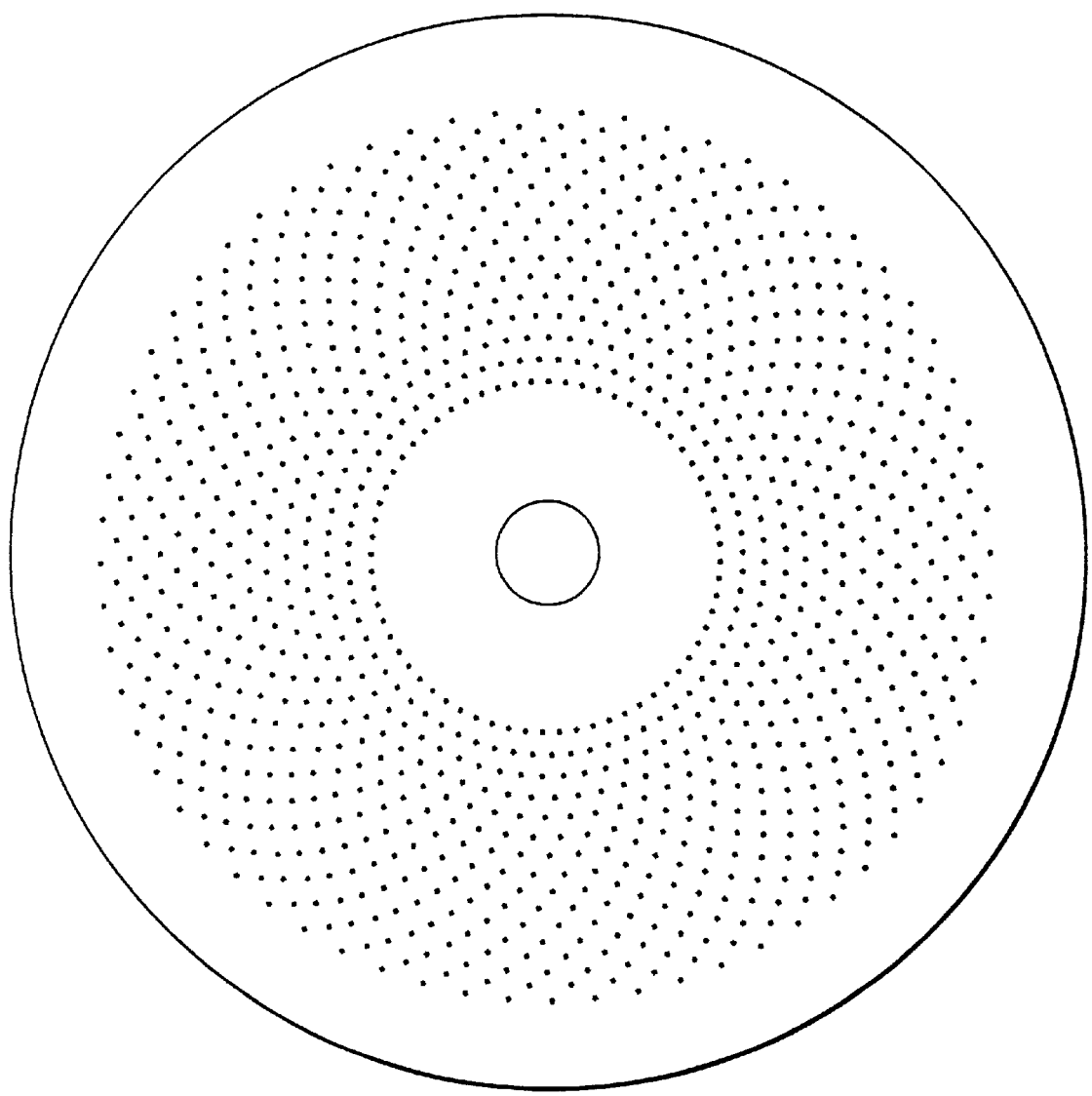
Figure 12:
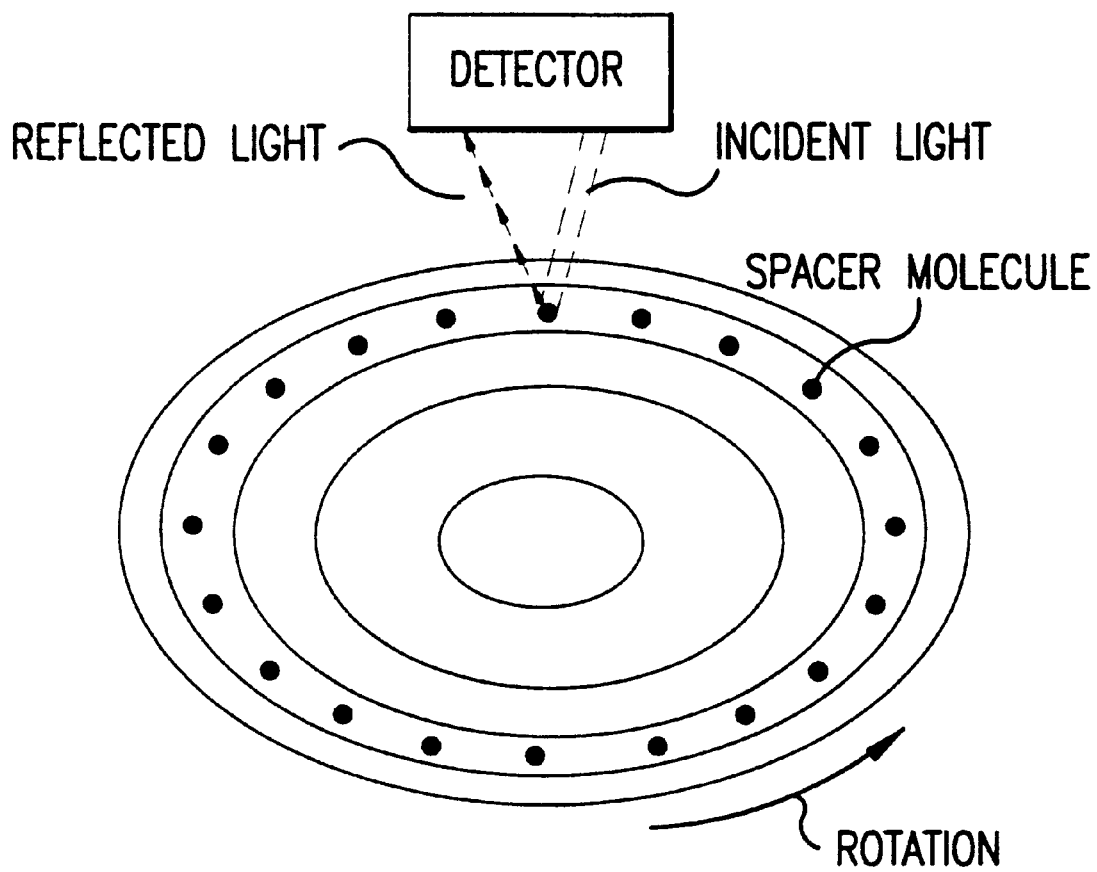
Figure 13A:
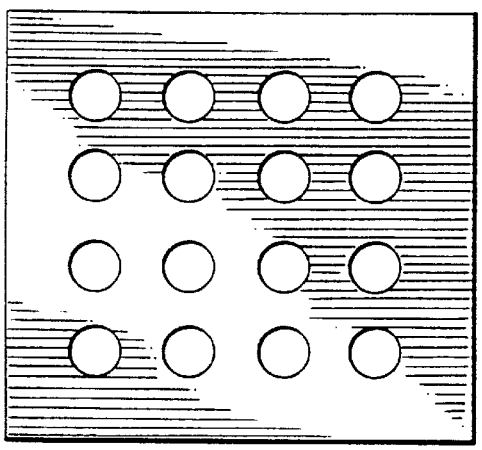
Figure 13C:
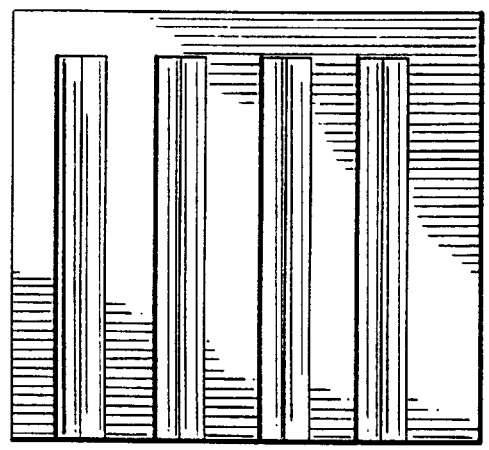
Figure 13B:
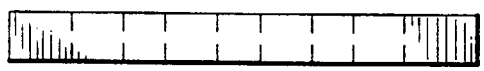
Figure 13D:
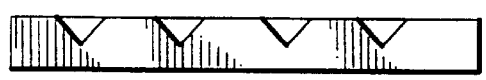
Figure 13E:
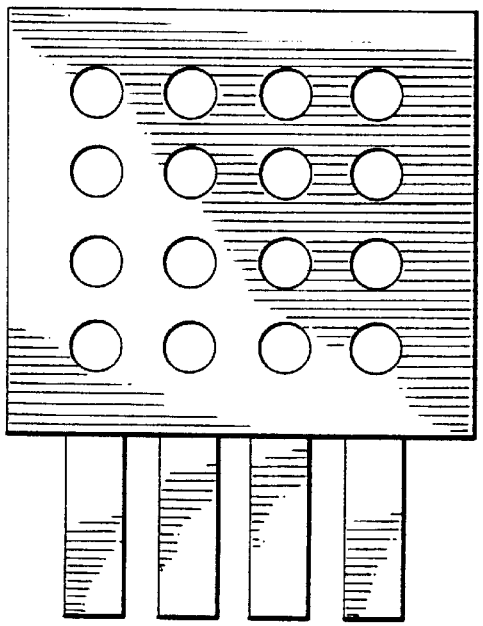
Figure 13F:
Figure 14A:
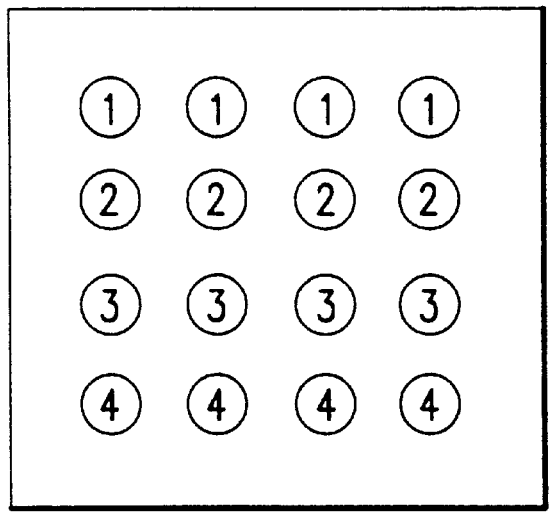
Figure 14B:
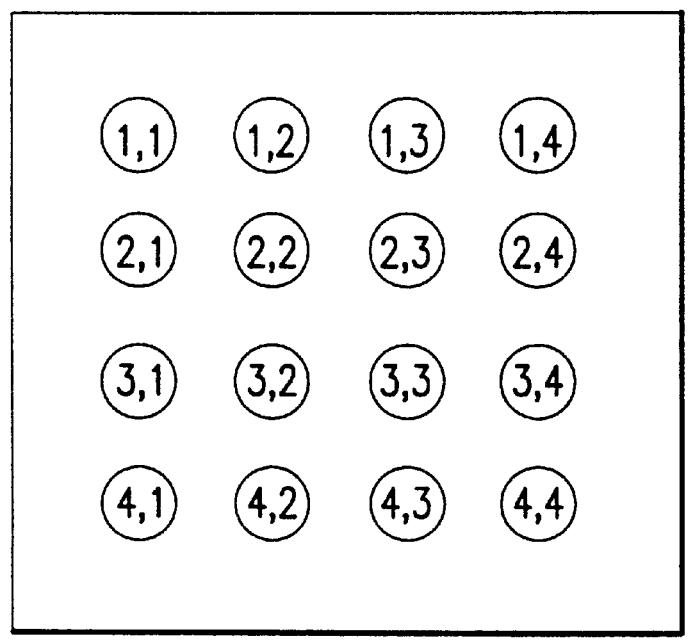
Figure 15A:
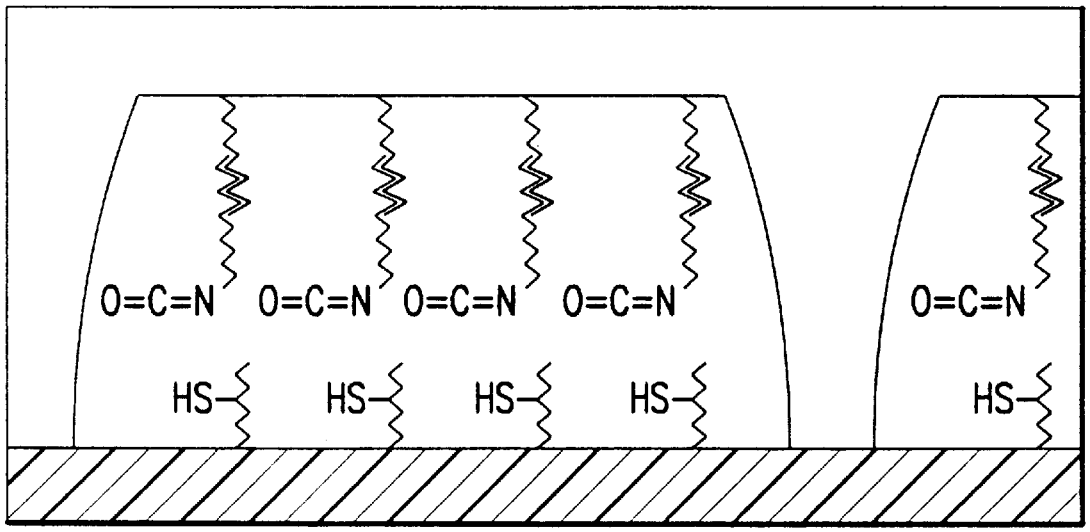
Figure 15B:
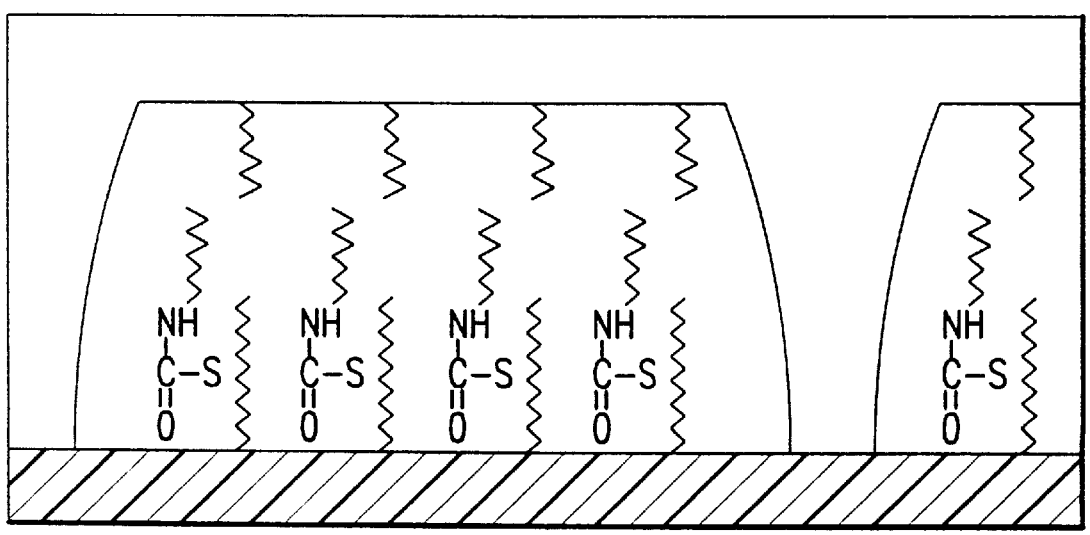
Figure 16:
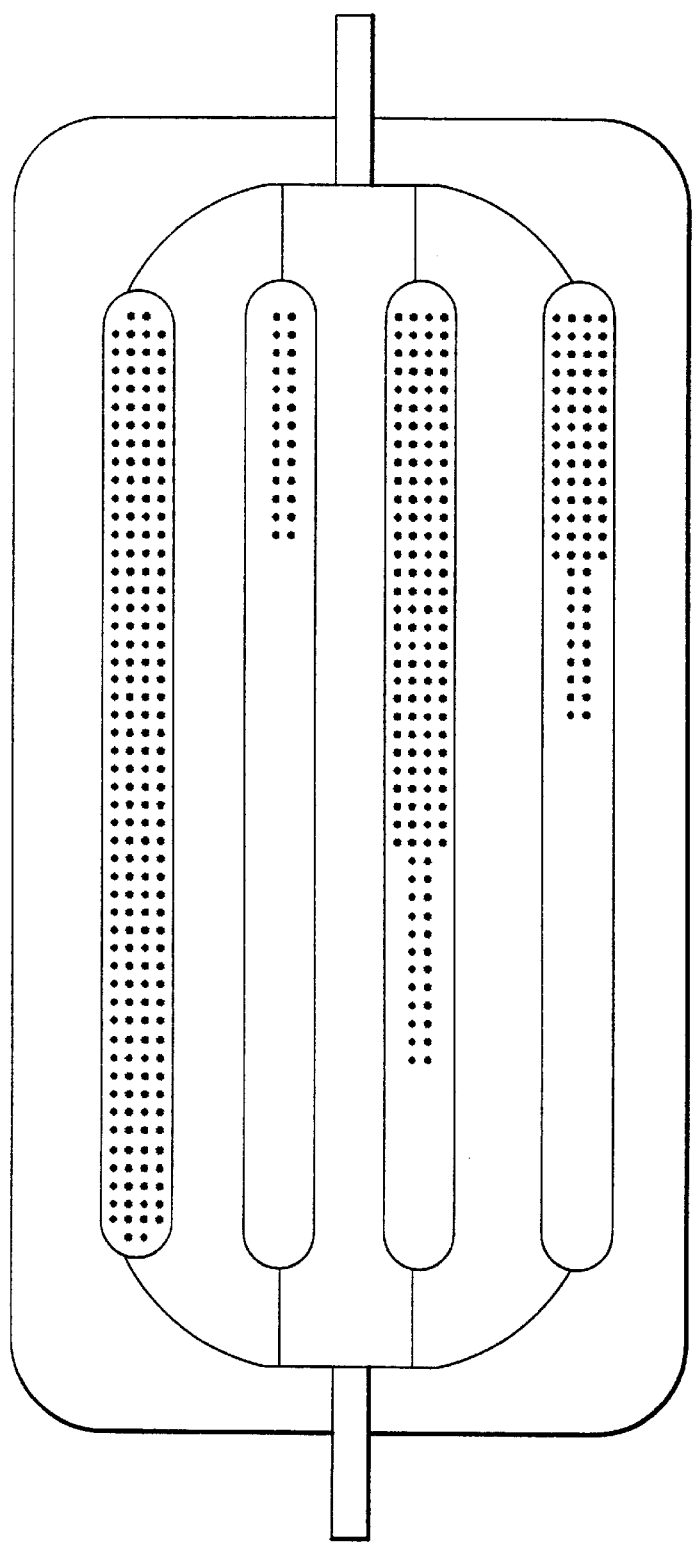
Figure 17A:
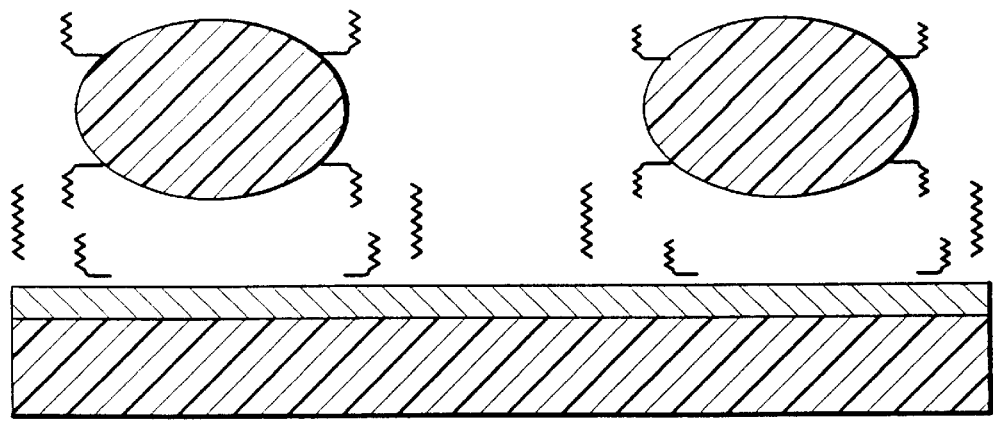
Figure 17B:
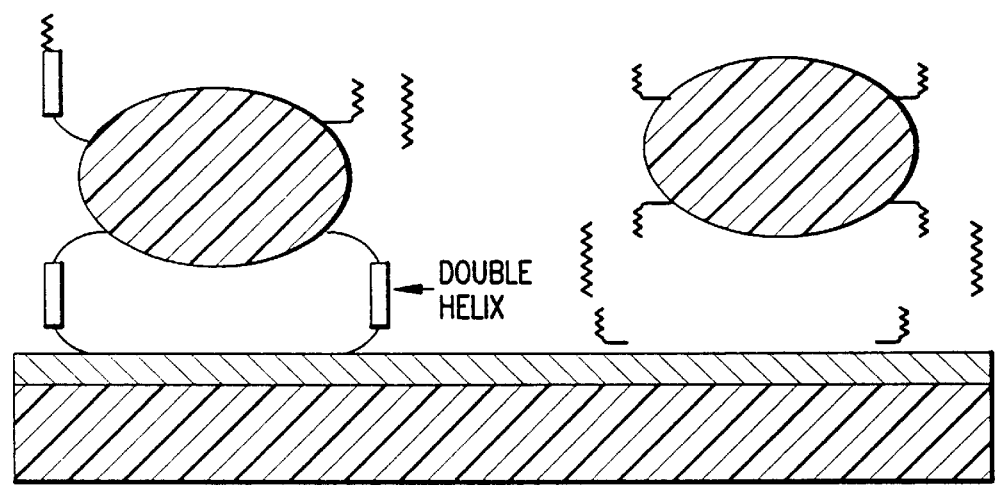
Figure 17C:
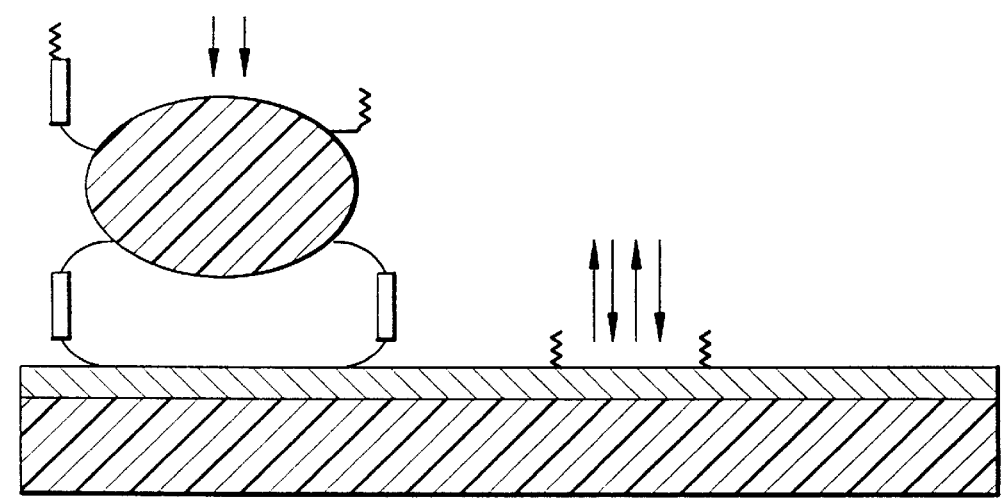
Figure 18A:
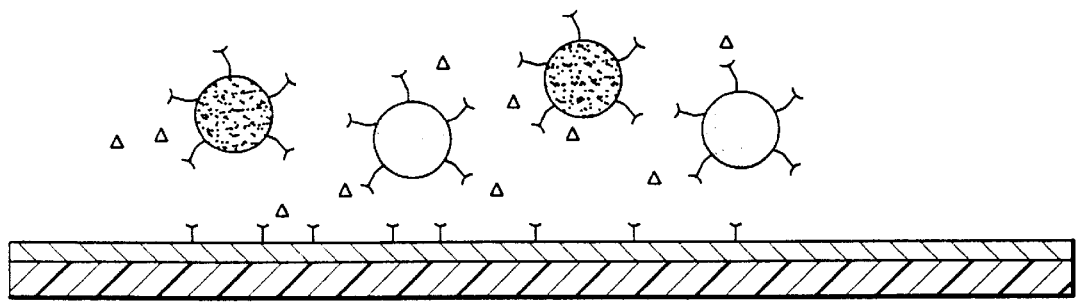
Figure 18B:
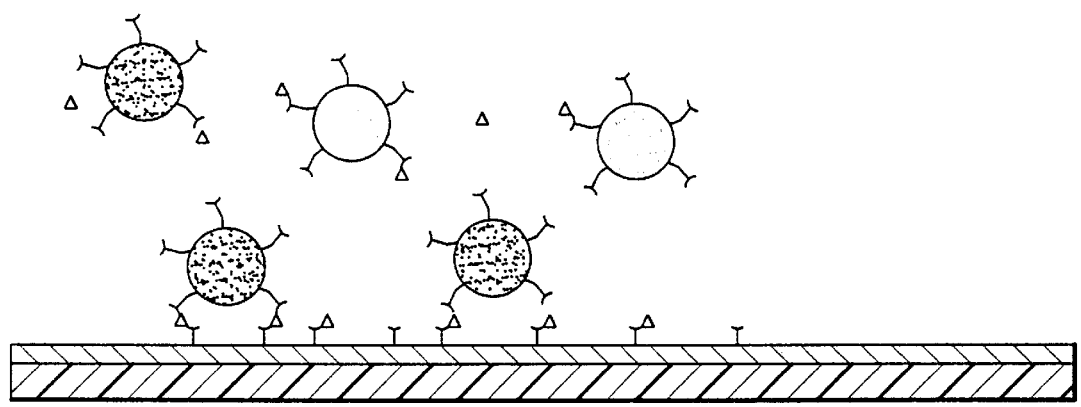
Figure 18C:
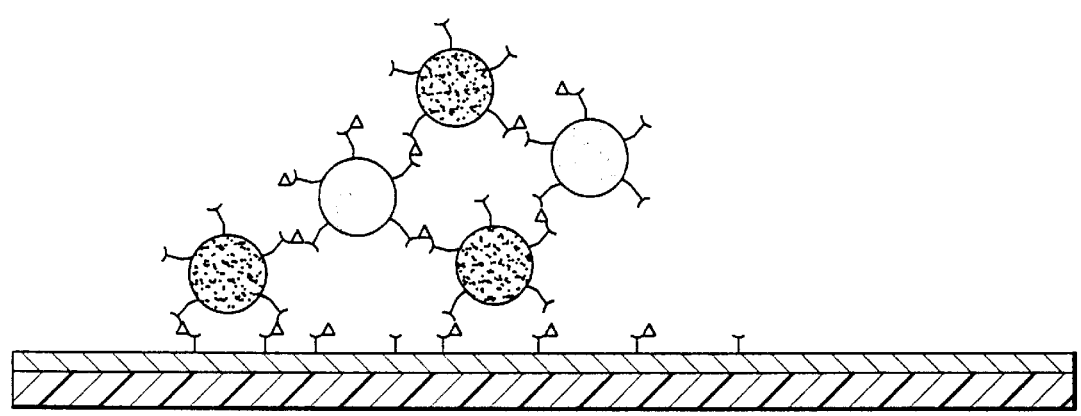

FIG. 2F is a schematic representation, in a nucleic acid detection assay adapted to use the cleavable reflective signal elements of the present invention, of the use of DNA ligase to increase the strength with which analyte-specific binding adheres the signal responsive end of the cleavable spacer to the derivatized substrate of the assay device, thus permitting increased stringency of wash and increased specificity of the assay;

FIG. 3A schematically represents an immunoassay adapted to use the cleavable reflective signal element of the present invention. FIG. 3A illustrates antibodies, adapted to bind to an epitopic site of an antigen suspected to be in a test sample, attached to the side elements of the cleavable spacers of a plurality of signal elements;

FIG. 3B is a schematic representation of a later stage in the assay process represented in FIG. 3A and illustrates binding of antigen from the sample to two antibodies of one cleavable signal element, but failure of antigen from the sample to bind to a second set of antibody side members attached to a second cleavable signal element;

FIG. 3C is a schematic representation of the assay of FIGS. 3A and 3B at a still later stage in the assay process, following cleaving of the signal element spacers. The reflective gold microsphere that is not tethered by the specific bridging association of antigen from the sample to signal element antibodies is removed from the surface of the assay device, providing a spatially-addressable, differentially reflective signal;

FIGS. 4A through 4G illustrate schematically the preparation of the solid support substrate upon which cleavable reflective signal elements are deposited in predetermined patterns to create the spatially addressable assay device of this invention;

FIG. 5 is a schematic representation of the chemical structure of an exemplary cleavable spacer molecule of the cleavable reflective signal element of this invention, subsequent to its attachment to the derivatized plastic substrate surface of the assay device but prior to derivatization with oligonucleotide side members, in which piv denotes a pivaloyl protective group, MMT denotes monomethoxytrityl, and n and m each independently represents an integer greater than or equal to one;

FIG. 6 is a further schematic representation of a cleavable spacer molecule, particularly illustrating the site on the spacer molecule that is susceptible to cleaving, and further indicating the sites for attachment of side members, shown protected by Piv and MMT groups;

FIGS. 7A through 7C illustrate in schematic a means for attaching the cleavable spacer molecules to the activated surface of the assay device substrate. In the example illustrated, the aminated surface of the substrate shown in FIG. 7A is converted to active esters as shown in FIG. 7B. The cleavable spacer molecules are attached via the activated esters to the solid support as shown in FIG. 7C;

FIGS. 8A and 8B illustrate intermediate steps during the attachment of a first oligonucleotide side member on the surface-attaching side of the cleavage site of a plurality of cleavable spacer molecules;

FIGS. 9A and 9B are schematic representations illustrating the intermediate steps in the attachment of a second oligonucleotide member on the signal responsive side of the cleavage site of a plurality of cleavable spacer molecules;

FIG. 10A is a schematic representation illustrating the substantially complete cleavable spacer molecule of the cleavable reflective signal element of the present invention, as attached to the solid substrate of the assay device, and prior to the attachment of the microspheres to the signal-responsive end of the cleavable spacer molecules;

FIG. 10B illustrates the attachment of a single reflective particle to the signal responsive end of the cleavable spacers of FIG. 10A, completing the cleavable reflective signal element of the present invention;

FIGS. 11A through 11G illustrate various patterns of spatially addressable deposition of cleavable reflective signal elements on circular, planar disk substrates, in which:

FIG. 11A particularly identifies an address line, encodable on the disk substrate, from which the location of the cleavable spacers may be measured. In FIG. 11A, the cleavable spacer molecules are deposited in annular tracks;

FIG. 11B demonstrates spiral deposition of cleavable signal elements, and particularly identifies a central void of the disk annulus particularly adapted to engage rotational drive means;

FIG. 11C demonstrates deposition of cleavable signal elements in a pattern suitable for assay of multiple samples in parallel, with concurrent encoding of interpretive software on central tracks;

FIG. 11D schematically represents an embodiment in which the assay device substrate has further been microfabricated to segregate the individual assay sectors, thereby permitting rotation of the assay device during sample addition without sample mixing;

FIG. 11E schematically represents an embodiment in which the assay device substrate has further been microfabricated to compel unidirectional sample flow during rotation of the assay device;

FIG. 11F demonstrates deposition of cleavable signal elements in a spatial organization suitable for assaying 20 samples for 50 different analytes each;

FIG. 11G demonstrates the orthogonally intersecting pattern created by superimposition of spiral patterns with spiral arms of opposite direction or chirality;

FIG. 12 is a schematic representation of detection of analyte-specific signals generated by the assay device of FIG. 11A;

FIG. 13 is a schematic example of a stamp for use in printing oligonucleotide side members onto cleavable spacers previously attached to a solid substrate. The stamp as shown is made of two pieces, a stamp piece and a feeding piece. The stamp piece contains holes, which are filled by the required chemicals through a feeding piece containing channels. The channels in turn are connected to a glass capillary array. In this arrangement, one row of holes is filled with the same chemical. Different hole and channel patterns can be used as needed;

FIG. 14 is a schematic representation of the pattern of oligonucleotide side element deposition resulting from a two-stage orthogonal printing using the stamp depicted in FIG. 13. Numbers 1, 2, 3 and 4 represent different phosphoramidite sequences used in the synthesis. In oligonucleotide synthesis using timers, for example, number 1 can be AAA, number 2 AAC, number 3 AAG and number 4 AAT. The first number in each spot gives the oligonucleotides building block that is most proximal to the cleavable spacer backbone; the second number (if any) represents the next building block. Orthogonal printing is particularly advantageous when depositing the cleavable reflective signal elements of the present invention on a substrate shaped as a disk;

FIG. 15 is a schematic representation of a complementary concave printing process for printing large numbers of oligonucleotide side members simultaneously onto cleavable spacers previously attached to a solid substrate. The cleavable spacers are not themselves shown;

FIG. 16 demonstrates one geometry in which a single sample is channeled in parallel into four distinct sectors of the assay device. If either the density of biobits or affinity of the biobits in the four sectors differs, a large dynamic range of concentration may be determined by detecting the position in each sector of the positive cleavable signal element most distal from the sample application site;

FIG. 17 demonstrates an alternative assay device geometry that dispenses with cleavable spacers, in which a first analyte-specific side element is attached directly to the assay device substrate, while a second analyte-specific side element is attached directly to the signal responsive moiety, shown here as a plastic microsphere;

FIG. 18 demonstrates a further alternative geometry dispensing with cleavable spacers, in which a first side element is attached directly to the assay device substrate, a second side element is attached directly to the signal responsive moiety, and analyte causes agglutination of signal responsive moieties.

5. DETAILED DESCRIPTION OF THE INVENTION

The assay device and assay method of this invention utilize a cleavable signal element for detection of analytes in fluid test samples. Binding of the analyte preselected for detection prevents the loss—through cleavage—of the signal element's signal responsive moiety. Generation of a signal from the signal responsive moiety of the constrained signal element is then used to signal the presence of analyte in the sample.

In a preferred embodiment, the signal responsive moiety reflects or scatters incident light, or is otherwise light addressable. Binding of the analyte preselected for detection prevents the loss—through cleavage—of the signal element's light responsive moiety. Reflection or scattering of incident light, preferably incident laser light, from the reflective moiety of the constrained signal element is then used to signal the presence of analyte in the sample.

The cleavable reflective signal elements of the resent invention are particularly adapted for detection sing existing laser reflectance-based detectors, including audio compact disk (CD) readers, CD-ROM (compact disk read-only memory) readers, laser disk readers, DVD (digital video disk) readers, and the like. The use of the cleavable reflective signal elements of the present invention thus permits the ready adaptation of existing assay chemistries and existing assay schemes to detection using the large installed base of existing laser reflectance-based detectors. This leads to substantial cost savings per assay over standard assays using dedicated detectors.

Furthermore, the wide and ecumenical distribution of laser-reflection based detection equipment further permits assays—as adapted to use the cleavable reflective signal element of the present invention—to be distributed for point-of-service use, assays that must currently be performed at locations determined by the presence of a dedicated detector. Among these assays are immunoassays, cell counting, genetic detection assays based upon hybridization, genetic detection assays based upon nucleic acid sequencing, nucleic acid sequencing itself, and the like. The current invention thus allows distribution of assay devices to research laboratories, physician's offices, and individual homes that must currently be performed at centralized locations.

Each of the laser-reflectance based detectors mentioned hereinabove—including CD-ROM readers, DVD readers and the like—is adapted for detecting, discriminating, and interpreting spatially addressable digital information on their respective media: audio CD readers are capable of specifically and separately addressing individual digitally encoded audio tracks; CD-ROM readers are capable of specifically and separately addressing multiple binary files, including binary files encoding computer programs (ISO 9660, incorporated herein by reference, defines a common addressable file structure); so too DVD readers are capable of specifically and separately addressing binary files and MPEG-encoded digital video signals.

The spatially addressable capabilities of the laser reflectance-based detectors currently used to detect and interpret information encoded on CDs and the like confer particular advantages on assays adapted to use the cleavable reflective signal elements of the present invention.

Thus, patterned deposition of multiple signal elements on a single supporting member or substrate, coupled with use of a detector capable of addressing the spatial location of these individual signal elements, permits the concurrent assay of a single sample for multiple different analytes. The present invention is thus further directed to assay devices, commonly referred to herein as disks, bio-compact disks, bio-CDs, or bio-DVDs, comprising spatially addressable combinations of cleavable reflective signal elements of different analyte specificity. Among such useful combinations are those that increase the predictive value or specificity of each of the individual assays, combinations that inculpate or exculpate particular diagnoses in a differential diagnosis, combinations that provide broad general screening tools, and the like.

Patterned deposition of multiple signal elements with identical specificity further permits the detection, using a single assay device, of large concentration ranges of a single analyte. It is thus another aspect of the present invention to provide assay devices comprising spatially addressable cleavable reflective signal elements of identical specificity, the physical location of which is capable of conveying concentration information.

The spatially addressable capabilities of the laser reflectance-based digital detectors further permits the combination of interpretive software and the assay elements themselves on a single assay device. Another aspect of the current invention, therefore, is an assay device upon which software is encoded in an area spatially distinct from the patterned deposition of cleavable-reflective signal elements. The software may include information important for correct tracking by the incident laser, assay interpretive algorithms, standard control values, self-diagnostics, and the like. The software may include device drivers and software capable of uploading the diagnostic information to remote locations. The software may include patient education information for clinical assays, and may be adapted for chosen audiences.

The substantially binary nature of assay data signalled by the cleavable reflective signal elements of the present invention presents the further advantage of rendering assays adapted to their use substantially resistant to instrumental noise. For example, small variations in light reflection—as from small variations in light intensity provided by the laser source and small variation in reflective particle size—generally do not affect the assay result because the detectors only register a signal when light reflection reaches a threshold. Similarly, electronic noise of the detection device itself and noise associated with an analog to digital conversion do not affect assay results. This advantage is particularly appreciated in designing and manufacturing robust detection instruments useful for field testing or for performing assays under difficult environmental operating conditions.

5.1 Spatially Addressable, Cleavable Reflective Signal Elements

Figure 1A:
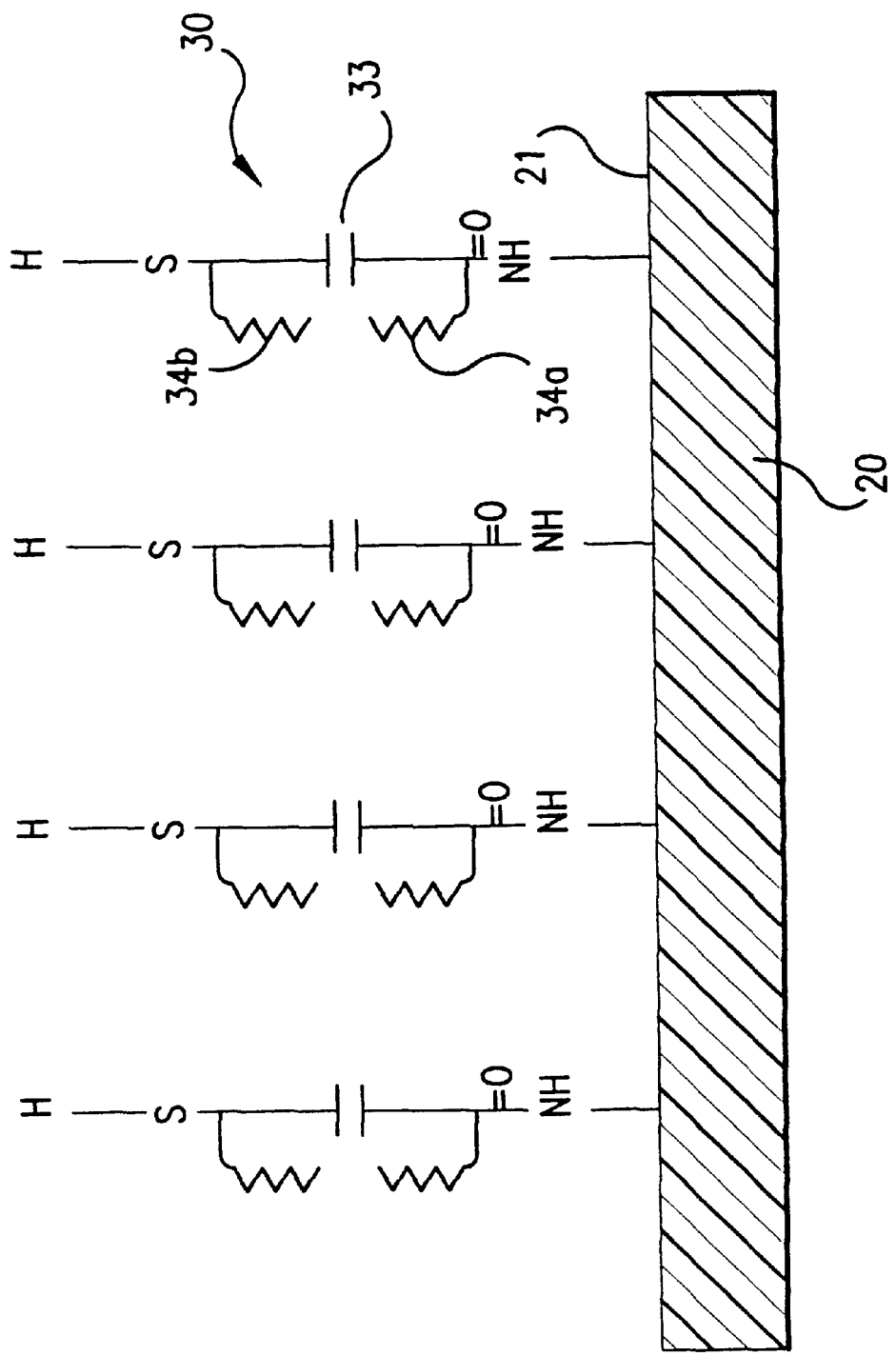
FIG. 1A is a schematic representation of a plurality of cleavable spacers covalently attached at their surface-attaching end to a derivatized site on the assay device substrate.
Figure 1B:
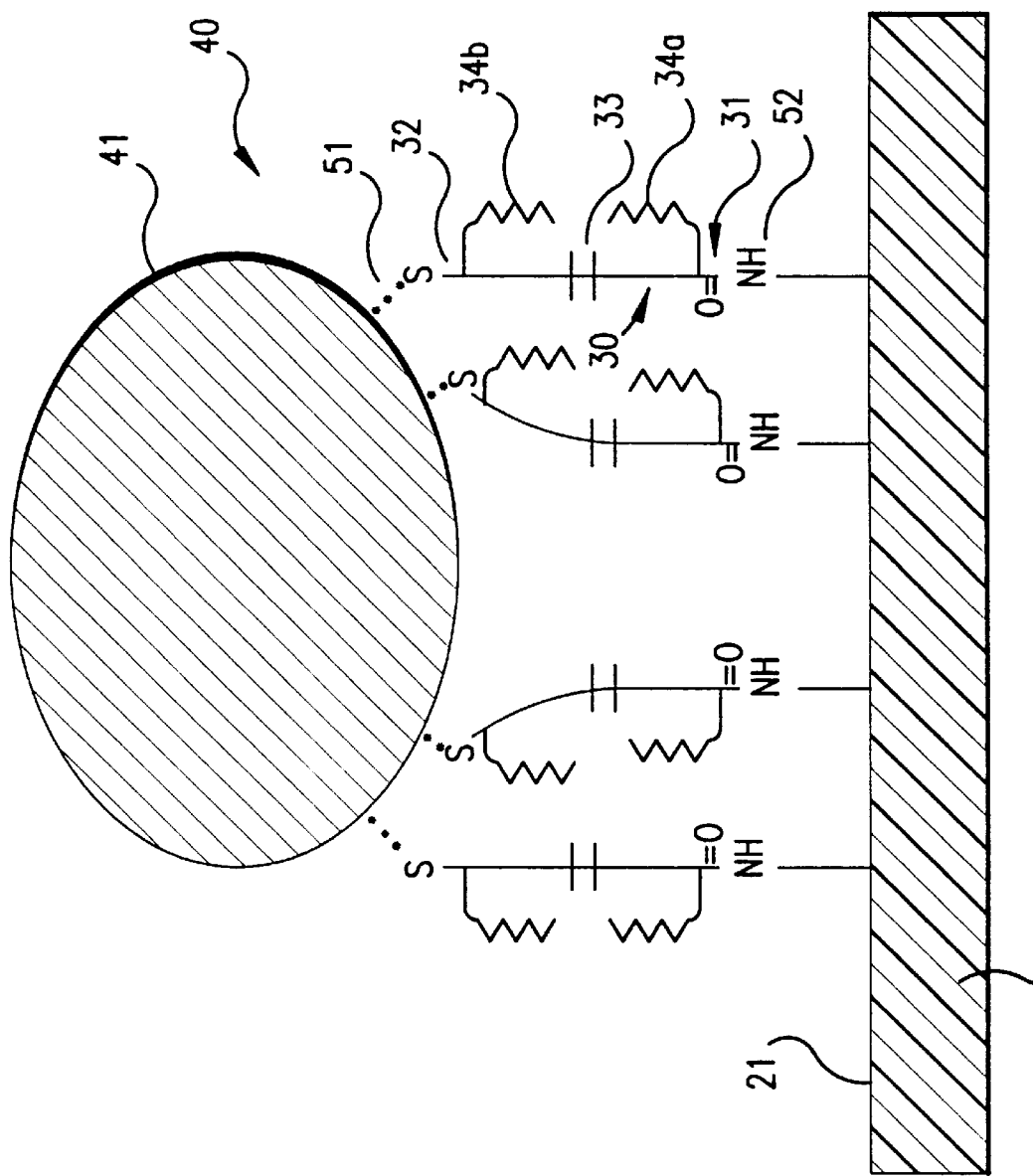
FIG. 1B illustrates the attachment of a reflective signalling means, a metal microsphere, to the signal-responsive ends of the plurality of cleavable spacers, creating cleavable reflective signal elements.

The general operation of the cleavable reflective signal element of this invention, also termed a bio-bit, can be understood more particularly by reference to FIGS. 1–3, which schematize two embodiments of the present invention. With reference to FIG. 1, a substrate 20 is provided with a derivatized surface 21 to which is attached cleavable spacer molecules 30, each cleavable spacer having, in addition to a surface-attaching end, a signal responsive end, shown proximal to metal microsphere 40. The substrate, which may be porous or solid, although solid is presently preferred, can be selected from a variety of materials such as plastics, glass, mica, silicon, and the like. However, plastics are preferred for reasons of economy, ease of derivatization for attaching the spacer molecules to the surface, and compatibility with existing laser reflectance-based detectors, such as CD-ROM and DVD readers. Typical plastics that can be used are polypropylenes, polyacrylates, polyvinyl alcohols, polyethylenes, polymethylmethacrylates and polycarbonates. Presently preferred are polypropylene and polycarbonate, and most preferred polycarbonate.

The surface 21 of the substrate 20 can be conveniently derivatized to provide covalent bonding to each of the cleavable spacer molecules 30. The metal spheres provide a convenient reflective signal-generating means for detecting the presence of a spacer molecule bound to the assay device substrate 20. Typical materials are gold, silver, nickel, chromium, platinum, copper, and the like, with gold being presently preferred for its ability readily and tightly to bind e.g. via dative binding to a free SH group at the signal responsive end of the cleavable spacer. The metal spheres may be solid metal or may be formed of plastic, or glass beads or the like, on which a coating of metal has been deposited. Also, other reflective materials can be used instead of metal. The presently preferred gold spheres bind 51 directly to the thio group of the signal responsive end of the cleavable spacer.

Each of the cleavable spacer molecules is attached at one end 31 to support surface 21, e.g. via an amide linkage, and at the other end 32 to a signal generating means (also termed a signal-responsive moiety), e.g. via a thio radical to a reflective metal microsphere 40. The spacer molecule has a cleavage site 33 that is susceptible to cleavage during the assay procedure, by chemical or enzymatic means, heat, light or the like, depending on the nature of the cleavage site. Chemical means are presently preferred with a siloxane cleavage group, and a solution of sodium fluoride, exemplary, respectively, of a chemical cleavage site and chemical cleaving agent. Other groups susceptible to cleaving, such as ester groups or dithio groups can also be used. Dithio groups are especially advantageous if gold spheres are added after cleaving the spacer.

Cleavage site 33 is between the first, surface-attaching end 31 of cleavable spacer molecule 30 and the second, signal-responsive end 32 of cleavable spacer molecule 30. Spacers may contain two or more cleavage sites to optimize the complete cleavage of all spacers.

Analyte specificity is conferred upon the cleavable spacer by side members 34a and 34b, also termed side arms, positioned on opposite sides of the cleavage site 33; that is, positioned proximal to the surface-attaching end and proximal to the signal-responsive end of cleavable spacer molecule 30, respectively. Side members 34a and 34b in their typical configuration include an oligonucleotide, typically 5- to 20-mers, preferably 8- to 17-mers, most preferably 8- to 12-mers, although longer oligonucleotides can be used. The side members may also include, without limitation and as required, peptides, organic linkers to peptides or proteins, or the like. A large number of cleavable spacer molecules 30 will be present at any particular derivatized site on the solid surface 21 of the assay device, also termed a disk, a bio-compatible disk, or BCD.

In one aspect of the invention, the oligonucleotide side members are adapted to bind complementary single strands of nucleic acids that may be present in a test sample. The complementary oligonucleotides comprise members of a specific binding pair, i.e., one oligonucleotide will bind to a second complementary oligonucleotide.

Figure 2A:
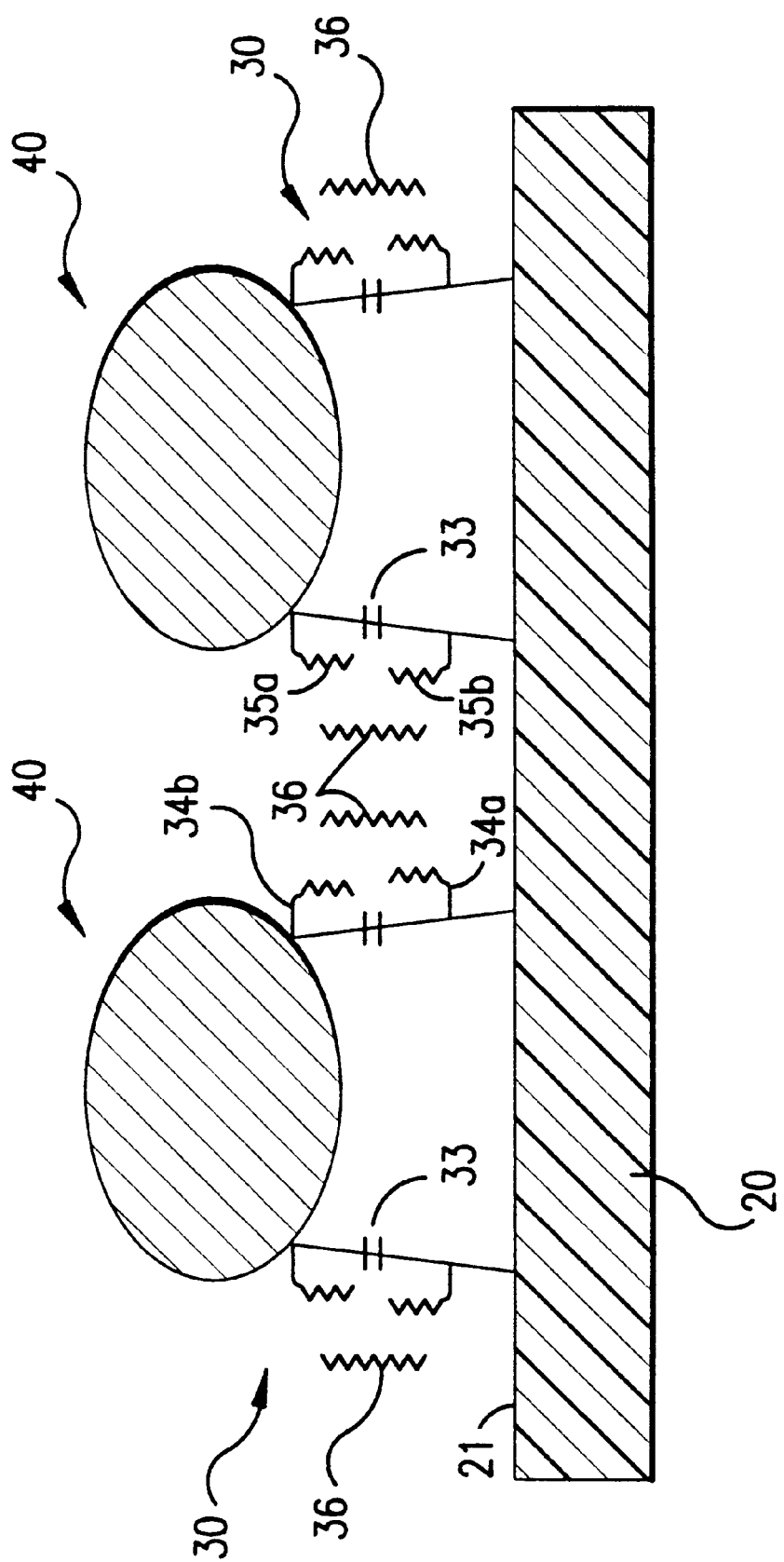
FIG. 2A is a schematic representation of a nucleic acid hybridization assay adapted to use the cleavable reflective signal elements of the present invention, shortly after introduction of a sample containing nucleic acids.
Figure 2B:
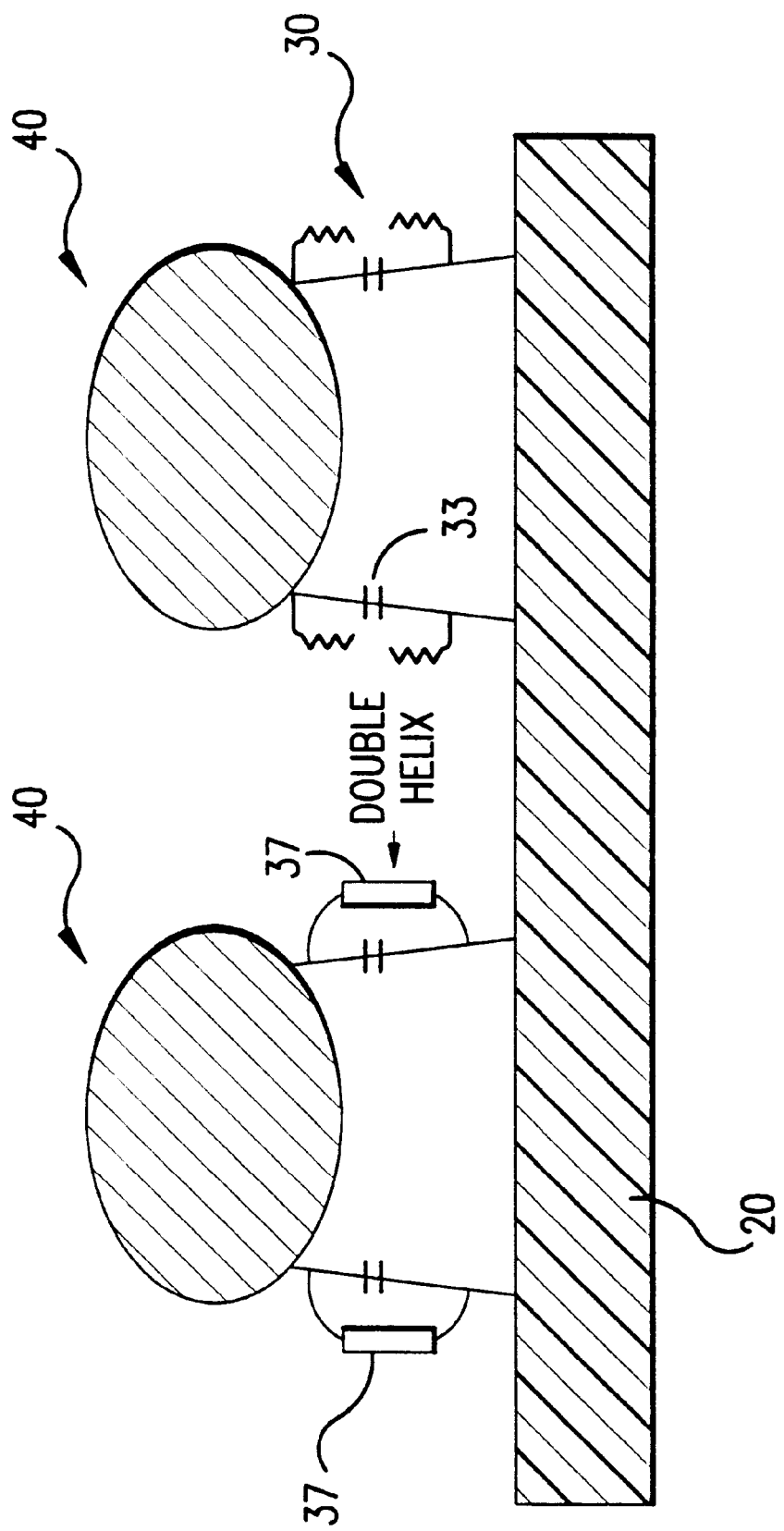
FIG. 2B is a schematic representation of a later stage of the assay procedure of FIG. 2A, in which oligonucleotides present in the sample have bound to complementary oligonucleotide side elements of a first cleavable signal element, but have not bound to a second, different, set of oligonucleotide side elements of a second cleavable signal element.
Figure 2C:
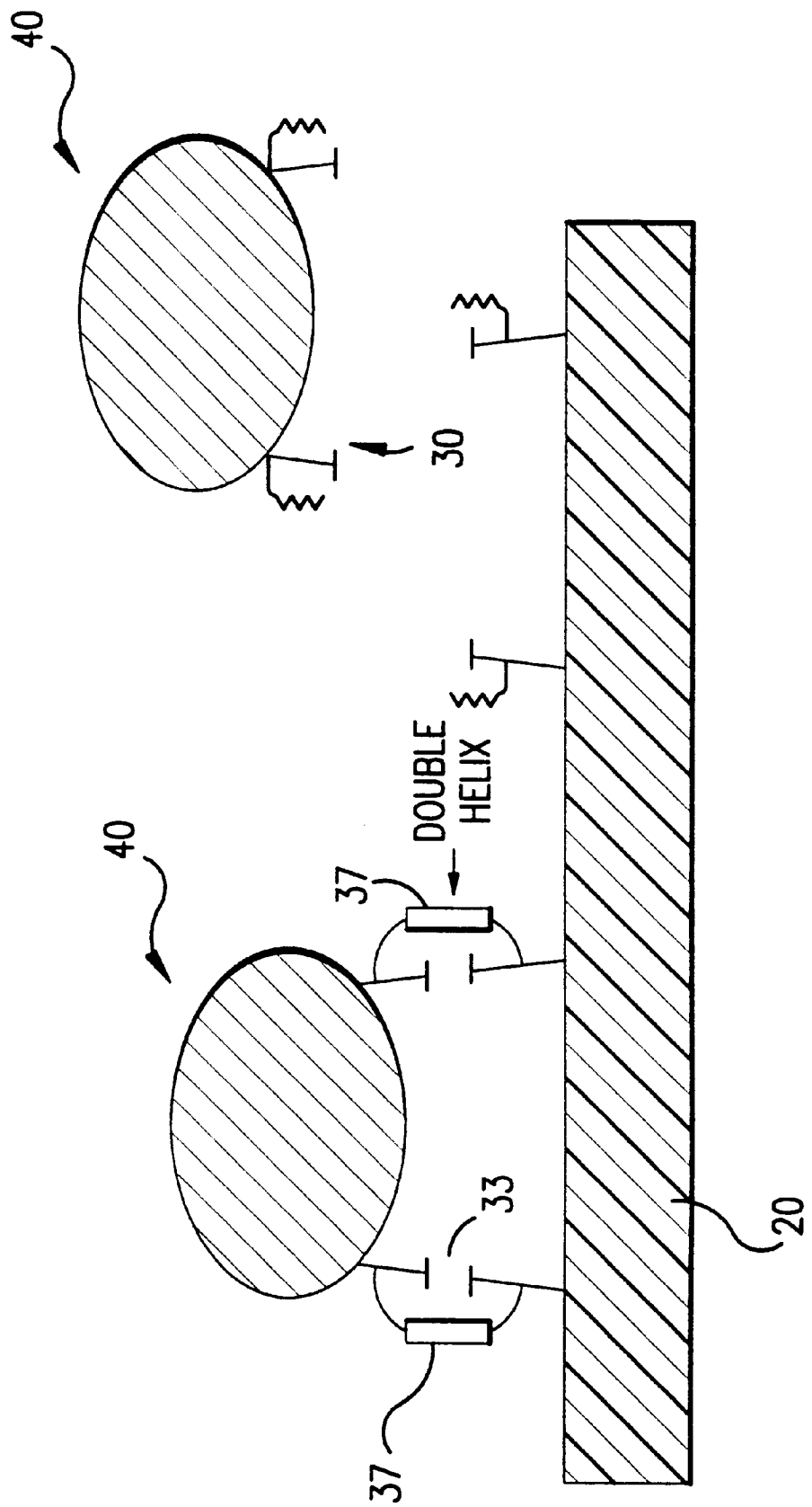
FIG. 2C is a schematic representation of a later stage of the assay procedure of FIGS. 2A and 2B, following cleavage of the spacer molecules. The reflective gold microsphere that is not tethered by the specific hybridization of complementary oligonucleotides from the test sample is removed from the surface of the assay device, providing a spatially-addressable, differentially reflective signal.

As is described more particularly in FIGS. 2A through 2C, schematizing one embodiment of the invention, cleavable spacer molecules 30 at different sites on the surface of the assay device will have different oligonucleotide side members. As shown in FIG. 2A, one such cleavable signal element has oligonucleotide side members 34a and 34b, whereas the second cleavable signal element has oligonucleotide side members 35a and 35b.

As further depicted in FIGS. 2A through 2C, when contacted with a test sample containing an oligonucleotide 36, the complementary oligonucleotide side members 34a and 34b will bind with the oligonucleotide present in the sample to form a double helix as is shown in FIG. 2B. Since there is no complementarity between oligonucleotide 36 and oligonucleotide side members 35a and 35b, there is no binding between those groups as is further illustrated in FIG. 2B.

When the cleavage site 33 is cleaved, but for the binding by the double helix coupled oligonucleotides the metal microspheres 40 will be free of the surface and removed therefrom. This is illustrated more fully in FIG. 2C. If it is desired to assay multiple samples for a single oligonucleotide, the spacer molecules at different sites will generally have the same oligonucleotide side members. Presence and absence of the metal microsphere 40 may then be detected as reflectance or absence of reflectance of incident light, particularly incident laser light.

FIG. 2F is a schematic representation of the use of DNA ligase in a further embodiment of the nucleic acid detection embodiment of the present invention to increase the strength with which analyte-specific binding adheres the signal responsive end of the cleavable spacer to the derivatized substrate of the assay device, thus permitting in this embodiment increased stringency of wash, affording increased specificity of the assay.

It will be appreciated by those skilled in nucleic acid detection that the cleavable reflective signal elements of the present invention are particularly well suited for detecting amplified nucleic acids of defined size, particularly nucleic acids amplified using the various forms of polymerase chain reaction (PCR), ligase chain reaction (LCR), amplification schemes using T7 and SP6 RNA polymerase, and the like.

In a further embodiment of the invention described in FIGS. 3A through 3C, the oligonucleotide side members 34a, 34b, 35a, and 35b are coupled noncovalently to modified antibodies 38a, 38b, 38c, and 38d to permit an immunoassay. The noncovalent attachment of modified antibodies to side members is mediated through complementarity of cleavable spacer side member oligonucleotides and oligonucleotides that are covalently attached to the antibodies. Use of complementary nucleic acid molecules to effectuate noncovalent, combinatorial assembly of supramolecular structures is described in further detail in co-owned and copending U.S. patent application Ser. No. 08/332,514, filed Oct. 31, 1994, Ser. No. 08/424,874, filed Apr. 19, 1995, and Ser. No. 08/627,695, filed Mar. 29, 1996, incorporated herein by reference. In another embodiment, antibodies can be attached covalently to the cleavable spacer using conventional cross-linking agents, either directly or through linkers.

The antibodies comprise a first member of a first specific binding pair and a first member of a second specific binding pair. The second member of the first specific binding pair and the second member of the second specific binding pair will be different epitopic sites of an antigen of interest. More specifically, oligonucleotide side member 35a is attached to the antibody-oligonucleotide 38c and oligonucleotide side member 35b is attached to antibody-oligonucleotide 38d. The antibodies 38c and 38d are adapted to bind different epitopic sites on an antigen that may be present in the test sample. By different epitopic sites on an antigen is intended different, spatially separated, occurrences of the same epitope or different epitopes present at distinct sites. At a second assay element, the oligonucleotide side members 34a and 34b are attached to different antibodies 38a and 38b, again each of such antibodies being adapted to attach to a different epitopic site of an antigen.

With further reference to the immunoassay schematized in FIGS. 3A–3C, upon application of the test solution containing antigen 39 to the collection of cleavable reflective signal elements illustrated in FIG. 3A, antigen 39 binds antibodies 34a and 34b, thus preventing decoupling of the metal sphere 40 from the assay device surface 20 when the cleavage site 33 is cleaved, such as, for example, by contact with a chemical cleaving agent. In contrast, the second cleavable signal element, which was not bound by antigen 39 because the lack of binding affinity of the antibodies 35a and 35b to the antigen 39, allow the metal microsphere 40 to separate from the solid surface and be removed from the sample.

Presence and absence of the metal microsphere 40 may then be detected as reflectance or absence of reflectance of incident light, particularly incident laser light.

As should be apparent, coupling of antibodies as depicted permits ready adaptation of standard immunoassay chemistries and immunoassay geometries for use with the cleavable reflective signal elements of the present invention. Some of these classical immunoassay geometries are further described in U.S. Pat. No. 5,168,057, issued Dec. 1, 1992, incorporated herein by reference. Thus, it should be apparent that the direct detection of analyte schematized in FIG. 3 is but one of the immunoassay geometries adaptable to the cleavable reflective signal elements and assay device of the present invention. The present invention will prove particularly valuable in immunoassays screening for human immunodeficiency viruses, hepatitis A virus, hepatitis B virus, hepatitis C virus, and human herpesviruses.

It will further be appreciated that antibodies are exemplary of the broader concept of specific binding pairs, wherein the antibody may be considered the first member of the specific binding pair, and the antigen to which it binds the second member of the specific binding pair. In general, a specific binding pair may be defined as two molecules the mutual affinity of which is of sufficient avidity and specificity to permit the practice of the present invention. Thus, the reflective cleavable signal elements of the present invention may include other specific binding pair members as side elements. In such embodiments, the first side member of the cleavable signal element includes a first member of a first specific binding pair, the second side member of the cleavable spacer includes a first member of a second specific binding pair, wherein said second member of said first specific binding pair and said second member of said second specific binding pair are connectably attached to one another, permitting the formation of a tethering loop of the general formula: first member of first specific binding pair-second member of first specific binding pair-second member of second specific binding pair-first member of second specific binding pair.

Among the specific binding pairs well known in the art are biologic receptors and their natural agonist and antagonist ligands, proteins and cofactors, biotin and either avidin or streptavidin, alpha spectrin and beta spectrin monomers, and antibody Fc portions and Fc receptors.

While the above-exemplified embodiments—direct detection of nucleic acid analytes and direct immunoassay—have been described with reflective metal spheres attached to the cleavable spacer molecules prior to conducting the assay, it is contemplated in these and other embodiments further described herein that cleavable spacer molecules lacking a signal generating means can first be exposed to sample, then cleaved, and the metal spheres added later so as to attach to only those spacer molecules remaining on the surface. After addition of the metal spheres, the surface can then be read with an appropriate detector to identify the bound spacer molecules and analytes.

In each of the assay method embodiments of the invention, a sample to be tested must first be introduced. In one aspect, the assay device is rotated and a fluid sample, preferably diluted, is applied near the center of the circular assay device substrate. The centrifugal forces associated with the rotation of the assay device disk distribute the fluid sample across the planar face of the solid substrate. In this manner the surface of the substrate is uniformly covered with a constant and uniformly distributed fluid sample.

In this method of sample application, the test sample, initially about 100 $\mu$l, is diluted for processing to about 1 ml. This solution is added dropwise near the center of the rotating disk. The assay sites and possibly the surface of the disk are hydrophilic and a fluid will form a very thin layer on the rotating assay device disk. The thickness of the fluid layer can be regulated by the frequency of drop addition and frequency of disk rotation. A preferred thickness is less than 10 $\mu$m, because all molecules in the sample can then interact with the stationary molecules bound by the spacers. About 100 $\mu$l of the sample solution is needed to cover the disk.

Other methods of sample application may be used with the cleavable reflective signal element and assay device of the present invention. In particular, it should be appreciated that the rotational application above-described is suitable principally for application of a single sample per assay device. In other aspects of the present invention, separate samples may be applied to discrete areas of a stationary disk. In this aspect, the assay system can assay approximately one thousand different samples. Approximately one million gold spheres, which are applied onto a predetermined areas on the disk, can be dedicated for each sample.

FIG. 11D shows an assay device of the present invention having 16 separate assay sectors. FIG. 11E shows a possible direction for sample flow, with barriers to fluid flow shown as lines.

Thus, in one embodiment of the invention, the assay device is designed to assay, for example, 1024 patient samples simultaneously, one analyte per assay device (i.e., per disk, each disk comprising a plurality of cleavable spacers with identical side members conferring identical analyte specificity). In such an embodiment, each of the spacer molecules on the disk may be identical, so as to assay for the same analyte; spacer molecules at particular locations on the disk will be identical to spacer molecules at other locations on the disk. This application is particularly useful in mass analysis conducted in clinical laboratories where a large number of patient samples are analyzed at the same time for the presence or absence of a single analyte.

It will also be appreciated that multiple samples may be assayed for multiple analytes on a single assay device comprising cleavable reflective signal elements with various analyte specificities. FIG. 11F shows an assay device that can be used to screen 20 samples for 50 different biomolecules.

In the latter case, it is possible to assay for a limited number of the same analytes in a multiplicity of test samples. Patient samples may be applied to the disk at specific locations by known methods such as ink jet printing and micropipet arrays with disposable tips, or a combination thereof. For large through-put operations, the assay disks may be loaded into a cassette and test samples loaded hermetically either directly onto the disk or into the wells in a circular plate.

After an appropriate incubation period, which may only be a few seconds to allow the sample to traverse the surface of the support, a wash step may be, but in some embodiments need not be, performed to remove unbound sample. Wash stringency may be adjusted as in conventional assays to adjust sensitivity and specificity. For example, in nucleic acid detection embodiments, the salt concentration of the wash solution may be decreased to increase the stringency of wash—thus reducing mismatch as between analyte and specificity-conferring side members—or increased, to decrease the stringency of wash, thereby permitting mismatch to occur. Adjusting the stringency of wash in the nucleic acid hybridization and immunoassay embodiments of the present invention is well within the skill in the art.

In one aspect, the surface of the circular disk is washed, when necessary, by adding a wash solution near the center of the rotating disk. The sample solution is removed as it pushes out from the periphery of the disk and is collected. Because of the rotation of the disk, the wash step may be eliminated if the fluid sample is adequately removed from the disk by normal centrifugal forces and no adjustment to stringency is required.

After the wash step, if any, a solution including a cleaving agent is added and again distributed over the surface of the disk. With reference to FIGS. 1–3, the spacer molecule has a cleavage site 33 that is susceptible to cleavage during the assay procedure, by chemical or enzymatic means, heat, light or the like, depending on the nature of the cleavage site. Chemical means are presently preferred with the siloxane cleavage group, and a solution of sodium fluoride is exemplary as a chemical cleaving agent for the siloxane group. Other groups susceptible to cleaving, such as ester groups or dithio groups, can be used. Dithio groups are especially advantageous if gold spheres are added after cleaving the spacer.

In the case of the cleavage site being a siloxane moiety, which can be made stable against spontaneous hydrolysis but is easily cleaved under mild conditions by a fluoride ion, sodium fluoride solution is introduced, with concentration of 1 mM to 1 M, preferably 50 mM to 500 mM, most preferably 100 mM (0.1 M). The cleavage step will last only a few seconds. Although all spacers are cleaved during this step, the amide bond between the cleavable spacer and the derivatized substrate of the assay device remains stable to these conditions.

After application of sample and cleavage of the spacers, the detached signal-generating moieties, preferably a reflective moiety, more preferably a metal sphere, most preferably a gold sphere, must be removed to provide differential signal during detection. The removal step may include a second wash step, which may include introduction of wash solutions.

Several means exist by which differential wash stringencies may be developed at this stage of the assay, thereby permitting variation in the specificity and sensitivity of the various assay methods.

In one aspect, the detached reflective moieties may be removed by rotating the assay device, with or without addition of wash solution. In this aspect, three parameters may be varied to provide differential stringency: gold particle size, rotational speed, and the valency of spacer attachment.

Gold spheres suitable for use in the cleavable reflective signal element and assay device of the present invention are readily available in varying diameters from Aldrich Chemical Company, British BioCell International, Nanoprobes, Inc., and others, ranging from 1 nm to and including 0.5–5 micrometers in diameter. It is within the skill in the art to create gold spheres of lesser or greater diameter as needed in the present invention. At a given rotational speed, the largest gold spheres experience larger centrifugal (relative to $r^3$) and drag forces (relative to r) and are removed before smaller spheres with equal bonding. This provides a basis for differential stringency of wash, and also of quantitative analysis.

The centrifugal force affecting the gold spheres may also be adjusted by rotation frequency so that the loose and weakly bound gold spheres are removed. Only the spacers which have bound to a complementary molecule from the sample will continue to bind the gold spheres to the substrate.

Furthermore, while the above embodiments of the invention have been described with a single metal sphere attached to the signal-responsive end of a single cleavable spacer, it should be appreciated that when gold is used in a preferred embodiment of the invention, thousands of spacers may bind one gold sphere, depending upon its diameter. Thus, the stringency of the assay wash may be adjusted, at any given rotational speed, by varying the diameter of the gold sphere, and by varying additionally the relative density of cleavable spacers to gold spheres.

Thus, if virtually all spacers under a certain gold sphere are connected by complementary molecules, the binding is very strong. If the spacers are fixated only partially under a certain gold sphere, the sphere may remain or be removed depending on the radius of the sphere and the frequency of the rotation.

In extreme cases all spheres are either fixed or are removed. These are expected alternatives for DNA analysis. In immunoassays the intermediary cases are preferred. Accordingly, the system should be optimized so that the normal control level corresponds to 50% fixation of the gold spheres. Higher or lower fixation corresponds to higher or lower concentrations of the analyte, respectively, when using two antibodies for binding as illustrated in FIG. 3.

A strong centrifugal force can be used to remove weakly bound gold spheres. The centrifugal force pulling one gold sphere will be in the order of 0.1 nN, although this force can vary within large limits depending ont eh mass of the gold sphere and the frequency of the rotation of the disk. The force is strong enough to rupture nonspecific binding of antibodies and to mechanically denature mismatching oligonucleotides. This is a very strong factor for increasing the specificity of the interaction between analyte and the cleavable signal elements of the present invention.

In embodiments of the present invention in which the reflective moiety of the cleavable spacer is ferromagnetic, as, for example, in which the reflective moiety is a gold-coated iron bead or an iron alloy, those reflective moieties detached through cleavage and not secured to the assay device substrate by analyte may be removed through application of a magnetic field. In such embodiments, those signal elements that remain attached to the assay device (disk) substrate will also be responsive to the metal field, but their motion will be constrained by the length and flexibility of the loop formed by the first side member-analyte-second side member. The ability to shift the position of all attached signal elements through application of an external magnetic field, even though that shift will necessarily be constrained by the length and flexibility of the first side member-analyte-second side member loop, may add, in this embodiment, additional information. In particular, brief application of a magnetic field will facilitate discrimination of analyte-induced signal from random noise, the noise being unresponsive to the application of an external magnetic field.

After removal of cleaved reflective signal moieties that are not protected by the specific binding of analyte, the disk may be read directly. Alternatively, the disk may first be disinfected before reading. In yet another embodiment, the disk may be covered by an optically clear plastic coating to prevent the further removal of the gold spheres through spin coating with a polymerizable lacquer that is polymerized with UV-light. Spin coating of compact disks is well established in the art. The assay disk is expected to have a shelf-life of well over ten years.

Subsequently, the disk can be scanned by a laser reader which will detect, through reflection, the presence of a microsphere or other reflective element at the various spatially predetermined locations. Based on the distance of the microsphere from the axis of rotation of the disk and the angular distance from an address line forming a radial line on the disk, the location of a particular metal sphere can be specifically determined. Based on that specific location and the predetermined locations of specific binding pairs as compared to a master distribution map, the identity of the bound material can be identified. Thus, in the foregoing manner it is possible in one fluid sample to analyze for thousands, or even greater numbers, of analytes simultaneously.

5.2 Derivatization of Substrate

Figure 4A:
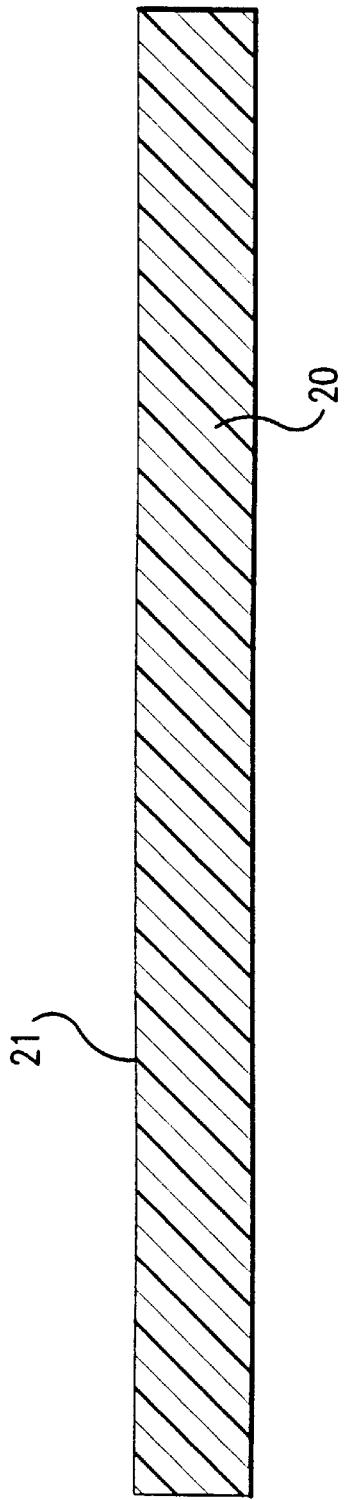
Figure 4B:
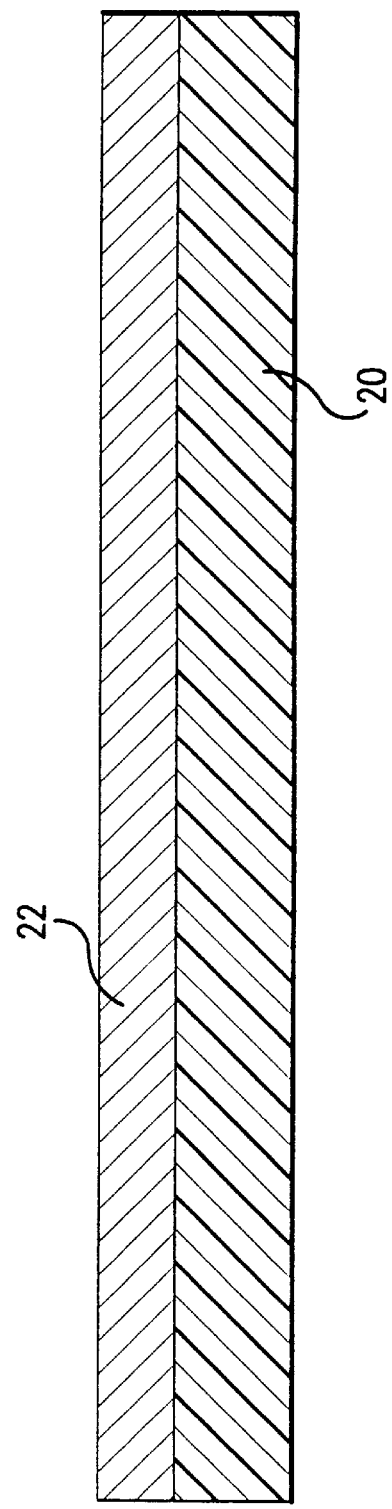
Figure 4E:
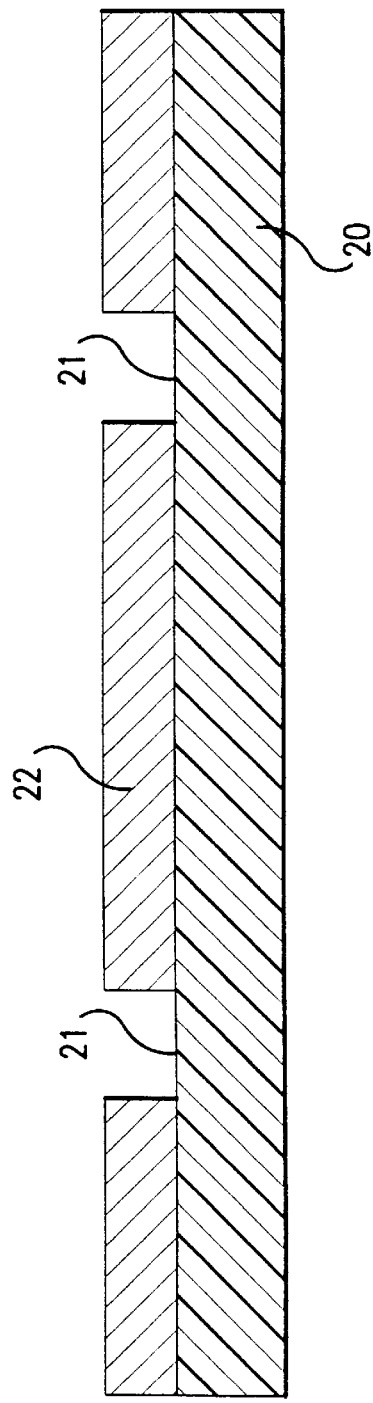
Figure 4F:
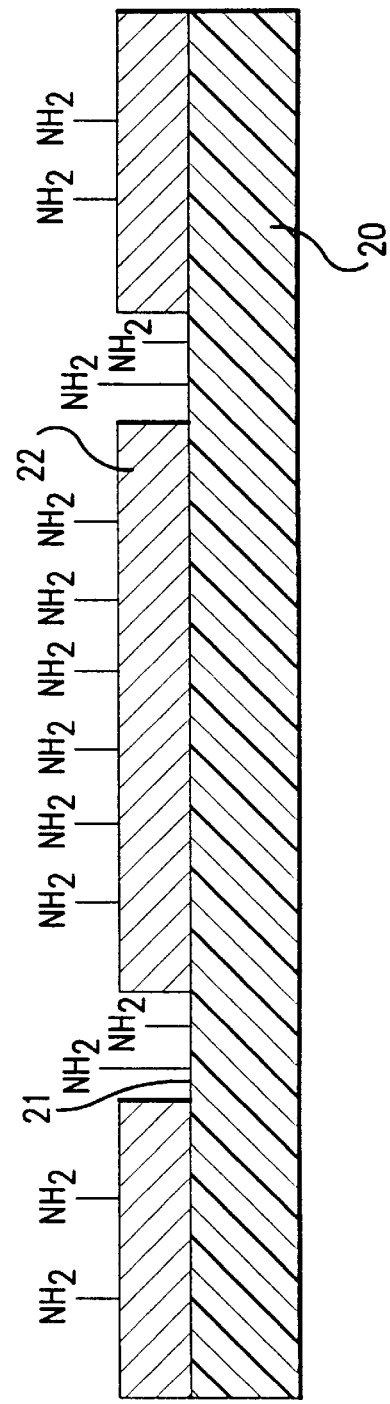
Figure 4G:
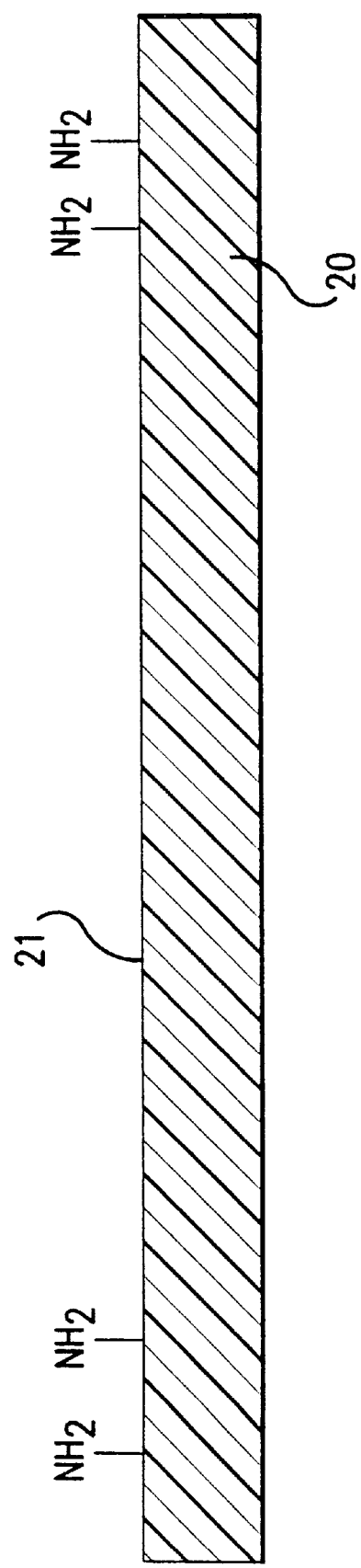

FIGS. 4A through 4G illustrate schematically the preparation of the solid support substrate upon which cleavable reflective signal elements are deposited to create the assay device of this invention. A portion of a generally planer solid support is illustrated in FIG. 4A. As illustrated in FIG. 4B, the surface of the support is coated with a resist 22, e.g., a high melting point wax or the like. Next a pattern of indentations or holes 25 in the resist is created by stamping with stamp 23 containing protrusions 24, as illustrated in FIG. 4C. The pattern is highly regular and indentations are made in all sites at which cleavable spacer molecules will desirably be located on the surface of the support. Any resist remaining at the bottom of the indentations, as illustrated in FIG. 4D, is removed, as shown in FIG. 4E. The exposed areas of the substrate 21, as illustrated in FIG. 4E, are activated or derivatized to provide for the attachment of bonding groups (e.g., amino groups) to the surface of the substrate and to any remaining resist 22, as represented in FIG. 4F. Finally, the remaining resist is removed to expose the original surface of the substrate to which amino groups are coupled at certain predetermined sites as illustrated in FIG. 4G.

Blank disks are available from Disc Manufacturing, Inc. (Wilmington, Del.). Amino derivatization may be performed by ammonia plasma using a radio frequency plasma generator (ENI, Rochester, N.Y.).

5.3 Synthesis and Attachment of Cleavable Spacers

With reference to FIG. 1 and FIGS. 5 and 6, a representative cleavable spacer molecule is described. Most of the spacer, termed the backbone, is poly(alkyleneglycol), e.g., polyethyleneglycol, having a molecular weight of 400–10,000, preferably 400–2000. The backbone has a first end 31 that is adapted to couple to a derivatized amine group present on surface 21 of substrate 20, and a second end 32, which is adapted to couple with surface 41 of metal microsphere 40 via a thio-linkage 51. The backbone includes a cleavage site 33 between the first end 31 and the second end 32 of spacer molecule 30. In addition, between end 31 and cleavage site 33 is a side member 34a, commonly constructed from an oligonucleotide, and between cleavage site 33 and end 32 is another side member 34b commonly constructed from an oligonucleotide. Alternatively, such side members may be peptides or other organic molecules. More than two side members can be provided, but it is only necessary that two members are capable of forming a connective, molecular loop around the cleavage site to bind the spacer molecule to the surface of the substrate after cleavage at the cleavage site. These side members can be attached to the spacer backbone by linkers, such as polyethylene glycol.

One mode of synthesis of the cleavable spacer molecule 30 illustrated in FIG. 5 is substantially and generally as follows: chlorodimethylsilane is coupled unto both ends of a polyethyleneglycol molecule. The silane group incorporated into the molecule reacts in the presence of catalytic amounts of chloroplatinic acid within N-acryloyl serine. The hydroxyl groups of both serine moieties are to be used later in the synthesis for the construction of oligonucleotide side members. One hydroxyl group is first protected by a monomethoxytriphenylmethyl group and the product is purified by liquid chromatography. The other hydroxyl group is then protected with a pivaloyl or fluorenylmethyloxycarbonyl (FMOC) group. The serine carboxyl groups are coupled with amino terminated poly(ethyleneglycol). The amino group at the other end is further derivatized by 3-(2-pyridyldithio) propionic acid N-hydroxysuccinimide ester. The other amino group is not reacted but is free to react later with the derivatized substrate.

An alternative, but substantially similar, and more detailed description of the spacer molecule synthesis, is provided below and in the Preparations that follow. The structure of the spacer molecule is shown schematically in FIG. 5. The synthesis is begun by constructing the central portion of the spacer molecule first. Both ends of the poly(ethyleneglycol) are then silanized, e.g. with chlorodimethylsilane to afford a compound of the formula of Compound I.

The silane groups then are derivatized with an alkenoic acid, straight or branched chain (e.g., $CH=CH(CH_2)_nCOOH$, n=1–11, although the number of carbon atoms is immaterial, such as vinyl acetic acid, acrylic acid and the like) having a terminal double bond, such as vinyl acetic acid to form a compound having the structural formula of Compound II, and reacted further to provide a protected hydroxyl group on each side of the silane to provide for later attachment of oligonucleotides as illustrated by the compound having the structural formula of Compound III.

Various common reactants can be used for this purpose, and N-acryloyl serine and TMT-serine methyl ester, when allowed to react in the presence of a catalyst such as chloroplatinic acid, are exemplifications of preferred reactants. The resulting ester is partially hydrolyzed by the addition of an alkali metal hydroxide, such as sodium hydroxide, in an alcoholic solvent, and the adjacent protected hydroxyl group is preferentially hydrolyzed to yield a compound represented by the structural formula of Compound IV.

Amino terminated poly(ethyleneglycol) is derivatized at one end with a thio ester, such as 3-(2-pyridyldithio) propionic acid N-hydroxy succinimide ester, and coupled with Compound IV to yield a compound represented by the structural formula of Compound VI. The terminal ester group is hydrolyzed to yield the acid, which is further reacted with methoxyacetic acid, to afford the compound represented by the structural formula of Compound VIII. That compound is treated with aminated poly (ethyleneglycol) to form the completed spacer molecule substantially as illustrated in FIG. 5.

Preparation 1: Compound I

To a mixture of poly(ethyleneglycol) (10 g, 10 mmol, av. MW 1,000 Aldrich Chemical Company) and triethylamine (TEA) (2.1 g, 21 mmol) in 100 ml of dichlormethane (DCM), is added dropwise 2.0 g of chlorodimethylsilane in 20 ml of DCM with cooling in an ice bath. After 10 minutes, the reaction mixture is filtered and the filtrate is applied into a 200 g silica column. The column is eluted with DCM/MeOH 19:1, and the eluant affords poly(ethyleneglycol), di(dimethylsilyl) ether, the compound represented by the structural formula of Compound I.

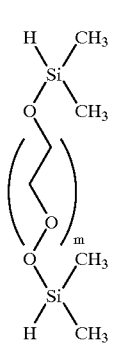

Compound I

Preparation 2: Compound II

Compound I (10 g, 9 mmol) and vinylacetic acid (1.72 g, 20 mmol) is dissolved into 60 ml of ethyl acetate (EtOAc). A catalytic amount (40 mg) of chloroplatinic acid is added, and the mixture is heated to boiling and boiled for 1 hour. After cooling, the solution is applied directly into a 200 g. silica column. The column is eluted with EtOAc and EtOAc/MeOH 9:1, and the eluant affords poly(ethyleneglycol), di(2-carboxyethyldimethylsilyl) ether, the compound represented by the structural formula of Compound II.

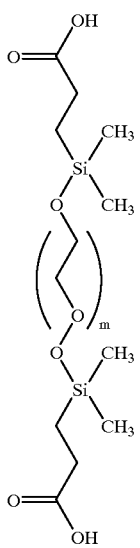

Compound II

Preparation 3: Compound III

Compound II (9.5 g, 8 mmol) and trimethoxytrityl-serine methyl ester (7.0 g, 16 mmol) are dissolved into 100 ml of DCM. Dicyclohexylcarbodiimide (DCC) (3.25 g, 16 mmol) in 30 ml of DCM is added dropwise at room temperature. After 1 hour the reaction mixture is filtered. The filtrate is applied directly into 300 g silica column. The column is eluted with DCM/TEA 99:1 and then with DCM/MeOH/TEA 94:5:1. The eluant affords the compound represented by the structural formula of Compound III.

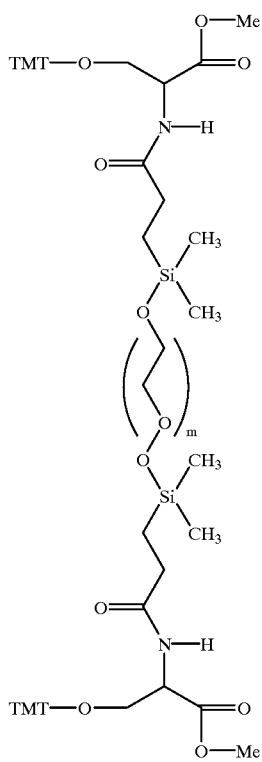

Compound III

Preparation 4: Compound IV

Compound III (10 g, 5 mmol) is dissolved into 100 ml of EtOH and partially hydrolyzed by adding 10 ml 0.5 M NaOH in EtOH. The mixture is slightly acidified by adding 300 mg (5 mmol) acetic acid. The TMT-group proximal to the carboxylate group is preferentially hydrolyzed. After 30 min the mixture is made slightly basic by adding 0.5 ml tetraethylamine (TEA). The EtOH solution is fractionated by HPLC using a reverse phase column eluted with EtOH/Water/TEA 90:9:1. The eluant affords the compound represented by the structural formula of Compound IV.

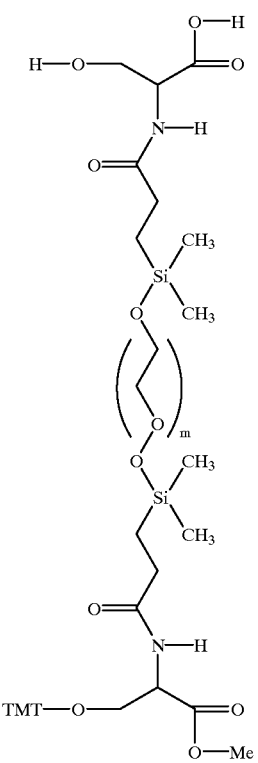

Compound IV

Preparation 5: Compound V

O,O'-Bis(aminopropyl)polyethyleneglycol (9.5 g, 5 mmol, av. MW 1900), triethylamine (0.5 g, 5 mmol) and 3-(2-pyridyldithio) propionic acid N-hydroxysuccinimide ester (0.77 g, 2.5 mmol) are dissolved into 150 ml of DCM. The mixture is stirred 1 hour at room temperature, concentrated into half volume and fractionated in 200 g silica column. The column is eluted with DCM/MeOH 95:5, to afford the compound represented by the structural formula of Compound V.

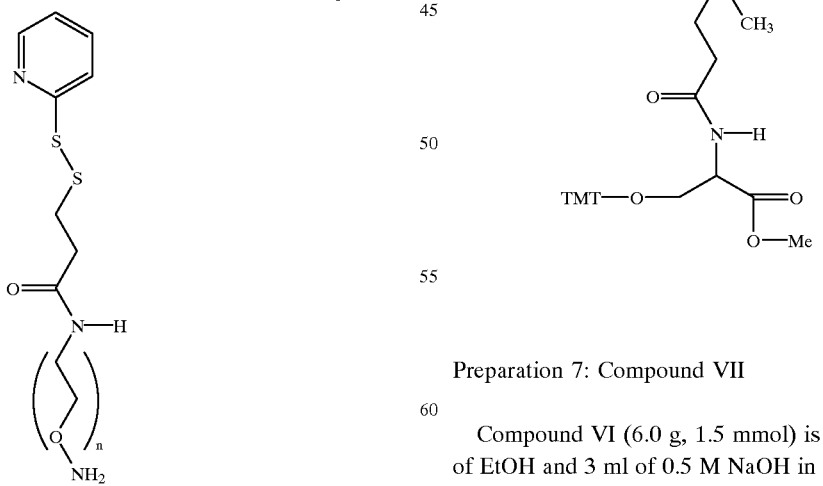

Compound V

Preparation 6: Compound VI

Compound IV (3.5 g, 2 mmol) and Compound V (4.4 g, 2 mmol) are dissolved into 100 ml of DCM and 450 mg (2.2 mmol) DCC in 5 ml of DCM is added. After 1 hour the mixture is filtered, and fractionated in 150 g silica column. The column is eluted with DCM/MeOH/TEA 94/5/1, to afford the compound represented by the structural formula of Compound VI.

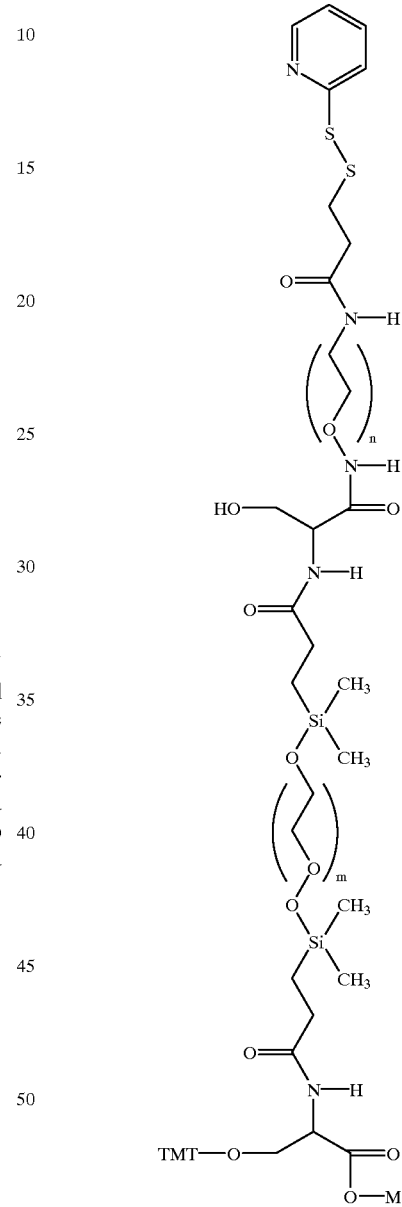

Compound VI

Preparation 7: Compound VII

Compound VI (6.0 g, 1.5 mmol) is dissolved into 50 ml of EtOH and 3 ml of 0.5 M NaOH in EtOH is added. After 30 min the product is purified by reverse phase HPLC using EtOH/water/TEA EtOH/Water/TEA 90:9:1 as an eluent, to afford the compound represented by the structural formula of Compound VII.

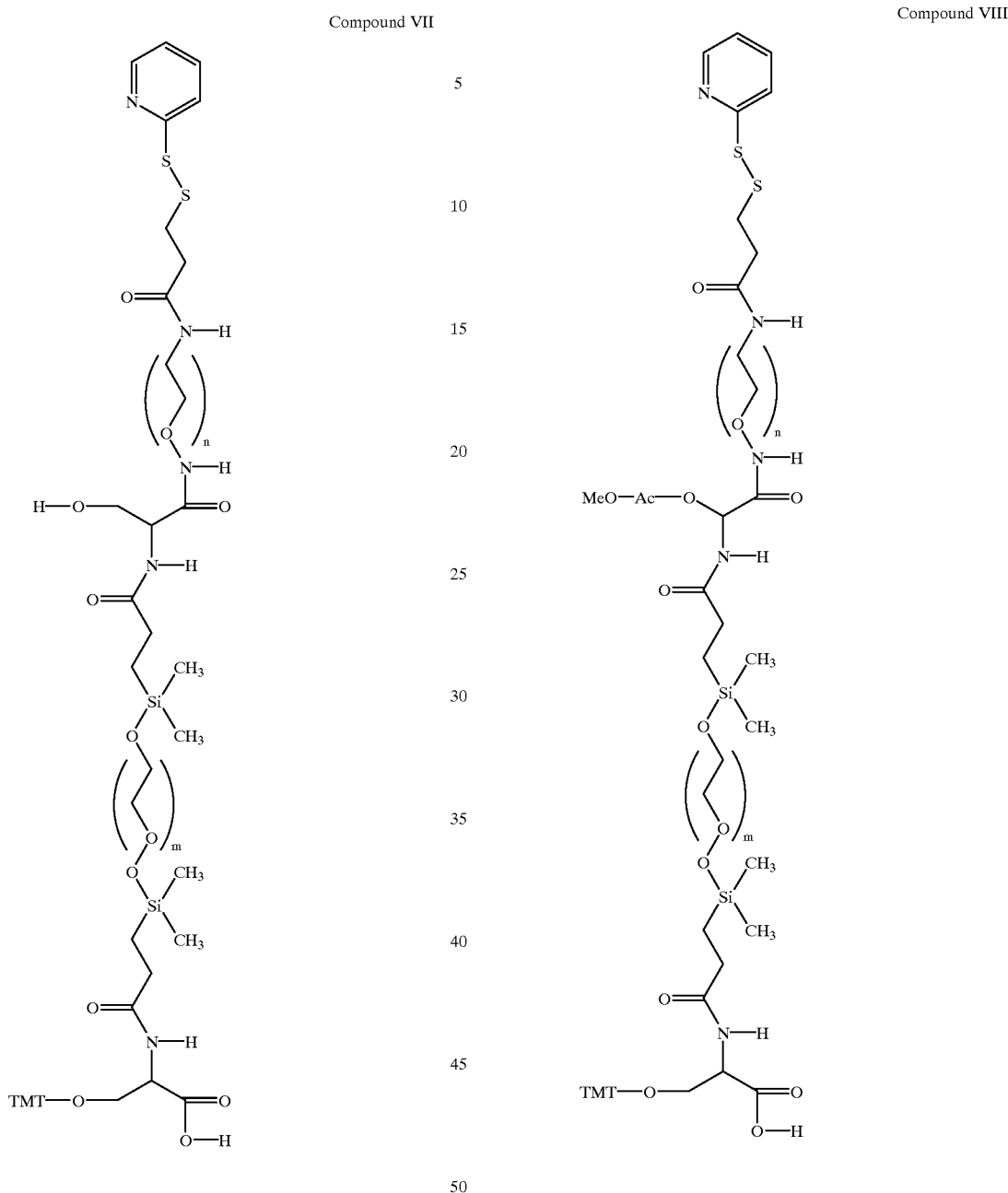

Preparation 8: Compound VIII

Compound VII (4.0 g, 1 mmol) is dissolved into 80 ml of DCM. The mixture of 320 mg (2 mmol) of methoxyacetic acid anhydride and 202 mg (2 mmol) of triethylamine in 5 ml of DCM is added. The mixture is evaporated by rotary evaporator into dryness. The residue is purified by reverse phase HPLC using EtOH/water/TEA EtOH/Water/TEA 90:9:1 as an eluent, to afford the compound represented by the structural formula of Compound VIII.

Preparation 9: Compound IX

Compound VIII (4.0 g, 1 mmol) and 0,0'-bis (aminopropyl)poly-ethyleneglycol (4.8 g, 2.5 mmol, av. MW 1900) are dissolved into 100 ml of DCM, 230 mg (1,1 mmol) DCC in 5 ml of DCM is added. After 1 hour the mixture is filtered and the mixture is fractionated in 100 g silica column using DCM/MeOH/TEA 94/5/1 as an eluent, to afford the compound represented by the structural formula of Compound IX, substantially as schematically represented in FIG. 5.

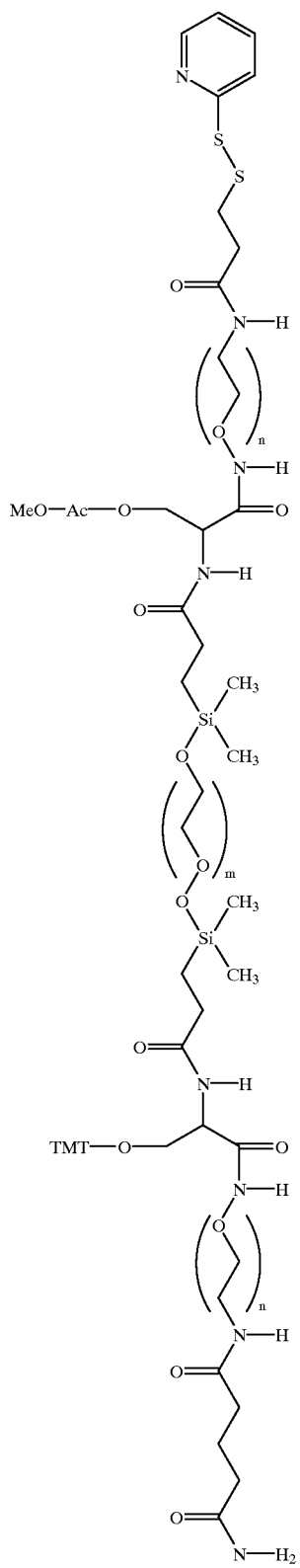

Compound IX

5.4 Attachment of Cleavable Spacers to Substrate

Each of the spacer molecules is attached at one end 31 to support surface 21, e.g. via an amide linkage. In order to attach the spacer molecules to the amino activated substrate, glutaric anhydride is reacted with the amino groups to expose a carboxylate group, shown more particularly in FIGS. 7A and 7B. The carboxylate groups can be esterified with pentafluorophenol. The free amino group on the spacer molecule will couple with this active ester. The spacer molecules and their attachment at the discrete sites to the solid support surface 21 are shown particularly in FIG. 7C. At this stage in the fabrication the hydroxyl groups remain protected. While the oligonucleotide side members could be pre-synthesized on the spacers prior to the attachment to the solid surface support 21, it is preferable that they be attached after the spacer molecule 30 is attached on the solid support.

5.5 Design and Attachment of Signal Responsive Moieties

One feature of the current invention is the detection of signal responsive moieties associated with the cleavable spacer molecules deposited in predetermined spatially addressable patterns on the surface of the assay device. Accordingly, this invention provides methods, compositions and devices for attaching signal responsive moieties and for detecting signal associated with cleavable spacer molecules.

5.5.1 Gold Particles as Signal Responsive Moieties

In some preferred embodiments of the present invention, particles that reflect or scatter light are used as signal responsive moieties. A light reflecting and/or scattering particle is a molecule or a material that causes incident light to be reflected or scattered elastically, i.e., substantially without absorbing the light energy. Such light reflecting and/or scattering particles include, for example, metal particles, colloidal metal such as colloidal gold, colloidal non-metal labels such as colloidal selenium, dyed plastic particles made of latex, polystyrene, polymethylacrylate, polycarbonate or similar materials.

The size of such particles ranges from 1 nm to 10 $\mu$m, preferably from 500 nm to 5 $\mu$m, and most preferably from 1 to 3 $\mu$m. The larger the particle, the greater the light scattering effect. As this will be true of both bound and bulk solution particles, however, background may also increase with particle size used for scatter signals.

Metal microspheres 1 nm to 10 $\mu$m (micrometers) in diameter, preferably 0.5–5 $\mu$m, most preferably 1–3 $\mu$m in diameter, are presently preferred in the light reflecting/light scattering embodiment of the present invention. Metal spheres provide a convenient signal responsive moiety for detection of the presence of a cleaved, yet analyte-restrained, spacer molecule bound to the disk. Typical materials are gold, silver, nickel, chromium, platinum, copper, and the like, or alloys thereof, with gold being presently preferred. The metal spheres may be solid metal or may be formed of plastic, or glass beads or the like, upon which a coating of metal has been deposited. Similarly, the light-reflective metal surface may be deposited on a metal microsphere of different composition. Metal spheres may also be alloys or aggregates.

Gold spheres suitable for use in the cleavable reflective signal element and assay device of the present invention are readily available in varying diameters from Aldrich Chemical Company, British BioCell International, Nanoprobes, Inc., and others, ranging from 1 nm to and including 0.5 $\mu$m (500 nm)–5 $\mu$m in diameter. It is within the skill in the art to create gold spheres of lesser or greater diameter as needed in the present invention.

Much smaller spheres can be used advantageously when reading is performed with near field optical microscopy, UV-light, electron beam or scanning probe microscopy. Smaller spheres are preferred in these latter embodiments because more cleavable spacers can be discriminated in a given area of a substrate.

Although spherical particles are presently preferred, non-spherical particles are also useful for some embodiments.

In biological applications, the signal responsive moiety—particularly gold or latex microspheres—will preferably be coated with detergents or derivatized so that they have a surface charge. This is done to prevent the attachment of these particles nonspecifically with surfaces or with each other.

The presently preferred gold spheres bind directly to the thio group of the signal responsive end of the cleavable spacer, yielding a very strong bond.

After the oligonucleotide side arm synthesis is completed, as further described below, the pyridyldithio group present at the signal-responsive end of the spacer molecule 30 is reduced with dithioerythritol or the like. The reaction is very fast and quantitative, and the resulting reduced thio groups have a high affinity for gold. Halo groups similarly have high affinity for gold. Accordingly, gold spheres are spread as a suspension in a liquid (e.g., distilled water) by adding the suspension to the surface of the solid support 21. The gold spheres will attach only to the sites covered by thio terminated spacers and will not attach to the remaining surface of the substrate.

Furthermore, while the above embodiments of the invention have been described with a single metal sphere attached to the signal-responsive end of a single cleavable spacer, it should be appreciated that when gold is used in a preferred embodiment of the invention, thousands of spacers may bind one gold sphere, depending upon its diameter. It is estimated that one sphere of 1–3 $\mu$m may be bound by approximately 1,000–10,000 cleavable spacers.

As a result, the stringency of the assay wash may be adjusted, at any given rotational speed, by varying not only the diameter of the gold sphere, but also the relative density of cleavable spacers to gold spheres.

Accordingly, if virtually all spacers under a certain gold sphere are connected by complementary molecules, the binding is very strong. If the spacers are fixated only partially under a certain gold sphere, the sphere may remain or be removed depending on the radius of the sphere and the frequency of the rotation.

5.5.2 Other Light-Responsive Signal Responsive Moieties

In some other embodiments of the cleavable signal element and assay device of the present invention, a light-absorbing rather than light-reflective material can be used as a signal responsive moiety. In this embodiment, the absence of reflected light from an addressed location, rather than its presence, indicates the capture of analyte. The approach is analogous to, albeit somewhat different from, that used in recordable compact disks.

Although similar in concept and compatible with CD readers, information is recorded differently in a recordable compact disk (CD-R) as compared to the encoding of information via pits in a standard, pressed, CD. In CD-R, the data layer is separate from the polycarbonate substrate. The polycarbonate substrate instead has impressed upon it a continuous spiral groove as a reference alignment guide for the incident laser. An organic dye is used to form the data layer. Although cyanine was the first material used for these discs, a metal-stabilized cyanine compound is generally used instead of "raw" cyanine. An alternative material is phthalocyanine. One such metallophthalocyanine compound is described in U.S. Pat. No. 5,580,696.

In CD-R, the organic dye layer is sandwiched between the polycarbonate substrate and the metalized reflective layer, usually 24 carat gold, but alternatively silver, of the media. Information is recorded by a recording laser of appropriate preselected wavelength that selectively melts "pits" into the dye layer—rather than burning holes in the dye, it simply melts it slightly, causing it to become non-translucent so that the reading laser beam is refracted rather than reflected back to the reader'sensors, as by a physical pit in the standard pressed CD. As in a standard CD, a lacquer coating protects the information-bearing layers.

A greater number of light-absorbing dyes may be used in this embodiment of the present invention than may be used in CD-R. Light absorbing dyes are any compounds that absorb energy from the electromagnetic spectrum, ideally at wavelength(s) that correspond the to the wavelength(s) of the light source. As is known in the art, dyes generally consist of conjugated heterocyclic structures, exemplified by the following classes of dyes: azo dyes, diazo dyes, triazine dyes, food colorings or biological stains. Specific dyes include: Coomasie Brilliant Blue R-250 Dye (Biorad Labs, Richmond, Calif.); Reactive Red 2 (Sigma Chemical Company, St. Louis, Mo.), bromophenol blue (Sigma); xylene cyanol (Sigma); and phenolphthalein (Sigma). The Sigma-Aldrich Handbook of Stains, Dyes and Indicators by Floyd J. Green, published by Aldrich Chemical Company, Inc., (Milwaukee, Wis.) provides a wealth of data for other dyes. With these data, dyes with the appropriate light absorption properties can be selected to coincide with the wavelengths emitted by the light source.

In these embodiments, opaque dye-containing particles, rather than reflective particles, may be used as a light-responsive signal moiety, thereby reversing the phase of encoded information. The latex spheres may vary from 1–100 $\mu$m in diameter, preferably 10–90 $\mu$m in diameter, and are most preferably 10–50 $\mu$m in diameter. The dye will prevent reflection of laser light from the metallic layer of the disk substrate.

In yet other embodiments, the signal responsive element may be a fluorescer, such as fluorescein, propidium iodide or phycoerythrin, or a chemiluminescer, such as luciferin, which respond to incident light, or an indicator enzyme that cleaves soluble fluorescent substrates into insoluble form. Other fluorescent dyes useful in this embodiment include texas red, rhodamine, green fluorescent protein, and the like. Fluorescent dyes will prove particularly useful when blue lasers become widely available.

The light-reflective, light-scattering, and light-absorptive embodiments of the current invention preferentially employ a circular assay device as the substrate for the patterned deposition of cleavable signal elements. In an especially preferred embodiment, the assay device is compatible with existing optical disk readers, such as a compact disk (CD) reader or a digital video disk (DVD) reader, and is therefore preferentially a disk of about 120 mm in diameter and about 1.2 mm in thickness. By disk is also intended an annulus.

It will be appreciated, however, that the cleavable reflective signal elements of the present invention may be deposited in spatially addressable patterns on substrates that are not circular and essentially planar, and that such assay devices are necessarily read with detectors suitably adapted to the substrate's shape.

The maximum number of cleavable signal elements, or biobits, that can be spatially discriminated on a optical disk is a function of the wavelength and the numerical aperture of the objective lens. One known way to increase memory capacity in all sorts of optical memory disks, such as CD-ROMS, WORM (Write Once Read Many) disks, and magneto-optical disks, is to decrease the wavelength of the light emitted by the diode laser which illuminates the data tracks of the optical memory disk. Smaller wavelength permits discrimination of smaller data spots on the disk, that is, higher resolution, and thus enhanced data densities. Current CD-ROMs employ a laser with wavelength of 780 nanometers (nm). Current DVD readers employ a laser with wavelength between 635 and 650 nm. New diode lasers which emit, for example, blue light (around 481 nm) would increase the number of signal elements that could be spatially addressed on a single assay device disk of the present invention. Another way to achieve blue radiation is by frequency doubling of infrared laser by non-linear optical material.

Current CD-ROM readers employ both reflection reading and transmission reading. Both data access methods are compatible with the current invention. Gold particles are especially suitable for use as a signal responsive moiety for reflection type CD-ROM readers. Light absorbing dyes are more suitable for transmission type readers such as the ones discussed in U.S. Pat. No. 4,037,257.

5.5.3 Other Signal Responsive Moieties

It will be apparent to those skilled in the art that signal responsive moieties suitable for adaptation to the cleavable spacer of the present invention are not limited to light-reflecting or light-absorbing metal particles or dyes. Suitable signal responsive moieties include, but are not limited to, any composition detectable by spectroscopic, photochemical, biochemical, immunochemical, electrical, optical or chemical means. In some preferred embodiments, suitable signal responsive moieties include calorimetric labels such as colloidal gold or colored glass or plastic (e.g., polystyrene, polypropylene, latex, etc.) beads, biotin for staining with labeled streptavidin conjugate, magnetic beads (e.g., Dynabeads®), radiolabels (e.g., $^3$H, $^{125}$I, $^{35}$S, $^{14}$C, or $^{32}$P), and enzymes (e.g., horse radish peroxidase, alkaline phosphatase and others commonly used in an ELISA).

It will be apparent to those skilled in the art that numerous variations of signal responsive moieties may be adapted to the cleavable spacers of the present invention. A number of patents, for example, provide an extensive teaching of a variety of techniques for producing detectible signals in biological assays. Such signal responsive moieties are generally suitable for use in some embodiments of the current inventions. As a non-limiting illustration, the following is a list of U.S. patents teach the several signal responsive moieties suitable for some embodiments of the current invention: U.S. Pat. Nos. 3,646,346, radioactive signal generating means; U.S. Pat. Nos. 3,654,090, 3,791,932 and 3,817,838, enzyme-linked signal generating means; U.S. Pat. No. 3,996,345, fluorescer-quencher related signal generating means; U.S. Pat. No. 4,062,733, fluorescer or enzyme signal generating means; U.S. Pat. No. 4,104,029, chemiluminescent signal generating means; U.S. Pat. No. 4,160,645, non-enzymatic catalyst generating means; U.S. Pat. No. 4,233,402, enzyme pair signal generating means; U.S. Pat. No. 4,287,300, enzyme anionic charge label. All above-cited U.S. patents are incorporated herein by reference for all purposes.

Other signal generating means are also known in the art, for example, U.S. Pat. Nos. 5,021,236 and 4,472,509, both incorporated herein by reference for all purposes. A metal chelate complex may be employed to attach signal generating means to the cleavable spacer molecules or to an antibody attached as a side member to the spacer molecule. Methods using an organic chelating agent such a DTPA attached to the antibody was disclosed in U.S. Pat. No. 4,472,509, incorporated herein by reference for all purposes.

In yet other embodiments, magnetic spheres may be used in place of reflective spheres and may be oriented by treating the disk with a magnetic field that is of sufficient strength. Since the empty sites will not have any magnetic material present, the location of the spacer molecules remaining can be detected and the information processed to identify the materials in the test sample. Additionally, reflective or magnetic material can be added after hybridization of the sample to provide the signal generating means.

Paramagnetic ions might be used as a signal generating means, for example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Colloidal gold label can be detected by measuring scattered light.

A preferred non-reflective signal generating means is biotin, which may be detected using an avidin or streptavidin compound. The use of such labels is well known to those of skill in the art and is described, for example, in U.S. Pat. Nos. 3,817,837; 3,850,752; 3,939,350; 3,996,345; 4,277,437; 4,275,149 and 4,366,241; each incorporated herein by reference for all purposes.

5.6 Attachment of the Cleavable Spacer Side Members

The side members of the cleavable spacers confer analyte specificity. In a preferred embodiment, the side members are oligonucleotides.

The oligonucleotides can be added by stepwise synthesis on the cleavable spacers prior to attachment of the spacers to the derivatized substrate of the assay device (disk). Alternatively, fully prepared oligonucleotides may be attached in single step directly to the spacer molecules prior to the spacer molecule's attachment to the assay device substrate. In such circumstances, the spacer molecule has protected amino- and/or thiol groups instead of two protected hydroxyl groups. One protective group is removed and an oligonucleotide that has, for example, an isocyanate group at one end is added. A second oligonucleotide is similarly attached as a second side member to the cleavable spacer molecule.

Alternatively, side member oligonucleotides can be synthesized after the attachment of the cleavable spacers onto the substrate, either in a single step using fully prepared oligonucleotides or by stepwise addition. The latter alternative is expected to be preferred when incorporating a large number of assays with different analyte specificity on a single assay device substrate. The general process by which the side members are attached to cleavable spacers previously immobilized on the substrate, whether in a single step or by stepwise addition, is herein termed stamping.

Phosphoramidite chemistry is preferred for preparing the oligonucleotide side members, although other chemistries can be used. In conventional solid phase synthesis, oligonucleotides are prepared by using monomeric phosphoramidites. After conventional synthesis, the oligonucleotides are then detached from the resinous support and purified by a liquid chromatograph to remove reactants, including solvents and unreacted mononucleotides, and to remove shorter oligonucleotides that result from incomplete synthesis. In certain instances the oligonucleotides cannot be so purified, and shorter oligonucleotides contaminate the desired oligonucleotide. This leads to unwanted hybridization. The oligonucleotide contaminants missing only one nucleotide relative to the desired product are the most difficult to deal with, because their binding is almost equal in strength to that of the oligonucleotide having the correct sequence.

In the preparation of oligonucleotides for use as side members in the cleavable reflective signal elements of the present invention, use of trimeric or tetrameric phosphoramidites in the synthesis is advantageous and preferred. Using tetrameric starting materials, for example, 12-mers can be synthesized in three steps. Unavoidable products of incomplete synthesis will in this instance be 8-mers and 4-mers, representing failure of 1 or 2 synthesis steps, respectively. Since the binding of 8-mers is much weaker than the binding of 12-mers, these contaminants do not cause any significant interference.

In applying side members to cleavable spacers by the stepwise addition to spacers immobilized on the surface of the assay device substrate, the oligonucleotides may advantageously be attached to the cleavable spacers by chemical printing, which utilizes the formation of the desired oligonucleotide chemical solution on a printed stamp that is complementary to the spacer molecule distribution on the solid support. Printing is rapid and economical. It can also provide very high resolution. A simple printing method is described, for example, in Science, Vol. 269, pgs. 664–665 (1995).

In this printing method, one of the protecting groups is removed from the spacer molecule on the assay device substrate. The desired oligonucleotides are applied to the stamp surface in a manner that will provide specific oligonucleotides at specific, predetermined locations on the stamp, and the stamp surface is then applied to the spacer-covered substrate support surface, thereby depositing the desired oligonucleotides in the discrete areas in which the spacer molecules reside. Subsequently, the second protecting group is removed and a different oligonucleotide is applied to the activated area, again by chemical stamping. Those steps are illustrated particularly in FIGS. 8A, 8B, 9A,9B, 13 and 14.

Alternatively, the respective oligonucleotides can be applied by ink-jet printing, such as by methods described in U.S. Pats. Nos. 4,877,745 and 5,429,807, the disclosures of which are hereby incorporated by reference.

Either of these direct printing methods is rapid. When trimers or tetramers are used to build oligonucleotides, two printing cycles allows one to create an array of all possible oligos from 6-mers to 8-mers. To contain all 8-mers, the assay device must contain 256×256 different oligos. Additional printing cycles increase the length of oligonucleotides rapidly, although all combinations may not fit onto reasonably sized surfaces and several assay devices may have to be used to represent all such combinations.

An alternative printing process useful in the present invention, concave complementary printing, is shown in FIG. 15. Although only two steps are shown, very large numbers of oligonucleotides can be printed at the same time. A mixture of oligonucleotides is synthesized; for example, 12-mers can be synthesized using a mixture of four phosphoramidites in each step, and as a last step of the synthesis, a very long spacer is attached to each oligonucleotide. On the other end a reactive group, such as an isothiocyanate, is provided. The mixture of oligonucleotides is incubated with the stamp that will bind complementary oligonucleotides at defined sites. During the printing process the spacer will attach with the substrate. The double helices are denatured, for example by heating, and the stamp and substrate can be separated.

Many other methods for the synthesis of oligonucleotides, and in particular, for spatially addressable synthesis of oligonucleotides on solid surfaces, have been developed and are known by those skilled in the art. Methods that prove particularly useful in the present invention are further described in U.S. Pat. Nos. 4,542,102; 5,384,261; 5,405,783; 5,412,087; 5,445,934; 5,489,678; 5,510,270; 5,424,186; 6,624,711; the disclosures of which are incorporated herein by reference.

Other methods that may prove useful in the present invention generally include: (1) Stepwise photochemical synthesis, (2) Stepwise jetchemical synthesis and (3) Fixation of preprepared oligonucleotides. Also a glass capillary array system can be used. In this latter case the synthesis can be performed parallel in all capillaries as is done in an automated DNA synthesizer.

Although the oligonucleotide side elements have been described herein as DNA oligonucleotides synthesized using standard deoxyribonucleotide phosphoramidites, it is known that certain oligonucleotide analogs, such as pyranosyl-RNA (E. Szathmary, Nature 387:662–663 (1997)) and peptide nucleic acids, form stronger duplexes with higher fidelity than natural oligonucleotides. Accordingly, these artificial analogs may be used in the construction of oligonucleotide side elements.

While the oligonucleotide side members are adapted to bind to complementary oligonucleotides, and are thus useful directly in a nucleic acid probe assay, it is a further aspect of the invention to conjugate to these oligonucleotide side members specific binding pair members with utility in other assays.

In these latter embodiments, the noncovalent attachment of binding pair members, such as antibodies, to side member oligonucleotides is mediated through complementarity of side member oligonucleotides and oligonucleotides that are covalently attached to the binding pair member. Use of complementary nucleic acid molecules to effectuate noncovalent, combinatorial assembly of supramolecular structures is described in further detail in co-owned and copending U.S. patent applications Ser. No. 08/332,514, filed Oct. 31, 1994, Ser. No. 08/424,874, filed Apr. 19, 1995, and Ser. No. 08/627,695, filed Mar. 29, 1996, incorporated herein by reference.

As schematized in FIGS. 3A through 3C, oligonucleotide side members 34a, 34b, 35a, and 35b are coupled noncovalently to modified antibodies 38a, 38b, 38c, and 38d to permit an immunoassay. The noncovalent attachment of modified antibodies to side members is mediated through complementarity of side member oligonucleotides and oligonucleotides that are covalently attached to the antibodies.

Although antibodies are exemplified in FIG. 3, it will be appreciated that antibody fragments and derivatives such as Fab fragments, single chain antibodies, chimeric antibodies and the like will also prove useful. In general, binding pair members useful in this embodiment will generally be first members of first and second specific binding pairs, exemplified by antibodies, receptors, etc. that will bind respectively to antigens, ligands, etc.

5.7 Patterned Deposition of Cleavable Reflective Signal Elements on the Assay Device It will be appreciated from the discussion above that the spatial distribution of analyte-responsive cleavable reflective signal elements on the assay device (disk substrate) may be determined at two levels: at the level of attaching the cleavable spacer itself, and additionally at the level of attaching the spacer side members. It will be further appreciated that the spatial distribution of analyte sensitivity may also be determined by a combination of the two.

One method for controlling the distribution of cleavable spacers in the first such step is through patterning the substrate with hydrophilic and hydrophobic domains. At first the hydrophobic surfaces are activated and the hydrophilic surfaces are deactivated so that a hydrophilic and functional spot array separated by a hydrophobic unreactive network is created. If the substrate material is glass, mica, silicon, hydrophilic plastic or analogous material, the whole surface is first rendered reactive by treatment with acid or base. The intermediate space between spots is silanized. This is best performed by using a grid as a stamp. If on the other hand the substrate is a hydrophobic plastic, it can be activated by plasma treatment in the presence of ammonia and then silanized as a hydrophilic substrate. Using resist material in conjunction with lithographic or mechanical printing to remove the resist at desired sites, activation can be performed at those sites.

Onto the reactive spots is preferably attached a hydrophilic spacer such as polyethyleneglycol (PEG). If the, substrate contains an amino or a thiol group, PEG can be preactivated in the other end with a variety of functional groups, which are known to couple with an amino or thiol group. These include isocyanate, maleimide, halogenoacetyl and succinimidoester groups.

A photoresist may also profitably be used to pattern the deposition of cleavable signal elements. The resist is partially depolymerized by incident laser light during fabrication and can be dissolved from these areas. The exposed plastic or metalized plastic is treated chemically, for example, aminated by ammonia plasma. After the resist is removed, the spacer, side members, and signalling moiety are connected into the treated area as needed. The use of photoresists for the patterning of master disks is well known in the compact disk fabrication arts.

Alternatively, instead of using a resist, a solid mask containing small holes and other necessary features can be used during ammonia plasma treatment. Holes have a diameter of about 1 to 3 micrometers. The holes are located circularly in the mask, forming a spiral track or a pattern that is a combination of spiral and circular paths. The mask can be metal or plastic. Several metals, such as aluminum, nickel or gold can be used. Polycarbonate is a preferred plastic, because it will retain shape well. Plastics are reactive with the ammonia plasma, however, and a preferred method for using plastic masks therefore involves depositing a metal layer on the plastic, by evaporation, sputtering, or other methods known in the art. Holes may be made in the mask by laser. Those with skill in the art will appreciate that it is possible to create 1000 1 μm-sized holes in one second in a thin metal or plastic plate. Alternatively, the holes can be etched by using conventional methods known in the semiconductor industry. In the mask approach to patterning the deposition of signal elements, the mask is pressed against the substrate and the ammonia plasma applied. The mask may be used repeatedly.

As should appreciated, the spatial distribution of analyte sensitivity may also be conferred by the patterned application of spacer side arms.

With reference to the printing method above-described, the schematics of one possible oligonucleotide stamp is shown in FIG. 13. The stamp has holes which are filled with a certain chemical that will be used to provide the desired building block of the oligonucleotide being synthesized. In FIG. 13 each row is filled with the same chemical and accordingly four different chemicals can be used during one stamping cycle in the example given in FIG. 13. In commercial systems the number of rows will be considerably higher, typically 64–256, although lower and higher numbers of rows can be used in special cases. The linear stamp is advantageous if all possible oligonucleotides of certain size are to be fabricated onto the assay device substrate.

In this way all possible hexameric combinations of a given set of oligonucleotide building blocks can be prepared. For instance, trimer phosphoramidites can be formed by two reaction cycles by using a 64-row linear stamp. Each of the 64 different trimer phosphoramidites is fed into one row of holes. After printing the phosphoramidites, the oxidizer, deblocker and cap reagent are printed. As these chemicals are the same at each spot, the stamp can be a flat plate or the whole substrate can be simply dipped into the reagent solution. The substrate is rotated 90° and the same cycle is repeated. In this way all possible combinations of trimers have been fabricated. Analogously all combinations of any set of oligonucleotide amidites can be fabricated.

In FIG. 14 is an example showing the fabrication of all possible combinations of four different oligonucleotide amidites. After the first printing cycle all spots in each horizontal row contain the same oligonucleotide, but each row has a different oligonucleotide. These oligonucleotide fragments are denoted by numbers 1, 2, 3 and 4 in FIG. 14. When the stamp is rotated 90° and the printing cycle is repeated all combinations of four oligonucleotides are formed.

The foregoing orthogonal printing process is particularly advantageous in the production of signal elements of this invention in the embodiment of the disk. Orthogonal printing facilitates the distribution of the array of spacer molecules in a pattern of concentric circles, similar to the information that is placed onto audio or CD-ROM compact disks in annular patterns. One preferred variation of an orthogonal printing process employs superimposition of two sets of spiral stamps with opposite chirality.

The positioning of the stamp must be accurate within about 1 μm. This can be achieved mechanically using two to four guiding spike hole pairs or by an optoelectronically guided microtranslator. A removable reflective coating may be deposited onto two perpendicular sides of the substrate and the stamp and their relative positioning measured by an interferometer. The substrate and stamp can also have a pair of microprisms which must be perfectly aligned in order for the light pass into the photodetector.

FIGS. 11A through 11G illustrate various useful patterns of spatially addressable deposition of cleavable reflective signal elements on circular, planar disk substrates. FIG. 11A particularly identifies an address line, encodable on the disk substrate, from which the location of the cleavable spacers may be measured. In FIG. 11A, the cleavable spacer molecules are deposited in annular tracks. FIG. 11B demonstrates spiral deposition of cleavable signal elements, and particularly identifies a central void of the disk annulus particularly adapted to engage rotational drive means. FIG. 11C demonstrates deposition of cleavable signal elements in a pattern suitable for assay of multiple samples in parallel, with concurrent encoding of interpretive software on central tracks. FIG. 11D schematically represents an embodiment in which the assay device substrate has further been microfabricated to segregate the individual assay sectors, thereby permitting rotation of the assay device during sample addition without sample mixing.

FIG. 11E schematically represents an embodiment in which the assay device substrate has further been microfabricated to compel unidirectional sample flow during rotation of the assay device. Techniques for microfabricating solid surfaces are well known in the art, and are described particularly in U.S. Pat. Nos. 5,462,839; 5,112,134; 5,164,319; 5,278,048; 5,334,837; 5,345,213, which are incorporated herein by reference.

FIG. 11F demonstrates deposition of cleavable signal elements in a spatial organization suitable for assaying 20 samples for 50 different analytes each. FIG. 11G demonstrates the orthogonally intersecting pattern created by superimposition of spiral patterns with spiral arms of opposite direction or chirality.

The spatial distribution of cleavable reflective signal elements, or biobits, on the surface of the assay device may be designed to facilitate the quantitation of analyte concentration.

Thus, in some embodiments, analyte capture is used for quantification. In one implementation, the assay device is patterned with a uniform density of biobits dedicated to each chosen analyte. A test sample is introduced onto the disk in the center of the disk. By applying rotational force, the test sample is spread radially to the periphery. In the process of spreading, analytes are captured by the respective cognate side element of the cleavable signal element, reducing the concentration of analytes at the sample front.

With sufficient density of biobits relative to the incident concentration, all analytes are captured before the sample front reaches the periphery of the assay device. The concentration of each analyte may then be determined according to the location of the positive biobit that is farthest from the sample introduction site.

It will be appreciated that a greater dynamic range of analyte concentration will be detectable if more biobits are dedicated to the detected analyte. In the embodiment just described, the uniform density of biobits would be increased. It will further be appreciated, however, that the density of biobits need not be constant, and that a linear or exponentially changing density of biobits may be employed, as measured from the center of the disk to the periphery, to change the dynamic range of concentration detection.

In other embodiments and aspects of the present invention, biobits with different affinities for the chosen analyte may be attached to the assay device to similar effect, that is, to increase the dynamic range of concentration detection.

It is further contemplated that other geometries may be used to convey concentration information. FIG. 16 demonstrates one geometry in which a single sample is channeled in parallel into four distinct sectors of the assay device. If either the density of biobits, the affinity of the biobits, or both density and affinity of biobits in the four sectors differs, a large dynamic range of concentration may be determined by detecting the position in each sector of the positive biobit most distal from the sample application site.

In other embodiments, equilibrium assays are contemplated. Concentration is thus determined by sampling the entire disk and determining the percentage of positive biobits per analyte.

In each of these embodiments, generally a number of biobits are dedicated to detection of positive and negative controls.

In other embodiments, cleavable reflective signal elements (biobits) specific for multiple different analytes are patterned in a number of different formats. For example, biobits of distinct specificity are mixed in each sector of a disk. Alternatively, they may be separated into different sectors. The ability to pattern specific biobits into predefined locations and the ability to decipher the identity of biobits by detectors such as a CD-ROM reader makes flexible designs possible. One of skill in the art would appreciate that the design of patterns should be tested and adjusted using test samples containing known analytes of different concentrations.

5.8 Alternative Assay Device Geometries

Viruses are typically nearly spherical particles having diameter less than 0.5 μm. Bacteria are commonly either spherical or rod shaped; their largest dimension is usually less than 2 μm excluding flagella and other similar external fibers. These pathogens are somewhat smaller, or about the same size, as the gold spheres used in the cleavable signal elements of the present invention. them. Their interaction simultaneously with two side members of the cleavable signal element above-described may, therefore, be sterically inhibited.

Thus, an alternative geometry dispenses altogether with the cleavable spacers. One analyte-specific side member is attached directly to the substrate surface of the assay device in spatially addressable fashion. The second side member, specific for a second site of the chosen analyte, is attached directly to the signal responsive moiety. In preferred embodiments, that moiety is a gold sphere. In this alternative geometry, recognition of analyte creates a direct sandwich of the formula: substrate-first side member-analyte-second side member-signal responsive moiety. This geometry might be said to be a limiting case in which "m" in the formula for the cleavable spacer is zero.

This particular geometry may also prove useful in detecting nucleic acid hybridization, as shown in FIG. 17.

In this alternative geometry, if the signal responsive moiety is reflective, the information encoding is similar to that in the geometries presented earlier—the presence of analyte is signalled by reflection. Alternatively, if the signal responsive moiety is opaque, e.g. through incorporation of dye, the encoding is reversed: the presence of analyte is signalled by absence of reflection from the metallic layer of the device substrate.

Magnetic plastic spheres may provide particular advantages in this alternative geometry. Because they contain magnetic particles inside, they are less transparent than latex spheres. Furthermore, magnetism can be used to remove weakly bound spheres that are otherwise difficult to remove, as, e.g., latex spheres, because their density is close to that of water and centrifugal force would prove ineffectual.

A further variant of this alternative geometry takes advantage of agglutination in a reflection assay, as shown in FIG. 18. In this alternative, the signal responsive moiety are preferably microspheres. These microspheres are relatively small (30–600 nm), so that one alone does not block the light efficiently.

The invention may be better understood by reference to the following nonlimiting examples.

6. EXAMPLE I

Increasing the Specificity of a Nucleic Acid Hybridization Assay

In a direct nucleic acid hybridization assay, the side elements of the cleavable signal element are oligonucleotides designed to hybridize with distinct sites on a chosen, predetermined, nucleic acid to be detected in the sample. For many applications of this methodology, cross-reactivity with sample oligonucleotides having even a single mismatched nucleotide should be minimized. In particular, nucleic acid hybridization assays adapted to use the cleavable reflective signal element of the present invention for detection of point mutations, as, e.g., for detection of point mutations in the BRCA1 and BRCA2 genes that predispose to breast and ovarian cancers, must be able to discriminate as between nucleic acid samples containing a single mismatched nucleotide.

The longer the oligonucleotide side elements of the cleavable signal element—and thus the longer the sequence that is complementary as between the side elements and the nucleic acid sample—the greater the possibility of erroneously recognizing a mismatched sample, since the strength of hybridization, even given the presence of a mismatch, will be reasonably high.

Thus, one way to reduce erroneous recognition of mismatched nucleic acid sequences is to reduce the length of the side element oligonucleotides. Specificity is increased by shortening side-arms to 8-mers or even to 6-mers. These will still hybridize at room temperature, depending on stringency of wash, conditions of which are well known in the art. The mismatched oligonucleotides would use five or fewer nucleotides for pairing and will form highly unstable binding at room temperature.

This solution, however, presents its own problem: the relatively short overall length, 12–16 nucleotides, used for recognition leads to a concomitantly reduced overall strength of the hybridization required to restrain the signal responsive moiety of the cleaved signal elements. Use of ligase, as depicted in FIGS. 2E–2F, partly solves this problem. Ligation will not only provide a stronger bond, but will further act to ensure selectivity, since DNA ligase will not join oligonucleotides if there is a mismatch near the end of the oligonucleotides. Because the oligonucleotides are short, no mismatched base pairs are accepted. Ligase serves as a very strict double-check for the match of the oligos.

Figure 2D:
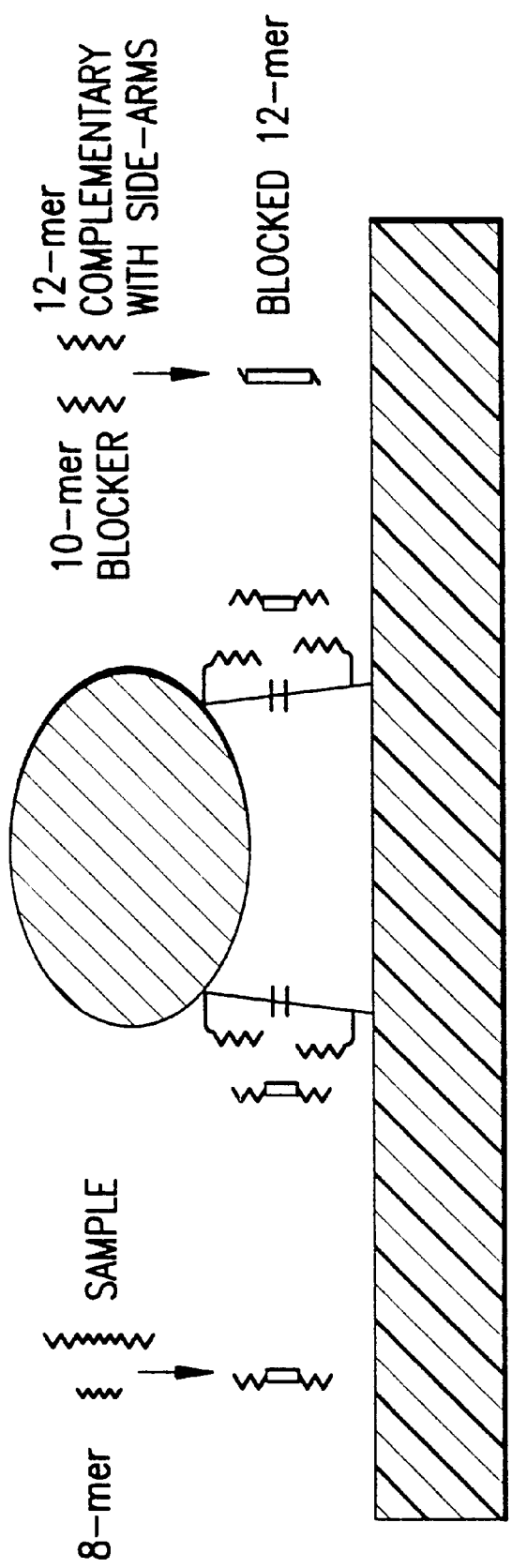

An alternative, and complementary, solution, uses the triple recognition principle illustrated in FIG. 2D–2E constructively to shorten the test sample sequence available for hybridization to the cleavable signal element side elements. A soluble specificity-enhancing oligonucleotide, for example an 8-mer, which is complementary to the central part of the sample oligonucleotide, is added to the sample solution prior to contacting the assay device with the fluid sample. This 8-mer hybridizes well under the testing conditions. The side elements of the cleavable signal elements recognize six nucleotides in the immediate vicinity of the preformed duplex.

Ligation will ensure selectivity and will also provide a strong bond. Ligase will not join oligonucleotides if there is a mismatch near the end of the oligonucleotides. Because the oligonucleotides are short, no mismatched base pairs are accepted. Ligase serves as a very strict double-check for the match of the oligos.

It will be apparent that the soluble specificity-enhancing oligonucleotide, shown here as an 8-mer, that is added to the test sample may be designed to position the potential mismatch near the sample ends, where mismatch will be most disfavored for binding to the side elements.

Moreover, because addition of ligase ensures a covalent loop, stringency of wash may be increased by addition of chaotropic agents and/or by heating to remove any unselective oligonucleotides.

The "blocked" sample oligonucleotide suitable for and capable of binding correctly to the side elements may be mimicked, however, by a sample nucleic acid that possesses the requisite terminal hexanucleotide sequences directly connected to one another without the intervening 8-mer sequence.

As shown in FIG. 2D, further addition to the sample of a 10-mer with sequence equally drawn from the first side element oligonucleotide sequence and second side element oligonucleotide sequence will prevent such binding upon contacting the assay device of the present invention. The combination 8+10+8 of the specificity-enhancing soluble oligonucleotides is presently preferred, but other combinations, such as 7+9+7 and 8+8+8 may be used.

A further method to increase specificity includes use of so-called padlock probes, in which circularized oligonucleotides are catenated, permitting extensive washing to remove weakly bound probes. Padlock probes can achieve a 50:1 discrimination between complementary and singly mismatched oligonucleotides (Nilsson et al., Science 265:2085 (1994)), while with conventional probes this ratio is typically between 2:1 and 10:1.

Oligonucleotide side members having the following sequences are prepared by automated synthesis so that each of them contains a terminal thio (or aliphatic amino) group, depending on the attachment site with the cleavable spacer molecule (5' end or 3' end).

The cleavable spacer molecules are synthesized with two aliphatic amino groups, in place of the protected hydroxy groups above-described, and one group is protected by monomethoxytrityl (MMT, acid labile) and the other group is protected by fluorenyloxycarbonyl (FMOC, base labile). After the removal of the FMOC-group, the amino function is allowed to react under aqueous conditions with 4-(N-maleimidomethyl)-cyclohexane-1-carboxylic acid N-hydroxysuccinimide ester (SMMC). Thiol derivatized Ia is added to the spacer molecule and allowed to couple to the spacer molecule. Subsequently, MMT is removed by treatment with acetic acid, and after washing with buffer, pH 8, SMCC is-added, and oligonucleotide IIb is allowed to couple with the spacer molecule. The spacer molecules prepared above are attached to a polycarbonate substrate.

A test sample containing 5'-GCCCACACCGCCGGCGCC-3'(SEQ ID NO:6) is prepared and allowed to contact the cleavable signal element at a temperature that approximates the $T_m$ of the side members Ia and Ib. The temperature of the sample solution is heated to about 20 degrees Centigrade above the $T_m$. Subsequently, the signal element is treated with 0.1M sodium fluoride solution and washed. Spacer molecules remaining attached to the surface signal the presence of, and tethering by, 5'-GCCCACACCGCCGGCGCC-3'(SEQ ID NO:6)

The foregoing process is applied to the analysis of 5'GCCCACACTGCCGGCGCC-3'(SEQ ID NO:7) GCCCACACGGCCGGCGCC-3'(SEQ. ID. NO:8) and 5'-GCCCACAGCCGGCGCC-3'(SEQ ID NO:9) using, respectively, spacer molecules incorporating side members IIa and IIb, IIIa and IIIb, and IVa and IVb.

7. EXAMPLE II

Detection of HIV-1

HIV-1 proviral DNA from clinical samples is amplified as follows, essentially as described in U.S. Pat. No. 5,599,662, incorporated herein by reference.

Peripheral blood monocytes are isolated by standard Ficoll-Hypaque density gradient methods. Following isolation of the cells, the DNA is extracted as described in Butcher and Spadoro, Clin. Immunol. Newsletter 12:73–76 (1992), incorporated herein by reference.

Polymerase chain reaction is performed in a 100 µl reaction volume, of which 50 µl is contributed by the sample. The reaction contains the following reagents at the following initial concentrations:
  10 mM Tris-HCl (pH 8.4)
  50 mM KCl
  200 µM each DATP, dCTP, dGTP, and dUTP
  25 pmoles of primer 1, of sequence shown below
  25 pmoles of primer 2, of sequence shown below
  3.0 mM $MgCl_2$
  10 % glycerol
  2.0 units of Taq DNA polymerase (Perkin-Elmer)
  2.0 units UNG (Perkin-Elmer)
Primer 1: 5'-TGA GAC ACC AGG AAT TAG ATA TCA GTA CAA TGT-3'(SEQ ID NO:10)
Primer 2: 5'-CTA AAT CAG ATC CTA CAT ATA AGT CAT CCA TGT-3'(SEQ ID NO:11)

Amplification is carried out in a TC9600 DNA thermal cycler (Perkin Elmer, Norwal, Conn.) using the following temperature profile: (1) pre-incubation—50° C. for 2 minutes; (2) initial cycle—denature at 94° C. for 30 seconds, anneal at 50° C. for 30 seconds, extend at 72°for 30 seconds; (3) cycles 2 to 4—denature at 94° C. for 30 seconds, anneal for 30 seconds, extend at 72° C. for 30 seconds, with the annealing temperature increasing in 2° C. increments (to 58° C.) as compared to cycle 1; (4) cycles 5 to 39—denature at 90° C. for 30 seconds, anneal at 60° C. for 30 seconds, extend at 72° C. for 30 seconds.

Following the temperature cycling, the reaction mixture is heated to 90° C. for 2 minutes and diluted to 1 ml. Alternatively, the sample is stored at −20° C., and after thawing, heated to 90° C. for 2 minutes then diluted to 1 ml.

Cleavable spacers with siloxane moiety are synthesized and attached in a uniform density to a derivatized 120 mm polycarbonate disk substrate essentially as set forth in sections 5.2 and 5.3 hereinabove. The following side members are then stamped on the cleavable spacers:
  first side member: 5'-TAG ATA TCA GTA CAA-3'(SEQ ID NO:12)
  second side member: 3'-TAT TCA GTA GGT ACA-5' (SEQ ID NO:13)

A suspension of gold microspheres, 1–3 µm in diameter, is added dropwise to the disk, which is gently rotated to distribute the gold particles. Gold particles are added until the effluent contains the same density of particles as the initial suspension, thus ensuring saturation of the cleavable spacers.

Sample is applied at room temperature dropwise near the center of the assay device which is rotated at a continuous speed. Rotation is halted after the sample front reaches the periphery, and the disk is incubated stationary at room temperature for 3–5 minutes.

One ml of sample buffer is added dropwise as a wash while the disk is rotated. One ml of 100 mM sodium fluoride is added and distributed by disk rotation. The disk is incubated stationary for 1–2 minutes, then 5 ml of sample buffer is added dropwise during vigorous rotation of the assay disk.

The disk is dried, then read directly in a CD-ROM reader programmed to assay each predetermined site upon which cleavable spacers were deposited.

The present invention is not to be limited in scope by the exemplified embodiments and examples, which are intended as illustrations of individual aspects of the invention. Indeed, various modifications thereto and equivalents and variations thereof in addition to those shown and described herein will become apparent to those skilled in the art from the foregoing description and accompanying drawings. Such modifications are intended to be and are included within the scope of the appended claims.

All publications cited herein are incorporated by reference in their entirety.

What is claimed is:

1. A cleavable signal element, comprising:
    a cleavable spacer, said cleavable spacer having a substratae-attaching end, a signal-responsive end, and a cleavage site intermediate said substrate-attaching end and said signal responsive end;
    a signal responsive moiety;
    a first side member adapted to bind a first site on a chosen analyte;
    a second side member adapted to bind a second site of said chosen analyte;
    said signal responsive moiety being attached to said cleavable spacer at said signal responsive end, said first side member being attached to said cleavable spacer intermediate said signal responsive end and said cleavage site, and said second side member being attached to said cleavable spacer intermediate said cleavage site and said substrate attaching end; and
    said signal responsive moiety remaining bound to the substrate after cleavage at the cleavage site only when said first and second side members are bound to said chosen analyte.

2. The cleavable signal element of claim 1, wherein said signal responsive moiety is adapted to reflect or scatter incident light.

3. The cleavable signal element of claim 2, wherein said signal responsive moiety is a metal microsphere.

4. The cleavable signal element of claim 3, wherein said metal microsphere is essentially a metal selected from the group of gold, silver, nickel, platinum, chromium and copper.

5. The cleavable signal element of claim 4, wherein said metal microsphere is essentially of gold.

6. The cleavable signal element of claim 5, wherein said gold microsphere has a diameter between 1 nm–10 µm.

7. The cleavable signal element of claim 6, wherein said gold microsphere has a diameter between 0.5–5 µm.

8. The cleavable signal element of claim 7, wherein said gold microsphere has a diameter between 1–3 μm.

9. The cleavable signal element of claim 1, wherein said cleavage site is susceptible to chemical cleavage.

10. The cleavable signal element of claim 9, wherein said chemically susceptible cleavage site includes at least one siloxane group.

11. The cleavable signal element of claim 1, wherein said first side member and said second side member include oligonucleotides.

12. The cleavable signal element of claim 11, wherein said first and second side member oligonucleotides are 5 mers–20 mers.

13. The cleavable signal element of claim 12, wherein said first and second side member oligonucleotides are 8 mers–17 mers.

14. The cleavable signal element of claim 12, wherein said first and second side member oligonucleotides are 8 mers–12 mers.

15. The cleavable signal element of claim 1, wherein
said first side member includes a first member of a first specific binding pair,
said second side member includes a first member of a second specific binding pair, and
said second member of said first specific binding pair and said second member of said second specific binding pair are each present on the surface of a single analyte.

16. The cleavable signal element of claim 15, wherein said first member of said first specific binding pair includes a first antibody or antibody fragment and said first member of said second specific binding pair includes a second antibody, antibody fragment, or antibody derivative.

17. The cleavable signal element of claim 15, wherein
said first side member includes a first side member oligonucleotide,
said second side member includes a second side member oligonucleotide,
said first member of said first specific binding pair includes a first binding pair oligonucleotide,
said first member of said second specific binding pair includes a second binding pair oligonucleotide, and
said first side member oligonucleotide includes sequence complementary to sequence included in said first binding pair oligonucleotide, said second side member oligonucleotide includes sequence complementary to sequence included in said second binding pair oligonucleotide, and said complementary sequences are noncovalently associated.

* * * * *

```
                        SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
         (A) LENGTH: 9
         (B) TYPE: nucleic acid
         (C) STRANDEDNESS: single-stranded DNA
         (D) TOPOLOGY: linear (ii) MOLECULE TYPE: oligonucleotide (xi) SEQUENCE DESCRIPTION: SEQ ID NO: 1:

CGGGTGTGG                                                                  9

(2) INFORMATION FOR SEQ ID NO: 2:

(i) SEQUENCE CHARACTERISTICS:
         (A) LENGTH: 9
         (B) TYPE: nucleic acid
         (C) STRANDEDNESS: single-stranded DNA
         (D) TOPOLOGY: linear (ii) MOLECULE TYPE: oligonucleotide (xi) SEQUENCE DESCRIPTION: SEQ ID NO: 2:

CGGGTGTGA                                                                  9

(2) INFORMATION FOR SEQ ID NO: 3:

(i) SEQUENCE CHARACTERISTICS:
         (A) LENGTH: 9
         (B) TYPE: nucleic acid
         (C) STRANDEDNESS: single-stranded DNA
         (D) TOPOLOGY: linear (ii) MOLECULE TYPE: oligonucleotide (xi) SEQUENCE DESCRIPTION: SEQ ID NO: 3:

CGGGTGTGC                                                                  9

(2) INFORMATION FOR SEQ ID NO: 4:

(i) SEQUENCE CHARACTERISTICS:
         (A) LENGTH: 9
         (B) TYPE: nucleic acid
         (C) STRANDEDNESS: single-stranded DNA
         (D) TOPOLOGY: linear (ii) MOLECULE TYPE: oligonucleotide (xi) SEQUENCE DESCRIPTION: SEQ ID NO: 4:

CGGGTGTGT                                                                  9
```

(2) INFORMATION FOR SEQ ID NO: 5:

(i) SEQUENCE CHARACTERISTICS:
        (A) LENGTH: 9
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 5:

CGGCCGCGG                                                                                       9

(2) INFORMATION FOR SEQ ID NO: 6:

(i) SEQUENCE CHARACTERISTICS:
        (A) LENGTH: 18
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 6:

GCCCACACCG CCGGCGCC                                                           18

(2) INFORMATION FOR SEQ ID NO: 7:

(i) SEQUENCE CHARACTERISTICS:
        (A) LENGTH: 18
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 7:

GCCCACACTG CCGGCGCC                                                           18

(2) INFORMATION FOR SEQ ID NO: 8:

(i) SEQUENCE CHARACTERISTICS:
        (A) LENGTH: 18
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 8:

GCCCACACGG CCGGCGCC                                                           18

(2) INFORMATION FOR SEQ ID NO: 9:

(i) SEQUENCE CHARACTERISTICS:
        (A) LENGTH: 16
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 9:

GCCCACAGCC GGCGCC                                                               16

(2) INFORMATION FOR SEQ ID NO: 10:

(i) SEQUENCE CHARACTERISTICS:
        (A) LENGTH: 33

-continued

```
            (B) TYPE: nucleic acid
            (C) STRANDEDNESS: single-stranded DNA
            (D) TOPOLOGY: linear (ii) MOLECULE TYPE: oligonucleotide (xi) SEQUENCE DESCRIPTION: SEQ ID NO: 10:

TGAGACACCA GGAATTAGAT ATCAGTACAA TGT                                       33

(2) INFORMATION FOR SEQ ID NO: 11:

(i) SEQUENCE CHARACTERISTICS:
            (A) LENGTH: 33
            (B) TYPE: nucleic acid
            (C) STRANDEDNESS: single-stranded DNA
            (D) TOPOLOGY: linear (ii) MOLECULE TYPE: oligonucleotide (xi) SEQUENCE DESCRIPTION: SEQ ID NO: 11:

CTAAATCAGA TCCTACATAT AAGTCATCCA TGT                                       33

(2) INFORMATION FOR SEQ ID NO: 12:

(i) SEQUENCE CHARACTERISTICS:
            (A) LENGTH: 15
            (B) TYPE: nucleic acid
            (C) STRANDEDNESS: single-stranded DNA
            (D) TOPOLOGY: linear (ii) MOLECULE TYPE: oligonucleotide (xi) SEQUENCE DESCRIPTION: SEQ ID NO: 12:

TAGATATCAG TACAA                                                           15

(2) INFORMATION FOR SEQ ID NO: 13:

(i) SEQUENCE CHARACTERISTICS:
            (A) LENGTH: 15
            (B) TYPE: nucleic acid
            (C) STRANDEDNESS: single-stranded DNA
            (D) TOPOLOGY: linear (ii) MOLECULE TYPE: oligonucleotide (xi) SEQUENCE DESCRIPTION: SEQ ID NO: 13:

TATTCAGTAG GTACA                                                           15
```